(12) United States Patent
Chen et al.

(10) Patent No.: US 10,934,285 B2
(45) Date of Patent: Mar. 2, 2021

(54) COMPOUNDS AND COMPOSITIONS FOR INHIBITING THE ACTIVITY OF SHP2

(71) Applicant: Novartis AG, Basel (CH)

(72) Inventors: Zhuoliang Chen, Belmont, MA (US); Jorge Garcia Fortanet, Wilmington, MA (US); Rajesh Karki, Quincy, MA (US); Matthew J. Lamarche, Reading, MA (US); Dyuti Majumdar, Cambridge, MA (US); Lawrence Blas Perez, Silver Spring, MD (US); Martin Sendzik, Belmont, MA (US); Troy Douglas Smith, Nashua, NH (US); Fan Yang, West Roxbury, MA (US); Bing Yu, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/309,076

(22) PCT Filed: Jun. 12, 2017

(86) PCT No.: PCT/IB2017/053469
§ 371 (c)(1),
(2) Date: Dec. 11, 2018

(87) PCT Pub. No.: WO2017/216706
PCT Pub. Date: Dec. 21, 2017

(65) Prior Publication Data
US 2020/0002330 A1 Jan. 2, 2020

Related U.S. Application Data

(60) Provisional application No. 62/349,697, filed on Jun. 14, 2016.

(51) Int. Cl.
C07D 487/14 (2006.01)
C07D 471/04 (2006.01)
C07D 401/14 (2006.01)
C07D 403/14 (2006.01)
C07D 455/02 (2006.01)
C07D 487/04 (2006.01)
C07D 495/04 (2006.01)
C07D 513/04 (2006.01)
C07D 519/00 (2006.01)

(52) U.S. Cl.
CPC ......... C07D 471/04 (2013.01); C07D 401/14 (2013.01); C07D 403/14 (2013.01); C07D 455/02 (2013.01); C07D 487/04 (2013.01); C07D 495/04 (2013.01); C07D 513/04 (2013.01); C07D 519/00 (2013.01)

(58) Field of Classification Search
CPC .... A61K 31/519; A61K 31/53; A61K 31/517; A61K 31/542; C07D 471/04; C07D 487/04; C07D 487/14

USPC ............ 514/259.2, 267, 259.4; 544/350, 182
See application file for complete search history.

(56) References Cited

U.S. PATENT DOCUMENTS

| 4,613,603 | A | 9/1986 | Biziere et al. |
| 9,567,318 | B2 | 2/2017 | Chiosis et al. |
| 9,815,813 | B2 | 11/2017 | Chen et al. |
| 10,077,276 | B2 | 9/2018 | Chen et al. |
| 10,093,646 | B2 | 10/2018 | Chen et al. |
| 2003/0171359 | A1 | 9/2003 | Dahmann et al. |

(Continued)

FOREIGN PATENT DOCUMENTS

| CN | 102753177 A | 10/2012 |
| EP | 0 459 819 A2 | 4/1991 |

(Continued)

OTHER PUBLICATIONS

Whelligan, et al., "Aminopyrazine Inhibitors Binding to an Unusual Inactive Conformation of the Mitotic Kinase Nek2: SAR and Structural Characterization", Journal of Medicinal Chemistry, 2010, vol. 53, No. 21, pp. 7682-7698.

(Continued)

Primary Examiner — Jeffrey H Murray
(74) Attorney, Agent, or Firm — Scott W. Reid

(57) ABSTRACT

The present invention relates to compounds of formula I: in which $Y_1$, $Y_2$, $R_1$, $R_2$ and $R_3$ are defined in the Summary of the Invention; capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

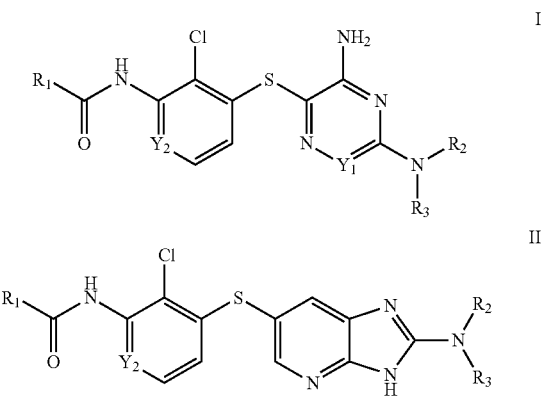

5 Claims, No Drawings
Specification includes a Sequence Listing.

(56) References Cited

U.S. PATENT DOCUMENTS

| | | |
|---|---|---|
| 2004/0229873 A1 | 11/2004 | Harbige et al. |
| 2005/0222159 A1 | 10/2005 | Tsutsumi et al. |
| 2006/0183911 A1 | 8/2006 | Charrier et al. |
| 2008/0024964 A1 | 1/2008 | Lev et al. |
| 2010/0029941 A1 | 2/2010 | Wallace et al. |
| 2011/0257184 A1 | 10/2011 | Qu et al. |
| 2011/0306606 A1 | 12/2011 | Ryu et al. |
| 2011/0319381 A1 | 12/2011 | Abouabdellah et al. |
| 2012/0190699 A1 | 7/2012 | Charrier et al. |
| 2012/0252818 A1 | 10/2012 | Chiosis et al. |
| 2013/0116430 A1 | 5/2013 | Fujiwara et al. |
| 2013/0184259 A1 | 7/2013 | Charrier et al. |
| 2015/0315207 A1 | 11/2015 | Morales et al. |
| 2017/0001975 A1 | 1/2017 | Chen et al. |
| 2017/0015680 A1 | 1/2017 | Chen et al. |
| 2018/0065949 A1 | 3/2018 | Chen et al. |
| 2018/0186770 A1 | 7/2018 | Chen et al. |
| 2018/0201623 A1 | 7/2018 | Chen et al. |
| 2018/0251471 A1 | 9/2018 | Chen et al. |
| 2018/0362496 A1 | 12/2018 | Chen et al. |

FOREIGN PATENT DOCUMENTS

| | | |
|---|---|---|
| EP | 799617 A2 | 8/1997 |
| JP | 6-340634 | 12/1994 |
| WO | 1991019305 A1 | 12/1991 |
| WO | 2000059893 A1 | 10/2000 |
| WO | 2002024679 A1 | 3/2002 |
| WO | 2005117909 A1 | 12/2005 |
| WO | 2006065946 A1 | 6/2006 |
| WO | 2007031529 A1 | 3/2007 |
| WO | 2008055959 A1 | 5/2008 |
| WO | 2008100412 A1 | 8/2008 |
| WO | 2008110611 A1 | 9/2008 |
| WO | 2009131687 A2 | 10/2009 |
| WO | 2009150230 A1 | 12/2009 |
| WO | 2009158571 A1 | 12/2009 |
| WO | 2010008739 A2 | 1/2010 |
| WO | 2010011666 A2 | 1/2010 |
| WO | 2010048149 A2 | 4/2010 |
| WO | 2010121212 A2 | 10/2010 |
| WO | 2011078143 A1 | 6/2011 |
| WO | 11022440 A2 | 8/2011 |
| WO | 2012009217 A1 | 1/2012 |
| WO | 2012016217 A1 | 2/2012 |
| WO | 2012027495 A1 | 3/2012 |
| WO | 2012052948 A1 | 4/2012 |
| WO | 2012/082689 A1 | 6/2012 |
| WO | 2013040044 A1 | 3/2013 |
| WO | 2013096093 A1 | 6/2013 |
| WO | 2013182546 A1 | 12/2013 |
| WO | 2014054053 A2 | 4/2014 |
| WO | 2014160521 A1 | 10/2014 |
| WO | 2015092819 A2 | 6/2015 |
| WO | 2015/107493 A1 | 7/2015 |
| WO | 2015107493 A1 | 7/2015 |
| WO | 2015107494 A1 | 7/2015 |
| WO | 2015107495 A1 | 7/2015 |
| WO | 2015168466 A1 | 11/2015 |
| WO | 2016023404 A1 | 2/2016 |
| WO | 2016203405 A1 | 12/2016 |
| WO | 2016203406 A1 | 12/2016 |
| WO | 2017/156397 A1 | 9/2017 |
| WO | 2017/211303 A1 | 12/2017 |
| WO | 2018/013597 A4 | 1/2018 |
| WO | 2018/057884 A1 | 3/2018 |
| WO | 2018/081091 A1 | 5/2018 |
| WO | 2018/130928 A1 | 7/2018 |
| WO | 2018/136264 A9 | 7/2018 |
| WO | 2018/136265 A1 | 7/2018 |
| WO | 2018/172984 A1 | 9/2018 |
| WO | 2019/051084 A1 | 3/2019 |
| WO | 2019/067843 A1 | 4/2019 |
| WO | 2019/075265 A1 | 4/2019 |
| WO | 2019/118909 A1 | 6/2019 |
| WO | 2019/165073 A1 | 8/2019 |
| WO | 2019/183367 A1 | 9/2019 |
| WO | 2019/199792 A1 | 10/2019 |

OTHER PUBLICATIONS

Ellingboe, et al., (Pyrimidinyloxy)acetic Acids and Pyrimidineacetic Acids as a Novel Class of Aldose Reductase Inhibitors, Journal of Medicinal Chemistry, 1990, vol. 33, pp. 2892-2899.

Aso, et al., "Discovery of pyrrolo[2,3-d]pyrimidin-4-ones as corticotropin-releasing factor 1 receptor agonists with a carbonyl-based hydrogen bonding acceptor", Bioorganic & Medicinal Chemistry Letters, 2011, pp. 2365-237, vol. 21, Elsevier Ltd.

Fortanet, et al., "Allosteric Inhibition of SHP2: Identification of a Potent, Selective, and Orally Efficacious Phosphatase Inhibitor", Journal of Medicinal Chemistry, Jun. 27, 2016, pp. 7773-7782, vol. 59, American Chemical Society.

Lala and Orucevic, "Role of nitric oxide in tumor progression: Lessons from experimental tumors", Cancer and Metastatis Reviews, 17(1):91-106. 1998.

Golub et al., "Molecular Classification of Cancer Class Discovery and Class Prediction by Gene Expression Monitoring", Science, 286:531-537. 1999.

RN 1326924-17-7, Database Registry [Online], Sep. 2, 2011, Retrieved from STN.

RN 1326900-40-6, Database Registry [Online], Sep. 2, 2011, Retrieved from STN.

RN 1326894-16-9, Database Registry [Online], Sep. 2, 2011, Retrieved from STN.

RN 1326879-96-2, Database Registry [Online], Sep. 2, 2011, Retrieved from STN.

RN 1115976-39-0, Database Registry [Online], Mar. 5, 2009, Retrieved from STN.

RN 1115976-35-6, Database Registry [Online], Mar. 5, 2009, Retrieved from STN.

RN 1115905-70-8, Database Registry [Online], Mar. 5, 2009, Retrieved from STN.

RN 1115905-69-5, Database Registry [Online], Mar. 5, 2009, Retrieved from STN.

RN 1115905-67-3, Database Registry [Online], Mar. 5, 2009, Retrieved from STN.

Large, Charles H., et al., "The relationship between sodium channel inhibition and anticonvulsant activity in a model of generalized seizure in the rat", Epilepsy Research, 85:96-106. 2009.

Hussein, Z. et al., "Pharmacokinetics of 619C89, a novel neuronal sodium channel inhibitor, in acute stroke patients after loading and discrete maintenance infusions", British Journal of Clinical Pharmacology, 41(6):505-511. 1996.

Palmer, Alan M., et al., "The role of sodium channels in disease", Drug News & Perspectives, 14(9):568-576. 2001.

Tsutsumi et al., "Off-target inhibition by active site-targeting SHP2 inhibitors", FEBS Open Bio, 8:1405-1411. 2018.

Cancer [online], [retrieved on Jul. 6, 2007]. Retrieved from the internet, URL http://www.nlm.nih.gov/medlineplus/cancer.html.

COMPOUNDS AND COMPOSITIONS FOR INHIBITING THE ACTIVITY OF SHP2

SEQUENCE LISTING

The instant application contains a Sequence Listing which has been filed electronically in ASCII format and is hereby incorporated by reference in its entirety. Said ASCII copy, created on Mar. 8, 2019, is named PAT057289-US-PCT_SL.txt and is 1,126 bytes in size.

BACKGROUND

Field of the Invention

The present invention relates to compounds capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

Background of the Invention

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present invention fulfill the need of small molecules to that inhibit the activity of SHP2.

SUMMARY OF THE INVENTION

In one aspect, the present invention provides compounds of Formula I:

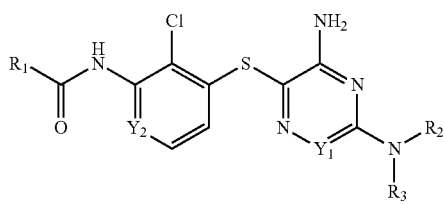

I

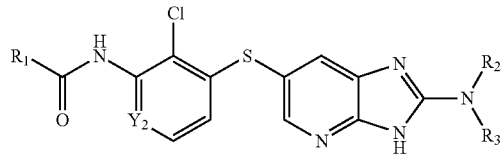

II in which:

$R_1$ is selected from:

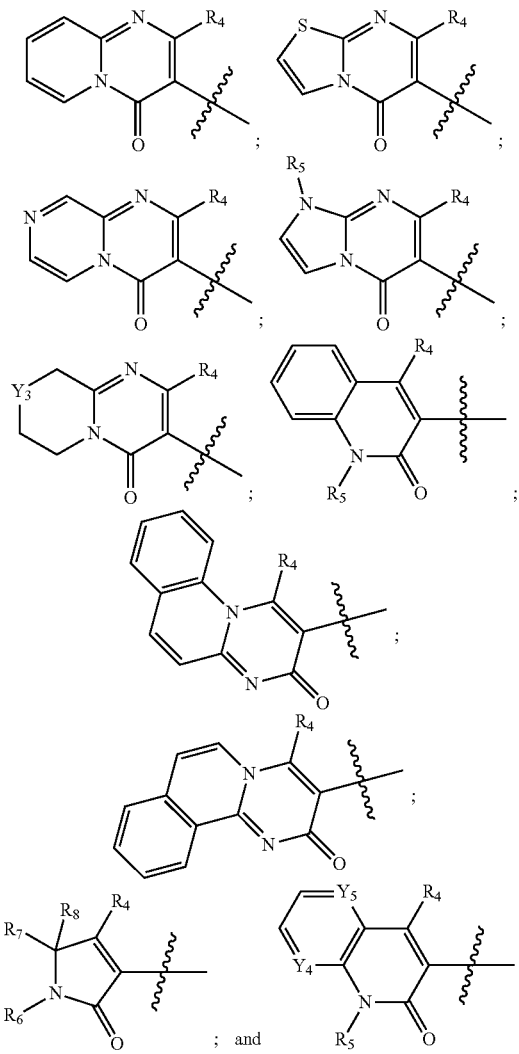

$R_2$ and $R_3$ together with the nitrogen to which both $R_2$ and $R_3$ are attached form a ring selected from piperidinyl, piperazinyl, 2-oxa-8-azaspiro[4.5]decan-8-yl, 8-azaspiro[4.5]decan-8-yl and pyrrolidinyl; wherein said pyrrolidinyl, piperazinyl, 2-oxa-8-azaspiro[4.5]decan-8-yl, 8-azaspiro[4.5]decan-8-yl or piperidinyl is unsubstituted or substituted with 1 to 3 groups independently selected from amino, methyl, ethyl, amino-methyl, methyl-amino, hydroxyl, cyano, fluoro-methyl, fluoro and (((((5-methyl-2-oxo-1,3-dioxol-4-yl)methoxy)carbonyl)amino)methyl; $R_4$ is selected from hydroxyl, $C_{1-3}$alkoxy and $OC(O)C_{1-3}$alkyl; $R_5$ is selected from H and methyl; $R_6$ is selected from hydrogen, methyl and phenyl; $R_7$ is selected from hydrogen, methyl, ethyl, phenyl and benzyl; $R_8$ is selected from hydrogen and methyl; $Y_1$ is selected from N and CH; $Y_2$ is selected from N and CH; $Y_3$ is selected from NH and $CH_2$; $Y_4$ is selected from N and CH; $Y_5$ is selected from N and CH; or a pharmaceutically acceptable salt thereof.

In a second aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In a third aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof, in simultaneous or sequential combination with an anticancer therapeutic.

In a fifth aspect, the present invention provides the use of a compound of Formula I in the manufacture of a medicament for treating a disease in an animal in which SHP2 activity contributes to the pathology and/or symptomology of the disease.

In a sixth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, cyclohexenyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60R, D61Y, V, N; Y62D; E69K; A72T, V; T73I; E76K, V, G, A, Q; E139D; G503A, R; Q506P (JMML); G60V; D61V; E69K; F71L; A72V; E76A (MDS); Y63C (CMML); Y62C; E69K; T507K (neuroblastoma); V46L; N58S; E76V (Lung cancer); R138Q (melanoma); E76G (colon cancer).

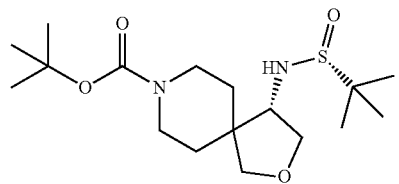 [SMILES: CC(C)(C)OC(=O)N1CCC2(CC1)COC[C@H]2N[S@](=O)C(C)(C)C]

For the instant application, the above structure is represented by (S)-tert-butyl 4-((R)-1,1-dimethylethylsulfinamido)-2-oxa-8-azaspiro[4.5]decane-8-carboxylate (name generated by chemdraw) and (S)-tert-butyl 4-((R)-1,1-dimethylethylsulfinamino)-2-oxa-8-azaspiro[4.5]decane-8-carboxylate (name recognized by chemdraw).

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(=Z-) or trans (=E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

DESCRIPTION OF PREFERRED EMBODIMENTS

The present invention relates to compounds capable of inhibiting the activity of SHP2. In one aspect of the invention, with respect to compounds of formula I & II, are compounds of formula II:

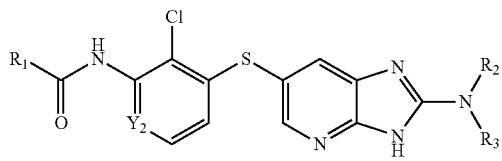

in which: $R_1$ is selected from:

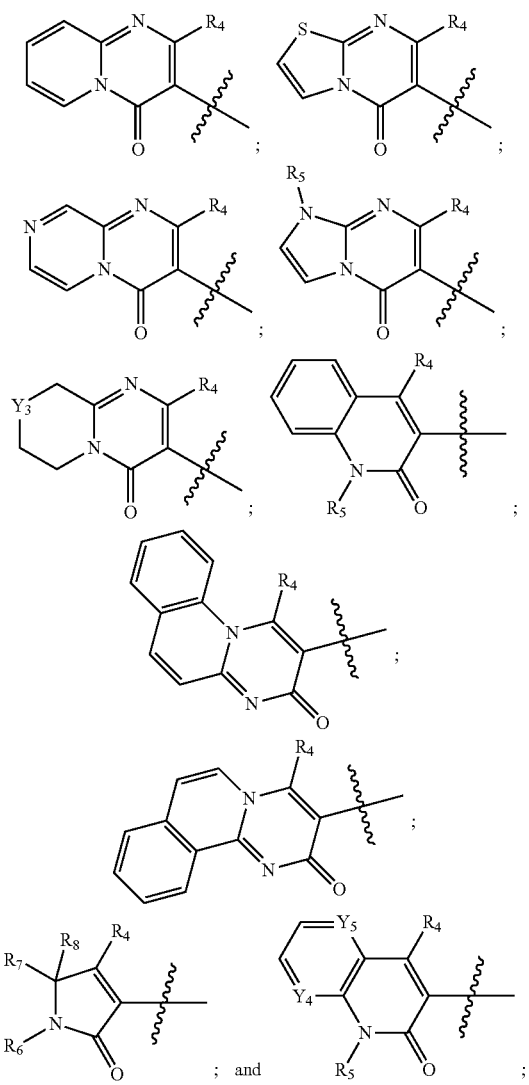

$R_2$ and $R_3$ together with the nitrogen to which both $R_2$ and $R_3$ are attached form a ring selected from piperidinyl, piperazinyl, 2-oxa-8-azaspiro[4.5]decan-8-yl, 8-azaspiro[4.5]decan-8-yl and pyrrolidinyl; wherein said pyrrolidinyl, piperazinyl, 2-oxa-8-azaspiro[4.5]decan-8-yl, 8-azaspiro[4.5]decan-8-yl or piperidinyl is unsubstituted or substituted with 1 to 3 groups independently selected from amino, methyl, ethyl, amino-methyl, methyl-amino, hydroxyl, cyano, fluoro-methyl, fluoro and ((((5-methyl-2-oxo-1,3-dioxol-4-yl)methoxy)carbonyl)amino)methyl; $R_4$ is selected from hydroxyl; $R_5$ is selected from H and methyl; $R_6$ is selected from hydrogen, methyl and phenyl; $R_7$ is selected from hydrogen, methyl, ethyl, phenyl and benzyl; $R_8$ is selected from hydrogen and methyl; $Y_1$ is selected from N and CH; $Y_2$ is selected from N and CH; $Y_3$ is selected from NH and CH$_2$; $Y_4$ is selected from N and CH; $Y_5$ is selected from N and CH; or a pharmaceutically acceptable salt thereof.

In a further embodiment are compounds, or the pharmaceutically acceptable salt thereof, in which: R₁ is selected from:

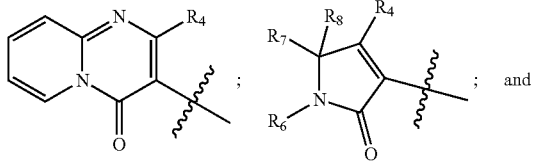 ; 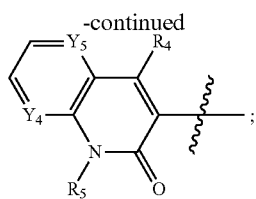 ;

and $R_4$ is selected from hydroxyl; $R_5$ is selected from H and methyl; $R_6$ is selected from hydrogen, methyl and phenyl; $R_7$ is selected from hydrogen, methyl, ethyl, phenyl and benzyl; $R_8$ is selected from hydrogen and methyl; $Y_4$ is selected from N and CH; and $Y_5$ is selected from N and CH.

In a further embodiment are compounds, or a pharmaceutically acceptable salt thereof, selected from:

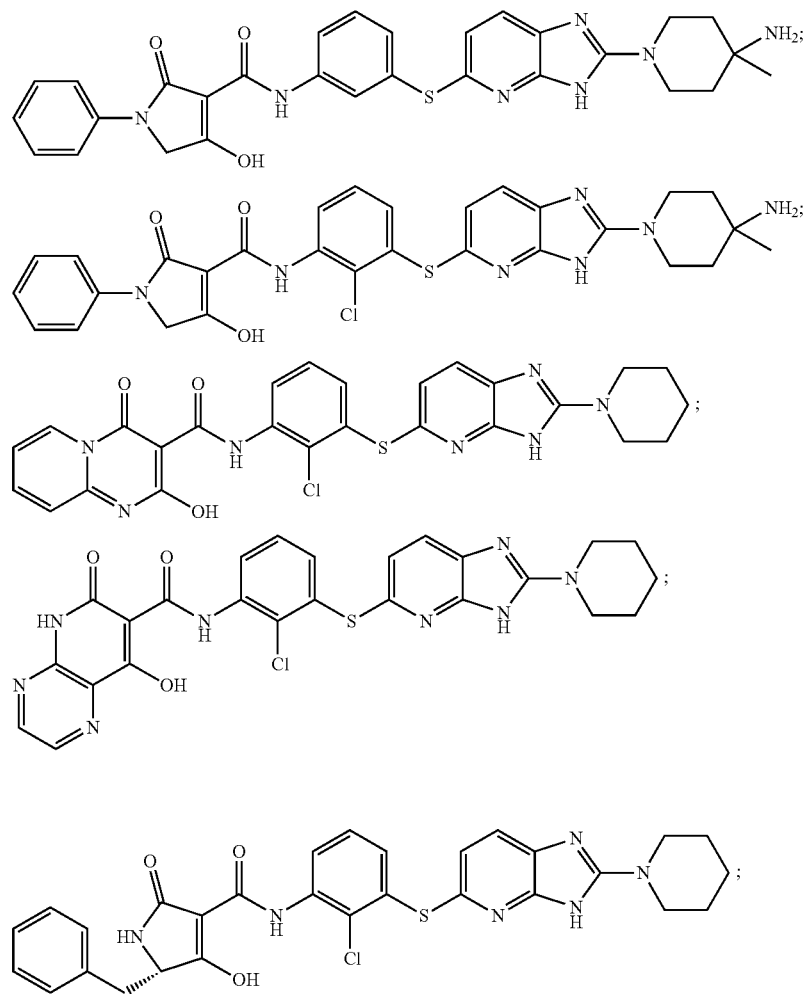

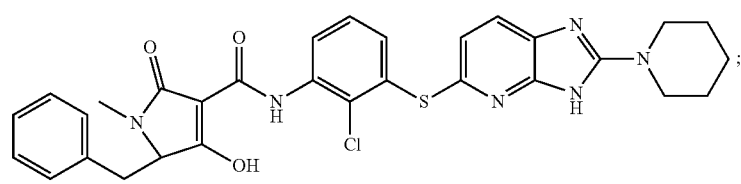

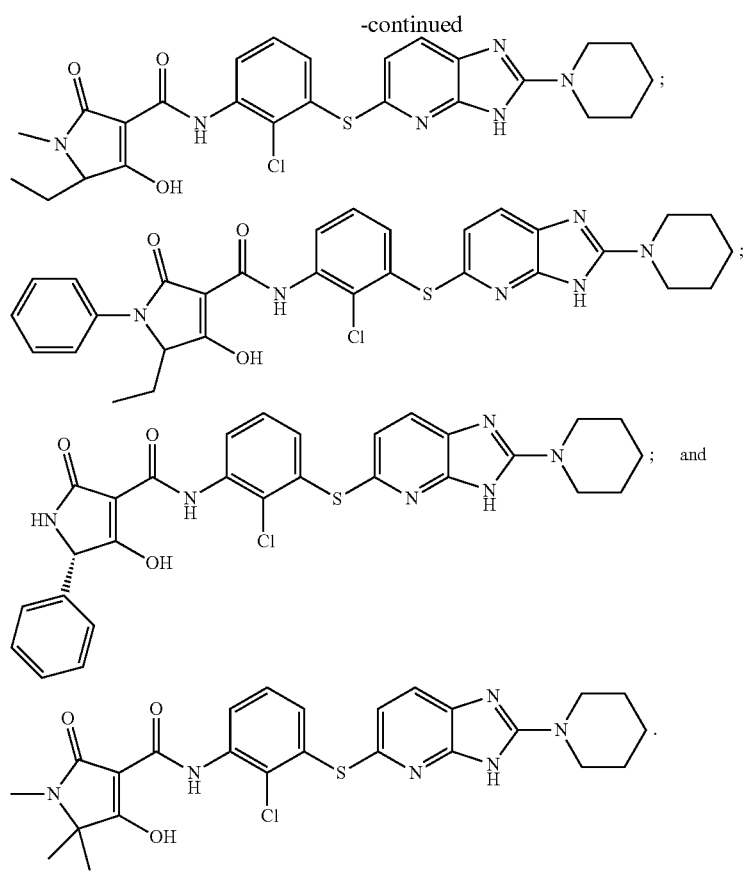
In another embodiment are compounds of formula I:
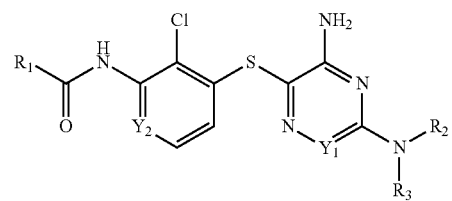
I
in which: R₁ is selected from:
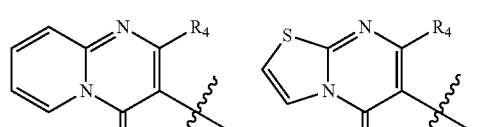
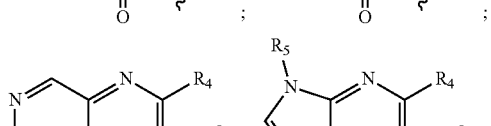
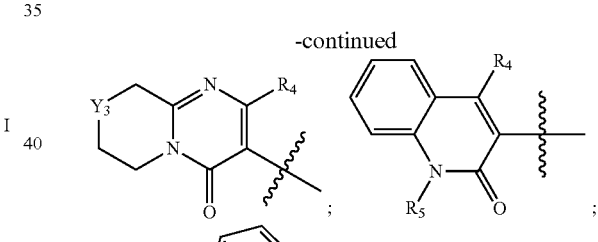
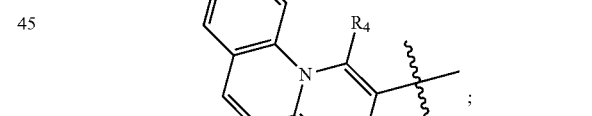
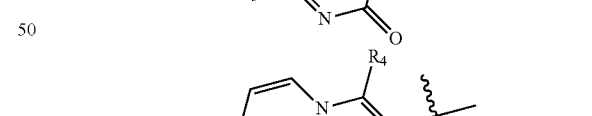
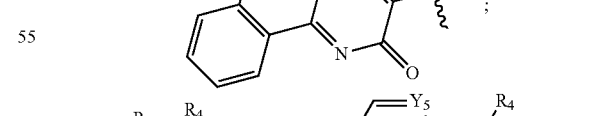
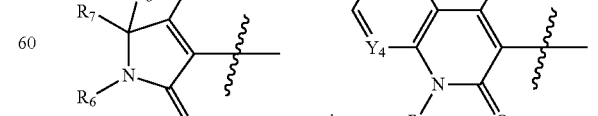
R₂ and R₃ together with the nitrogen to which both R₂ and R₃ are attached form a ring selected from piperidinyl, piperazinyl, 2-oxa-8-azaspiro[4.5]decan-8-yl, 8-azaspiro[4.5]decan-8-yl and pyrrolidinyl; wherein said pyrrolidinyl, piperazinyl, 2-oxa-8-azaspiro[4.5]decan-8-yl, 8-azaspiro[4.5]decan-8-yl or piperidinyl is unsubstituted or substituted with 1 to 3 groups independently selected from amino, methyl, ethyl, amino-methyl, methyl-amino, hydroxyl, cyano, fluoro-methyl, fluoro and (((((5-methyl-2-oxo-1,3-dioxol-4-yl)methoxy)carbonyl)amino)methyl; $R_4$ is selected from hydroxyl; $R_5$ is selected from H and methyl; $R_6$ is selected from hydrogen, methyl and phenyl; $R_7$ is selected from hydrogen, methyl, ethyl, phenyl and benzyl; $R_8$ is selected from hydrogen and methyl; $Y_1$ is selected from N and CH; $Y_2$ is selected from N and CH; $Y_3$ is selected from NH and $CH_2$; $Y_4$ is selected from N and CH; $Y_5$ is selected from N and CH; or a pharmaceutically acceptable salt thereof.

In a further embodiment are compounds, or the pharmaceutically acceptable salt thereof, selected from:

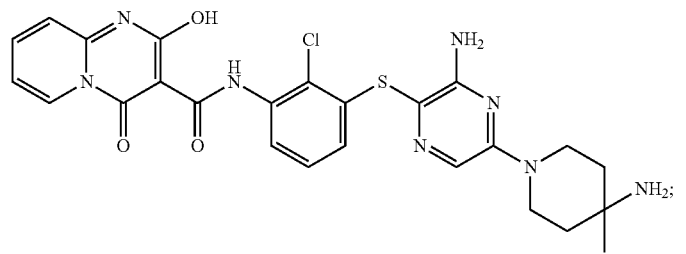

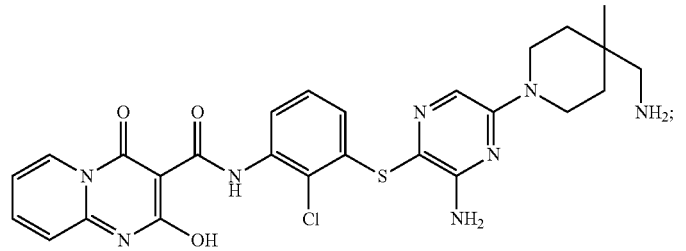

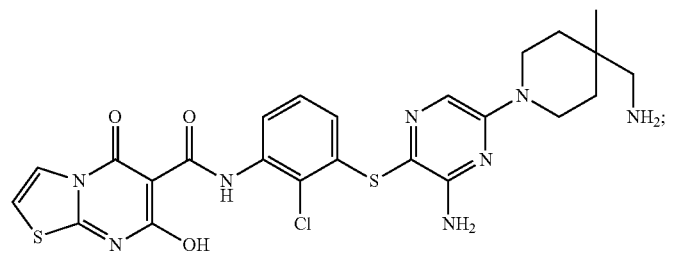

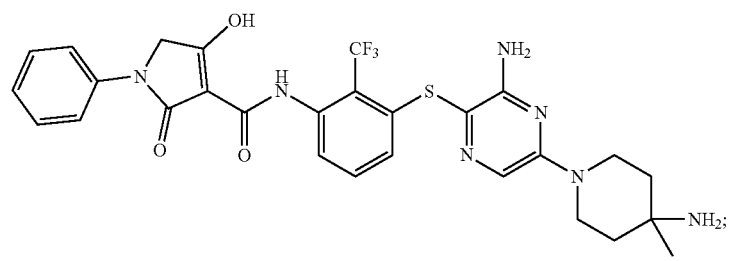

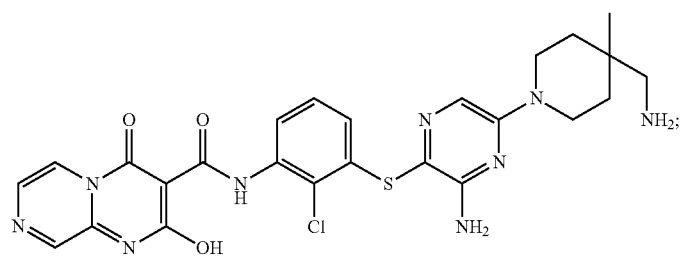

-continued
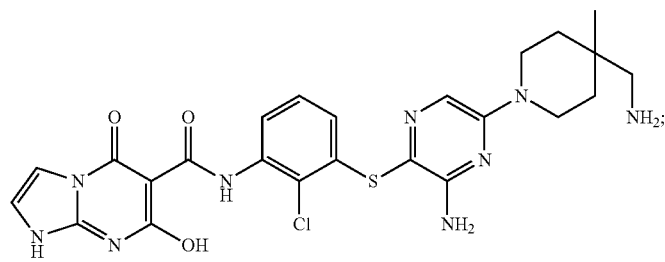
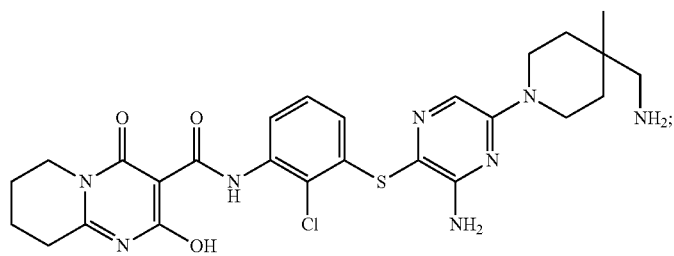
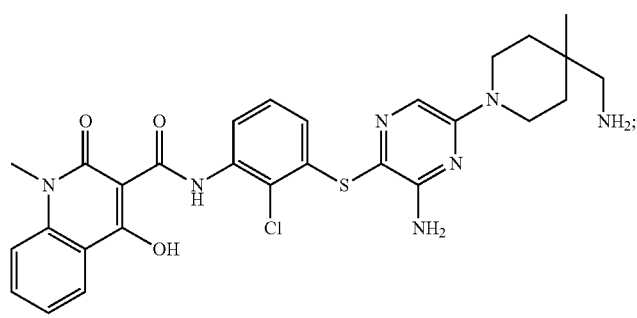
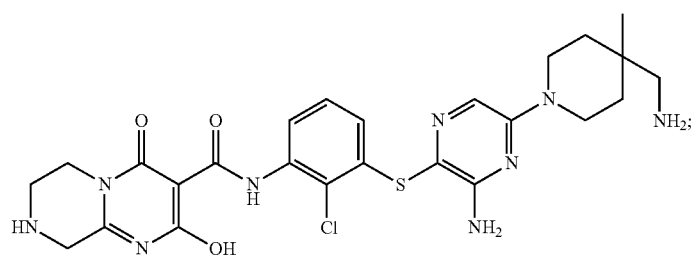
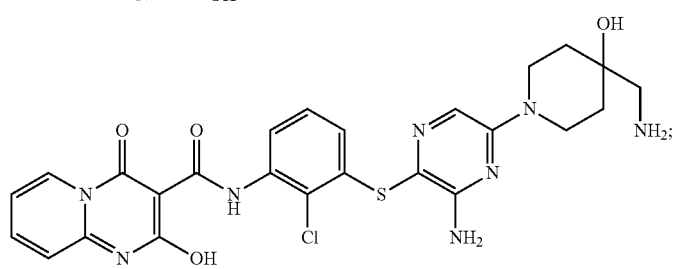
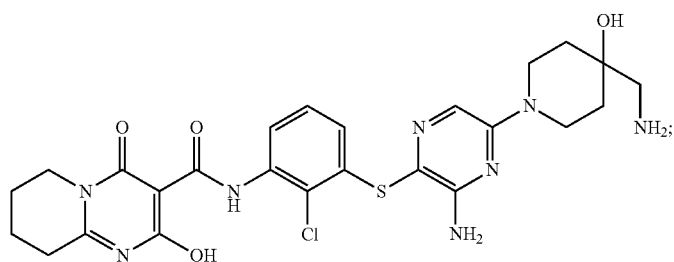

-continued
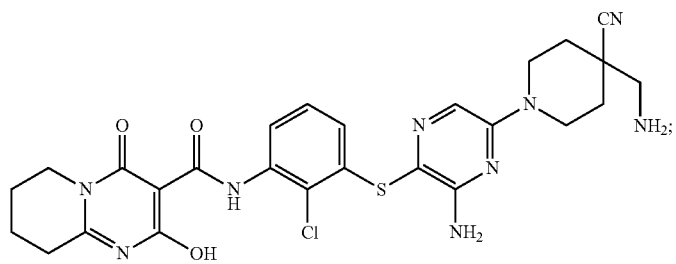
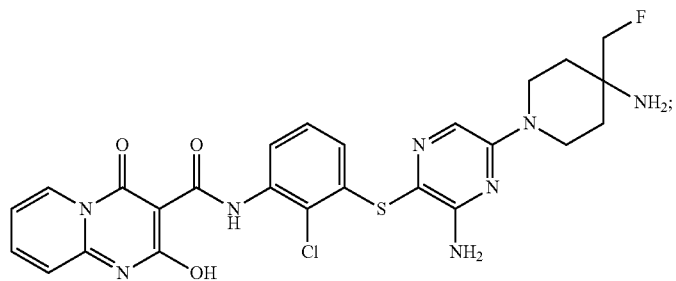
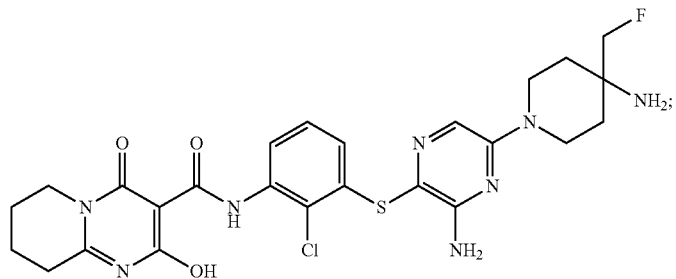
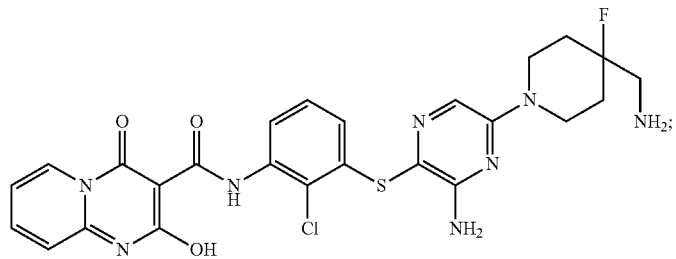
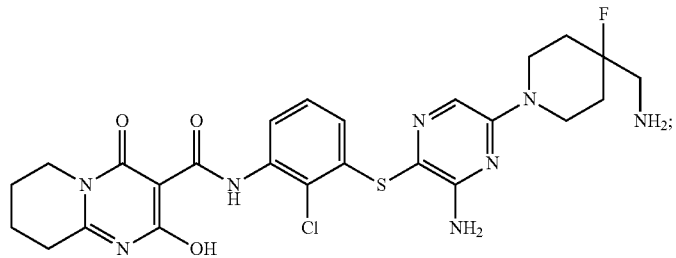
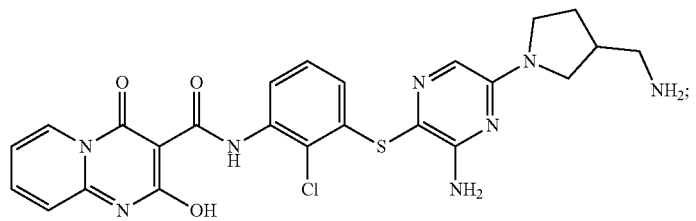

-continued
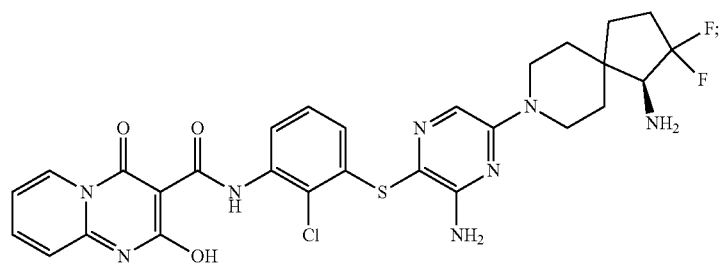
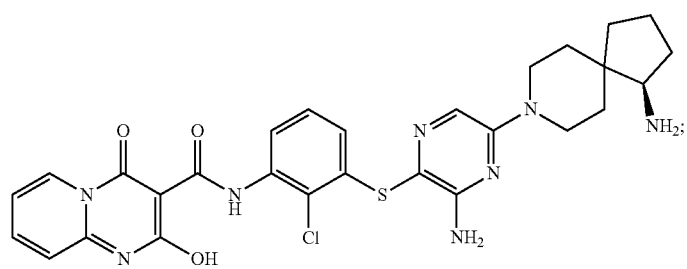
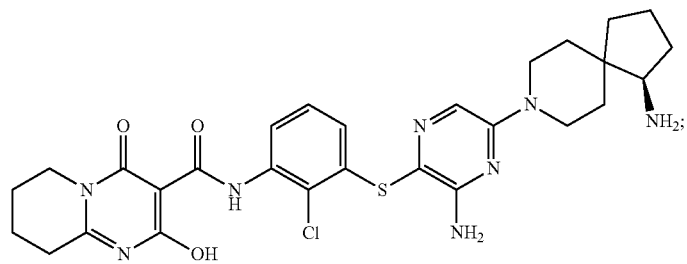
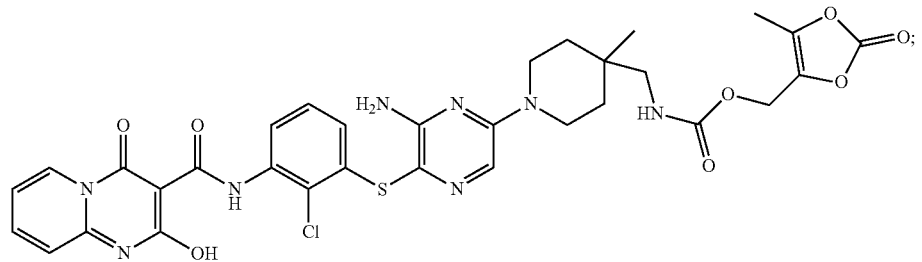
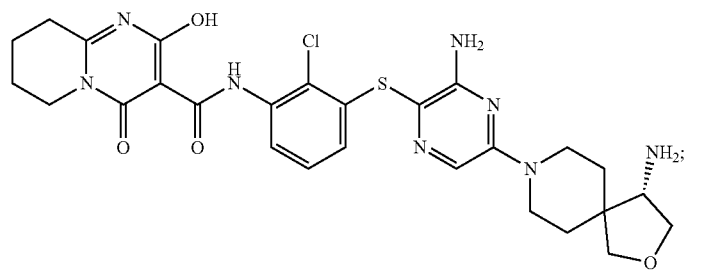
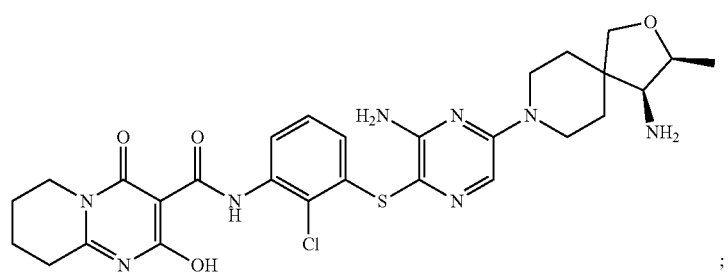

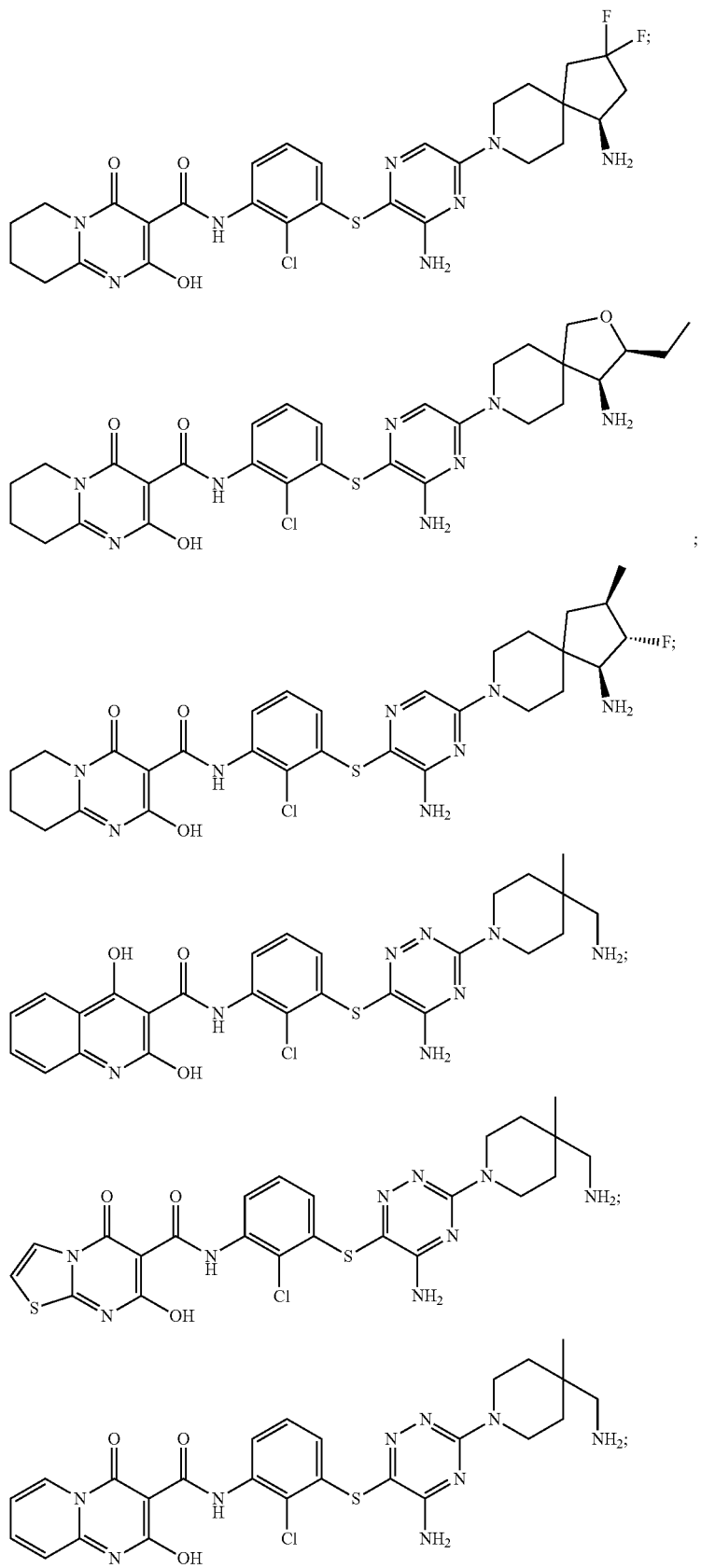

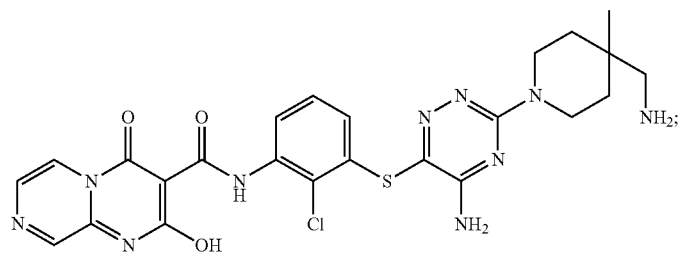
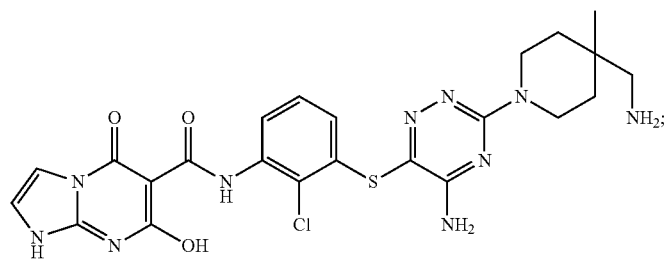
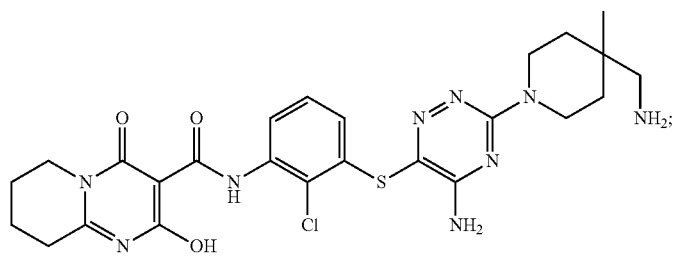
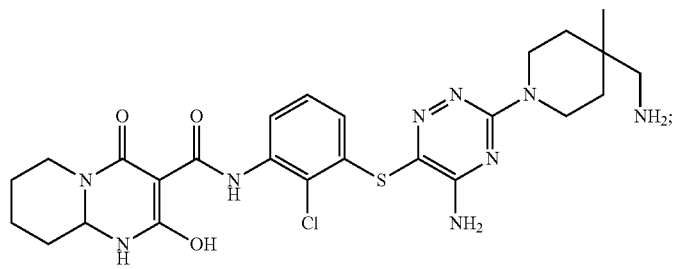
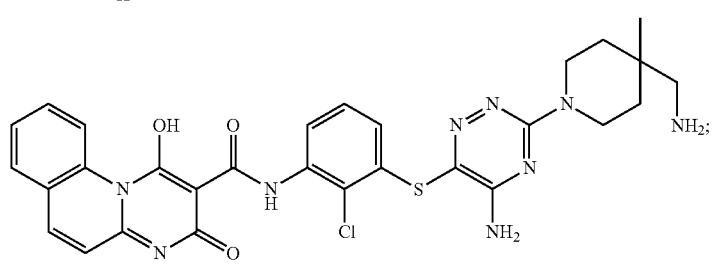
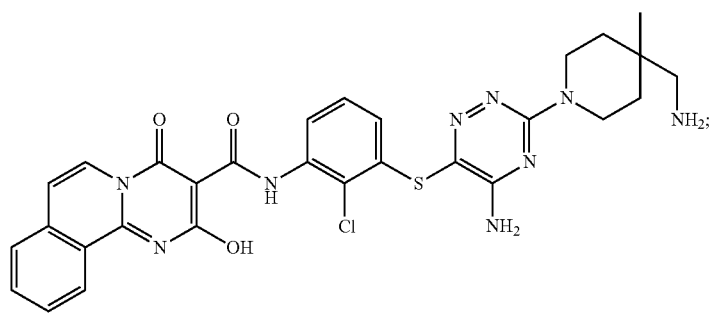

-continued
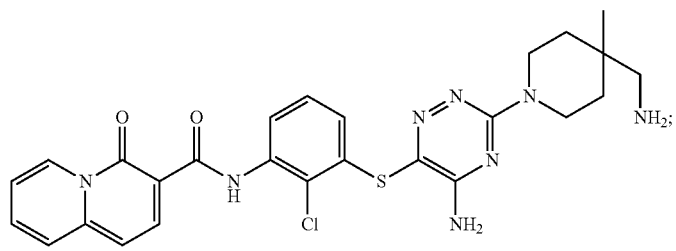
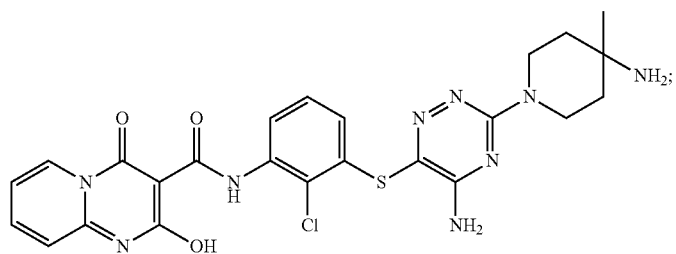
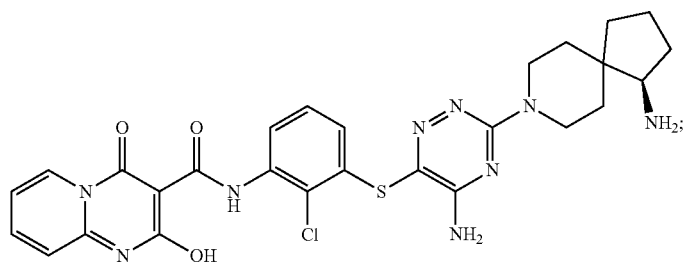
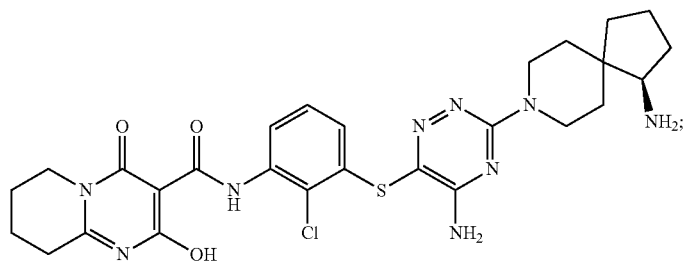
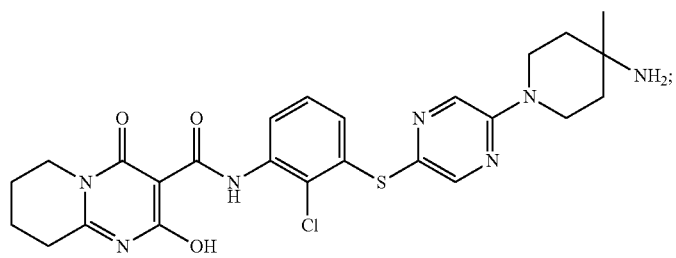
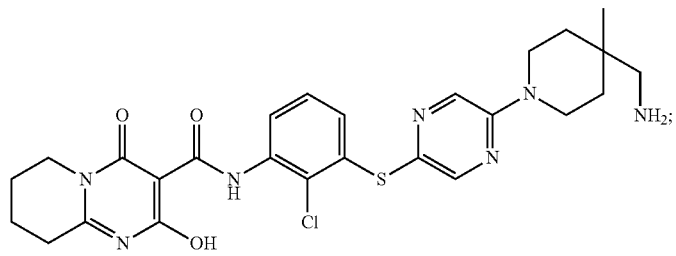

-continued
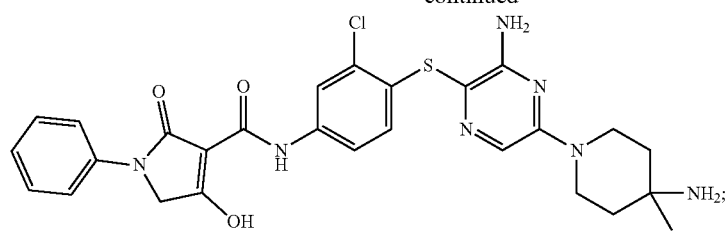
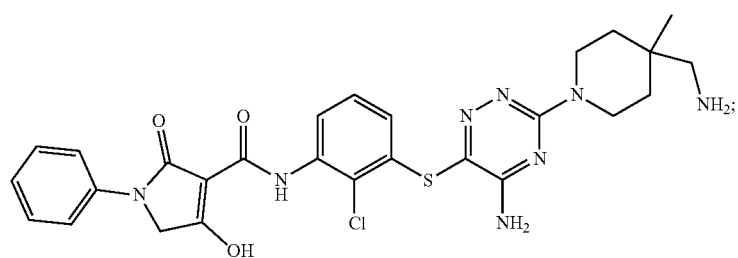
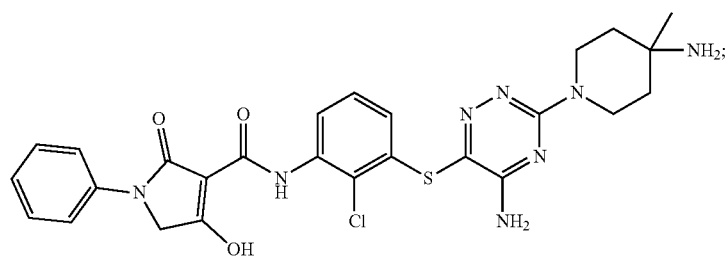
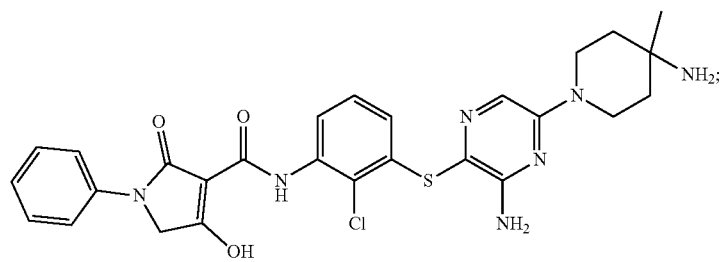
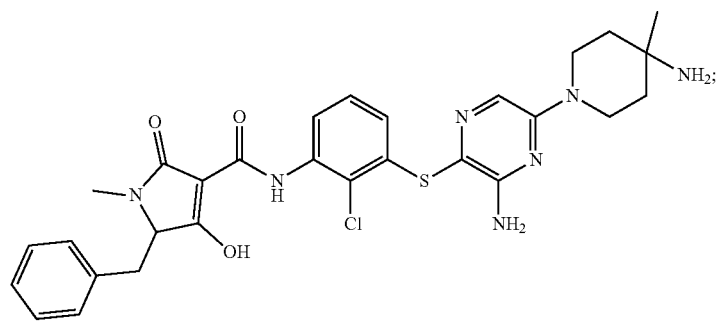
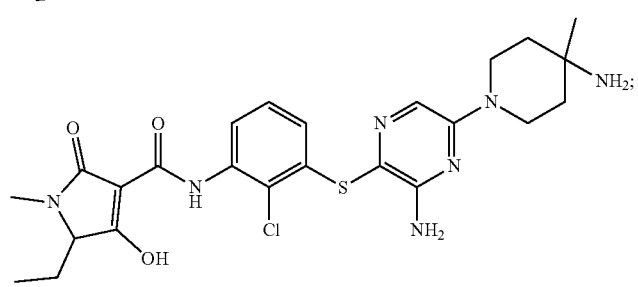

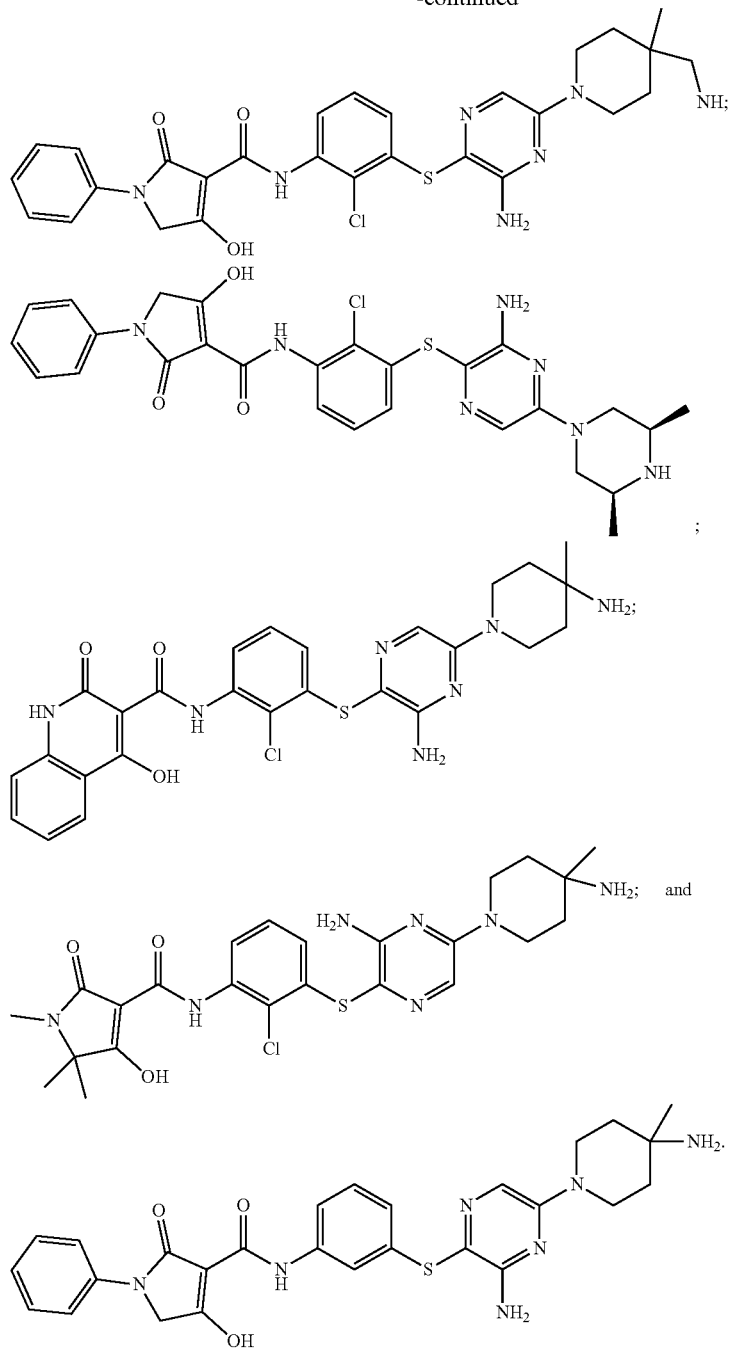

Pharmacology and Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS)—PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML)—Somatic mutations in PTPN11 (SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N—SH2 domain, resulting in SHP2 activity.

Acute Myeloid Leukemia—PTPN11 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR$^{amp}$, Her2$^{amp}$, FGFR$^{amp}$, Met$^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastic Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary of the Invention.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemothereutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

A compound of formula (I) can also be used in combination with the following compounds and antibody-drug conjugates:

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3).

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705A; and CH5424802.

BRAF inhibitors: Vemurafanib (PLX4032); and Dabrafenib.

FLT3 inhibitors—sunitinib malate (sold under the tradename Sutent® by Pfizer); PKC412 (midostaurin); tanutinib, sorafenib, sunitinib, midostaurin, lestaurtinib, KW-2449, quizartinib (AC220) and crenolanib.

MEK Inhibitors—trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxypurin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc);

Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®;

Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-$N^2$-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®);

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

A compound of formula (I) can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

Reaction Scheme I:

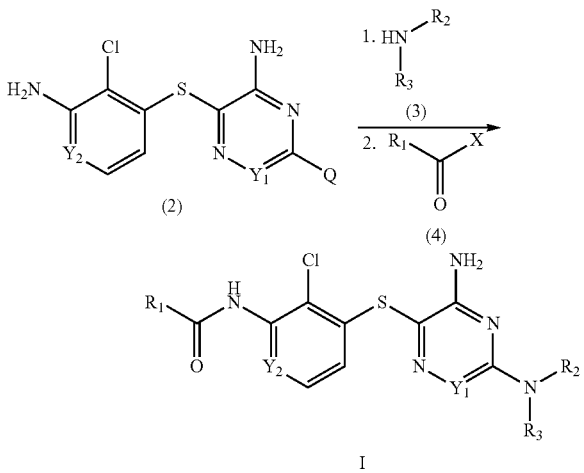

in which Q is a leaving group and $Y_1$, $Y_2$, $R_1$, $R_2$ and $R_3$ are as defined by the Summary of the Invention. Compounds of formula I can be prepared by reacting a compound of formula 2 with a compound of formula 3 in the presence of a suitable base (for example, DIPEA, or the like) and a suitable solvent (for example DMSO, NMP, or the like). The reaction proceeds at a temperature range of about 80° C. to about 140° C. and can take from about 1 hour to about 24 hours to complete. Further reaction with a compound of formula 4 with a suitable leaving group X can proceed in a suitable solvent at elevated temperature in the presence or absence of a base. These processes may occur with the use of suitable protecting groups which may later be removed and the steps may occur in reverse order.

Compounds of Formula II can be prepared by proceeding as in the following Reaction Scheme II:

Reaction Scheme II:

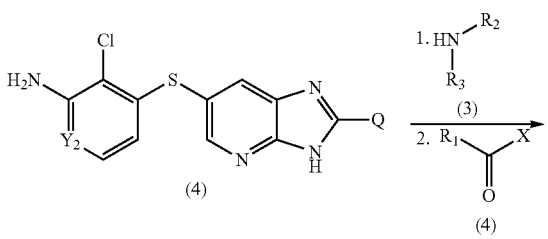

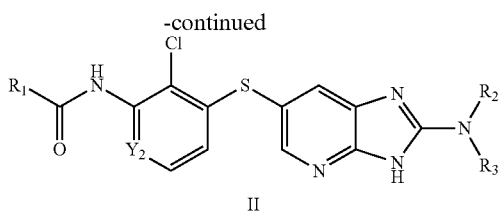

II in which Q is a leaving group and $Y_1$, $Y_2$, $R_1$, $R_2$ and $R_3$ are as defined by the Summary of the Invention. Compounds of formula II can be prepared by reacting a compound of formula 4 with a compound of formula 3 in the presence of a suitable base (for example, DIPEA, or the like) and a suitable solvent (for example DMSO, NMP, or the like). The reaction proceeds at a temperature range of about 80° C. to about 140° C. and can take from about 1 hour to about 24 hours to complete. Further reaction with a compound of formula 4 with a suitable leaving group X can proceed in a suitable solvent at elevated temperature in the presence or absence of a base. These processes may occur with the use of suitable protecting groups which may later be removed and the steps may occur in reverse order.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkyl-carbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley and Sons, Inc., 1981.

In summary, the compounds of Formula I can be made by a process, which involves:
(a) that of reaction schemes I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof. Some abbreviations used in the examples are as follows: acetic acid (AcOH); acetonitrile (MeCN); triethylamine (TEA); tetrahydrofuran (THF); aqueous (aq.); atmosphere (atm.); 2,2'-bis-diphenylphosphanyl-[1,1']binaphthalenyl (BINAP); 4-dimethylaminopyridine (DMAP); tert-butoxycarbonyl (Boc); 1,1-carbonyldiimidazole (CDI); di-tert-butyl dicarbonate (Boc$_2$O); benzotriazole-1-yl-oxy-tris-(dimethylamino)-phosphonium hexafluorophosphate (BOP); dichloromethane (DCM); diethyl ether (Et$_2$O); p-toluene sulfonic acid (PTSA); ethyl acetate (EtOAc); ethanol (EtOH); lithium bis(trimethylsilyl)amide (LHMDS); diisopropyl azodicarboxylate (DIAD); N,N-diisopropyl-ethylamine (DIEA or DIPEA); N,N-dimethylformamide (DMF); dimethyl sulfoxide (DMSO); diphenylphosphoryl azide (DPPA); hour(s) (h); 2-(1H-7-azabenzotriazol-1-yl)-1,1,3,3-tetramethyluronium hexafluorophosphate (HATU); High Performance Liquid Chromatography (HPLC); isopropyl alcohol (IPA); lithium aluminium hydride (LAH); liquid chromatography coupled with mass spectrometry (LCMS); lithium diisopropylamide (LDA); methanol (MeOH); milliliter(s) (mL); minute(s) (min); microwave (MW); sodium bis(trimethylsilyl)amide (NHMDS); n-butyllithium (n-BuLi); 1,1-bis(diphenylphosphino)-ferrocenedichloropalladium (II) (PdCl$_2$(dppf)); tris(dibenzylideneacetone) dipalladium (0) (Pd$_2$(dba)$_3$); dichlorobis(triphenylphosphine)palladium (II) (PdCl$_2$(PPh$_3$)$_2$); room temperature (RT); tetra-n-butylammonium fluoride (TBAF); tert-butyldimethylsilyl chloride (TBSCl); trifluoroacetic acid (TFA); tetrahydrofuran (THF); thin layer chromatography (TLC); retention time (T$_R$); (S)-(−)-2,2'-Bis(di-p-tolylphosphino)-1, 1'-binaphthyl ((S)-TolBINAP); & 4,5-bis(diphenylphosphino)-9,9-dimethylxanthene (XantPhos).

Intermediate 1 tert-Butyl ((1-(6-amino-5-((3-amino-2-chlorophenyl) thio)pyrazin-2-yl)-4-methylpiperidin-4-yl)methyl) carbamate

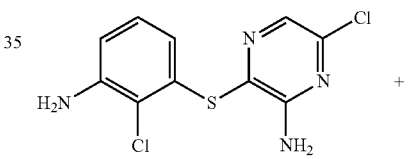

+

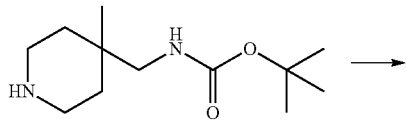

→

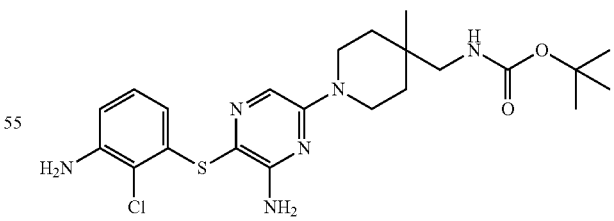

As described for Example 1, a similar procedure was performed using 3-((3-amino-2-chlorophenyl)thio)-6-chloropyrazin-2-amine (1.5 g, 5.2 mmol) and tert-butyl ((4-methylpiperidin-4-yl)methyl)carbamate (1.9 g, 8.4 mmol) to give tert-butyl ((1-(6-amino-5-((3-amino-2-chlorophenyl) thio)pyrazin-2-yl)-4-methylpiperidin-4-yl)methyl)carbamate (2.4 g). MS m/z 479.3 (M+H)$^+$.

Intermediate 2

Methyl 2-hydroxy-4-oxo-6,7,8,9-tetrahydro-4H-pyrido[1,2-a]pyrimidine-3-carboxylate

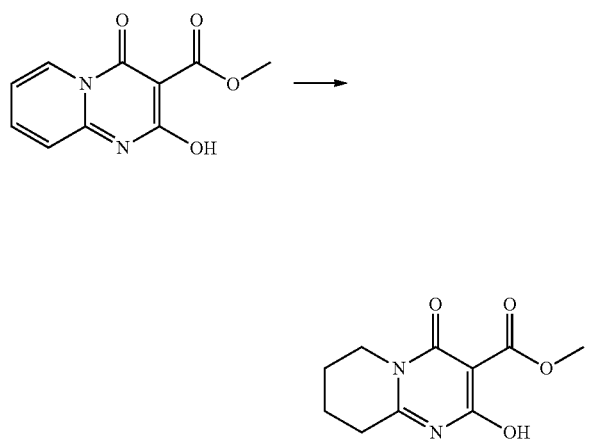

To a solution of methyl 2-hydroxy-4-oxo-4H-pyrido[1,2-a]pyrimidine-3-carboxylate (2 g, 9.08 mmol) in MeOH (50 mL) was added 10% Pd/C (1.9 g, 1.8 mmol). The reaction mixture was stirred at RT under an H$_2$ atmosphere (balloon) for 2.5 h. After this time the reaction mixture was filtered through Celite® and concentrated under reduced pressure to dryness giving the titled compound (2.15 g). MS m/z 225.1 (M+H)$^+$.

Intermediate 3

Ethyl 2-hydroxy-4-oxo-4,6,7,8,9,9a-hexahydro-1H-pyrido[1,2-a]pyrimidine-3-carboxylate

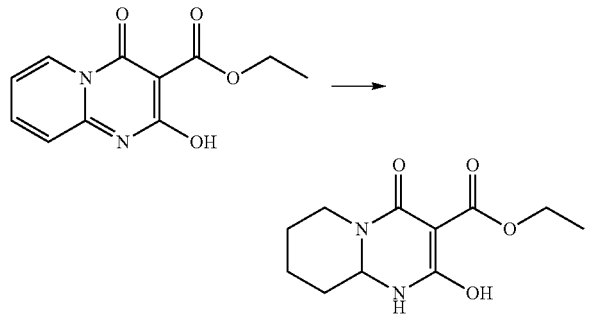

To a solution of ethyl 2-hydroxy-4-oxo-4H-pyrido[1,2-a]pyrimidine-3-carboxylate (0.05 g, 0.21 mmol) in MeOH (1 mL) was added 10% Pd/C (0.045 g, 0.04 mmol). The reaction mixture was stirred overnight at RT under an H$_2$ atmosphere (balloon). After this time the reaction mixture was filtered through Celite® and concentrated under reduced pressure to dryness to give ethyl 2-hydroxy-4-oxo-1,6,7,8,9,9a-hexahydro-4H-pyrido[1,2-a]pyrimidine-3-carboxylate (0.043 g). MS m/z 241.1 (M+H)$^+$.

Intermediate 4

8-tert-Butyl 3-ethyl 2-hydroxy-4-oxo-6,7-dihydro-4H-pyrazino[1,2-a]pyrimidine-3,8(9H)-dicarboxylate

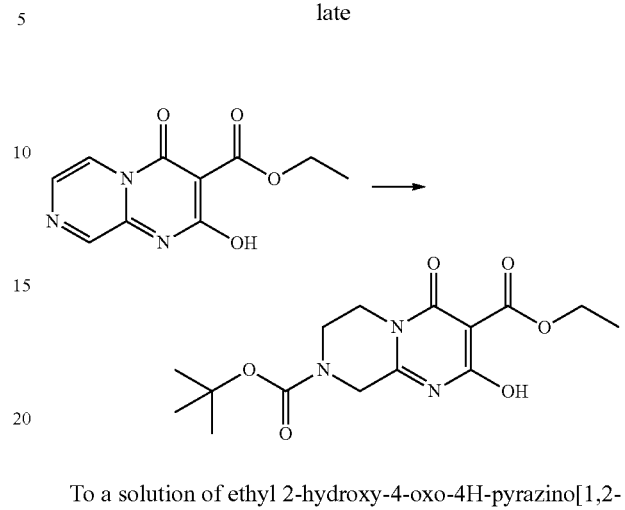

To a solution of ethyl 2-hydroxy-4-oxo-4H-pyrazino[1,2-a]pyrimidine-3-carboxylate (0.10 g, 0.44 mmol) in MeOH (5 mL) was added Pd/C (10%, 0.09 g, 0.09 mmol), Boc$_2$O (0.15 mL, 0.66 mmol) and DIPEA (0.23 mL, 1.31 mmol). The reaction mixture was stirred at RT under an H$_2$ atmosphere (balloon) for 1 h. The reaction mixture was filtered through a Celite® plug and concentrated under reduced pressure to dryness. The residue was purified by flash silica chromatography (0-3% MeOH/DCM) to give the titled compound (0.072 g). MS m/z 340.2 (M+H)$^+$.

Intermediate 5 tert-Butyl (1-(6-amino-5-((3-amino-2-chlorophenyl)thio)pyrazin-2-yl)-4-(fluoromethyl)piperidin-4-yl)carbamate

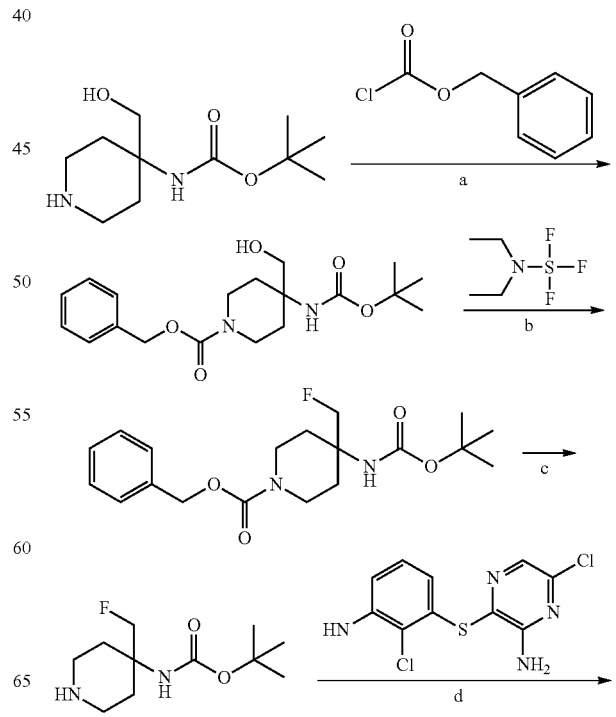

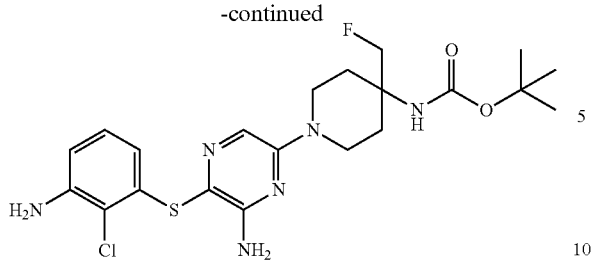

Step a: To suspension of tert-butyl (4-hydroxymethyl)piperidin-4-yl)carbamate (4.8 g, 20.8 mmol) in DCM (100 mL) at 0° C. was added triethylamine (8.7 mL, 6.3 g, 62.3 mmol) followed by benzyl chloroformate (5.3 g, 31.1 mmol). The reaction mixture was warmed to RT and stirred for 3 h. The reaction mixture was diluted with DCM (150 mL), the organic layer washed with water and brine, dried over $Na_2SO_4$, filtered, and concentrated under reduced pressure. The crude product was purified by silica chromatography (0-20% MeOH/DCM) to give 4.6 g of benzyl 4-((tert-butoxycarbonyl)amino)-4-(hydroxymethyl)piperidine-1-carboxylate. MS m/z 387.3 $(M+Na)^+$.

Step b: To solution of benzyl 4-((tert-butoxycarbonyl)amino)-4-(hydromethyl)piperidine-1-carboxylate (4.6 g, 12.6 mmol) in DCM (80 mL) at −78° C. was added dropwise diethylaminosulfur trifluoride (3.3 mL, 4.1 g, 25.2 mmol). The reaction mixture was stirred at −78° C. for 1 h and then warmed to RT over 30 min. The reaction mixture was diluted with DCM (200 mL), washed twice with sat. aq. $Na_2CO_3$, dried over $Na_2SO_4$, filtered and concentrated under reduced pressure to a cloudy yellow oil. The crude product was purified by silica chromatography (20-40% EtOAc/heptane) to give 1.9 g benzyl 4-((tert-butoxycarbonyl)amino)-4-(fluoromethyl)piperidine-1-carboxylate as a clear oil. MS m/z 367.1 $(M+H)^+$.

Step c: A suspension of benzyl 4-((tert-butoxycarbonyl)amino)-4-(fluoromethyl)piperidine-1-carboxylate (0.26 g, 0.71 mmol) and Pd/C (10%, 0.08 g) in MeOH (15 mL) was purged with N2 for 10 min and then stirred under an $H_2$ atmosphere (balloon) for 12 h at RT. The reaction mixture was filtered through a pad of Celite® with MeOH (100 mL). The combined organics were concentrated under reduced pressure to a clear oil to give tert-butyl (4-(fluoromethyl)piperidin-4-yl)carbamate (0.16 g). MS m/z 233.1 $(M+H)^+$.

Step d: As described for Example 1, a similar procedure was performed using 3-((3-amino-2-chlorophenyl)thio)-6-chloropyrazin-2-amine (0.37 g, 1.29 mmol) and tert-butyl (4-(fluoromethyl)piperidin-4-yl)carbamate (0.30 g, 1.29 mmol) to give the titled compound (0.26 g). MS m/z 483.1 $(M+H)^+$.

Intermediate 6 tert-Butyl ((1-(6-amino-5-((3-amino-2-chlorophenyl)thio)pyrazin-2-yl)-4-fluoropiperidin-4-yl)methyl)carboxylate

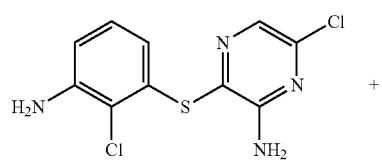

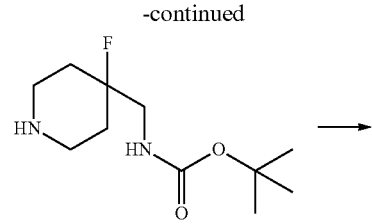

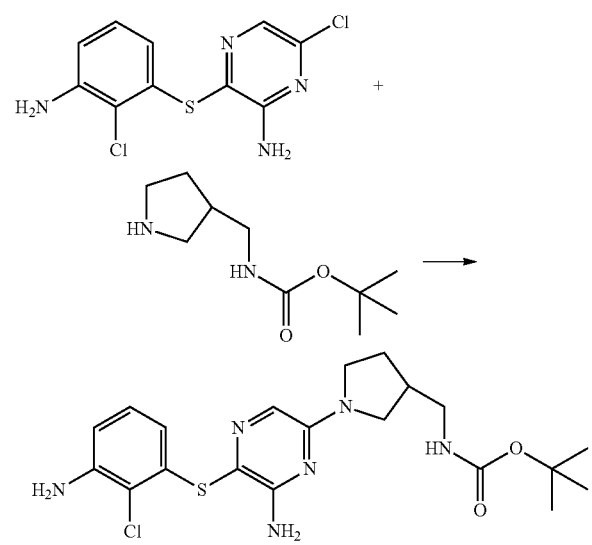

As described for Intermediate 1, a similar procedure was performed using 3-((3-amino-2-chlorophenyl)thio)-6-chloropyrazin-2-amine (0.2 g, 0.70 mmol) and tert-butyl ((4-fluoropiperidin-4-yl)methyl)carbamate (0.24 g, 1.05 mmol) to give the titled compound (0.29 g). MS m/z 483.1 $(M+H)^+$.

Intermediate 7 tert-Butyl ((1-(6-amino-5-((3-amino-2-chlorophenyl)thio)pyrazin-2-yl)pyrrolidin-3-yl)methyl)carbamate As described for Intermediate 1, a similar procedure was performed using 3-((3-amino-2-chlorophenyl)thio)-6-chloropyrazin-2-amine (0.20 g, 0.70 mmol) and tert-butyl (pyrrolidin-3-ylmethyl)carbamate (0.21 g, 1.05 mmol) to give the titled compound (0.19 g). MS m/z 451.1 $(M+H)^+$.

Intermediate 8 tert-Butyl ((1-(6-amino-5-((3-amino-2-chlorophenyl)thio)pyrazin-2-yl)pyrrolidin-3-yl)-2,2,2-trifluoroethyl)carboxylate

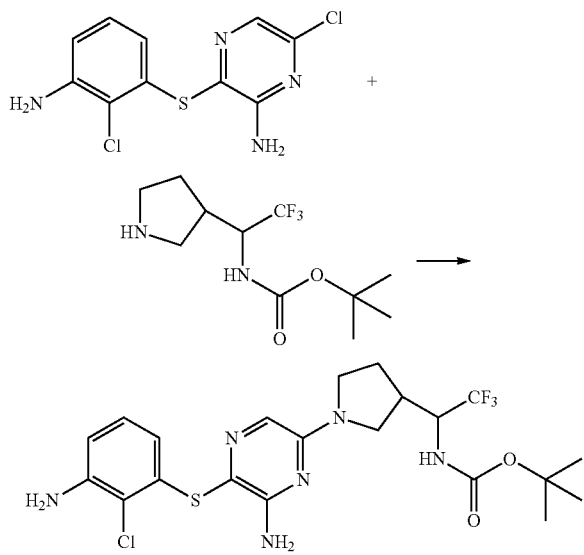

As described for Intermediate 1, a similar procedure was performed using 3-((3-amino-2-chlorophenyl)thio)-6-chloropyrazin-2-amine (0.20 g, 0.70 mmol) and tert-butyl (2,2,2-trifluoro-1-(pyrrolidin-3-yl)ethyl)carbamate (0.28 g, 1.05 mmol) to give the titled compound (0.29 g). MS m/z 519.2 (M+H)+.

Intermediate 9

3-((3-Amino-2-chlorophenyl)thio)-6-(4-amino-4-(trifluoromethyl)piperidin-1-yl)pyrazin-2-amine

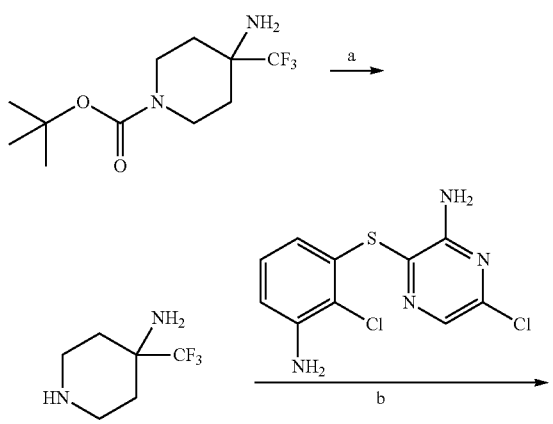

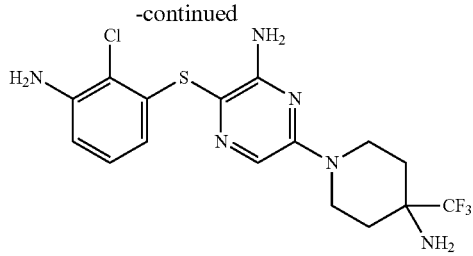

Step a: To a suspension of tert-butyl 4-amino-4-(trifluoromethyl)piperidine-1-carboxylate (0.50 g, 1.86 mmol) in dioxane (6 mL) and MeOH (1 mL) at RT was added 4 M HCl in dioxane (9.32 mmol, 2.3 mL). After stirring at RT for 16 h, the reaction mixture was concentrated under reduced pressure to a white solid (0.43 g), a bis-HCl salt. $^1$H NMR (400 MHz, DMSO-$d_6$) δ ppm 9.40-9.01 (m, 2H), 4.16 (br.s, 3H), 3.48 (d, J=11.5 Hz, 2H), 3.31 (d, J=12.1 Hz, 2H), 2.16 (t, J=10.9 Hz, 2H), 1.99 (d, J=14.1 Hz, 2H).

Step b: As described for Intermediate 2, a similar procedure was performed using 3-((3-amino-2-chlorophenyl)thio)-6-chloropyrazin-2-amine dihydrochloride (0.23 g, 0.80 mmol) and 4-(trifluoromethyl)piperidin-4-amine (0.25 g) to give the titled compound (0.32 g). MS m/z 419.3 (M+H)+.

Intermediate 10

5-((3-Amino-2-chlorophenyl)thio)-$N^2$-methyl-$N^2$-(2,2,6,6-tetramethylpiperidin-4-yl)pyrazine-2,6-diamine

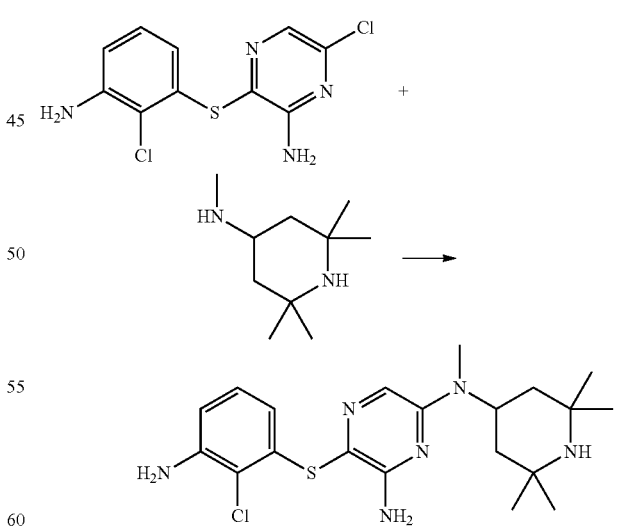

As described for Intermediate 1, a similar procedure was performed using 3-((3-amino-2-chlorophenyl)thio)-6-chloropyrazin-2-amine (0.29 g, 1.00 mmol) and N,2,2,6,6-pentamethylpiperidin-4-amine (0.51 g) to give the titled compound as the HCl salt (0.48 g). MS m/z 421.3 (M+H)+.

Intermediate 11

N—((S)-8-(6-Amino-5-((3-amino-2-chlorophenyl)thio)pyrazin-2-yl)-2,2-difluoro-8-azaspiro[4.5]decan-1-yl)-2-methylpropane-2-sulfinamide

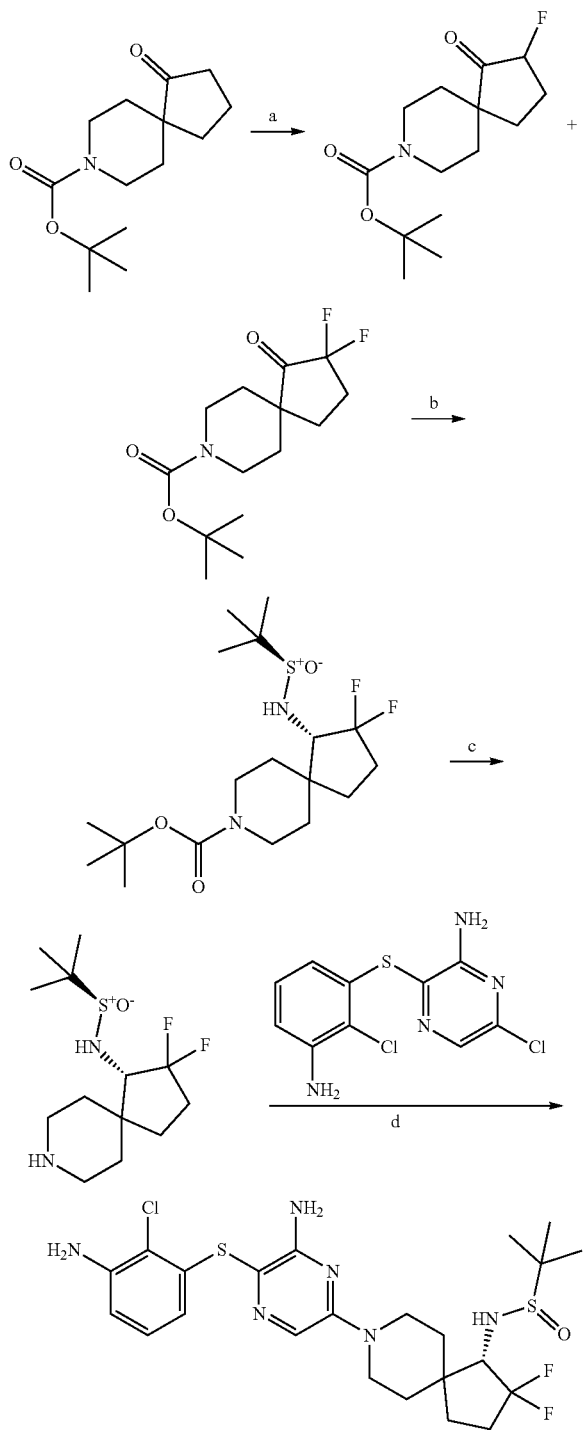

Step a: To a −78° C. solution of NaHMDS (1 M in THF, 8.68 mL, 8.68 mmol) was added a solution of tert-butyl 1-oxo-8-azaspiro[4.5]decane-8-carboxylate (2.0 g, 7.89 mmol) in THF (5 mL). After stirring for 30 min at this temperature, a solution of N-fluorobenzenesulfonamide (2.49 g, 7.89 mmol) in THF (10 mL) was added. After 3 h stirring at −78° C., the mixture was diluted with sat. aq. NaHCO$_3$ (100 mL) and extracted with DCM (3×100 mL). The combined organic phases were washed with brine, dried over Na$_2$SO$_4$, filtered, and concentrated under reduced pressure. The resulting residue was purified by silica chromatography (0-25% EtOAc/heptane) to give racemic tert-butyl 2-fluoro-1-oxo-8-azaspiro[4.5]decane-8-carboxylate (351 mg, 1.29 mmol). MS m/z 272.1 (M+H)$^+$. The difluoro ketone coeluted with starting material. The combined coeluted fractions of difluoro ketone/starting were repurified by silica chromatography (0-5% MeOH/DCM) to give tert-butyl2,2-difluoro-1-oxo-8-azaspiro[4.5]decane-8-carboxylate (573 mg). MS m/z 290.1 (M+H)$^+$.

Step b: To a 10 mL microwave vial containing tert-butyl 2,2-difluoro-1-oxo-8-azaspiro[4.5]decane-8-carboxylate (224 mg, 0.774 mmol) in THF (4 mL), was added solid (R)-2-methylpropane-2-sulfinamide (188 mg, 1.55 mmol) followed by neat titanium tetraethoxide (0.649 mL, 3.1 mmol). The reaction vessel was capped and heated at 90° C. for 1 h. The reaction mixture was cooled (0° C.) and LiBH$_4$ (34 mg, 1.6 mmol) was added directly to the THF solution. The reaction mixture stirred 30 min, then quenched by the slow addition of MeOH until frothing ceased. The reaction mixture was diluted with excess MeOH, then concentrated under reduced pressure with further addition of MeOH. The mixture was diluted with brine (with sonication) and extracted with EtOAc (4×10 mL), and the organics were concentrated under reduced pressure. Silica gel flash chromatography (0-50% EtOAc/heptane) afforded tert-butyl (S)-1-(((R)-tert-butylsulfinyl)amino)-2,2-difluoro-8-azaspiro[4.5]decane-8-carboxylate as a colorless oil which crystallized upon standing (180 mg), MS m/z 395.2 (M+H)$^+$.

Step c: To an ice cold solution of tert-butyl (S)-1-(((R)-tert-butylsulfinyl)amino)-2,2-difluoro-8-azaspiro[4.5]decane-8-carboxylate (180 mg, 0.46 mmol) in DCM (2 mL) was added TFA (1 mL) and the mixture was cooled to 0° C. for 20 min. The mixture was concentrated under reduced pressure with three further additions of DCM and used without further purification. MS m/z 295.2 (M+H)$^+$.

Step d: To a mixture of 3-((3-amino-2-chlorophenyl)thio)-6-chloropyrazin-2-amine (42 mg, 0.15 mmol) and N—((S)-2,2-difluoro-8-azaspiro[4.5]decan-1-yl)-2-methylpropane-2-sulfinamide (60 mg, 0.15 mmol) in a pressure tube was added DIPEA (0.3 mL, 1.8 mmol). The tube was sealed and heated in oil bath at 100° C. for 16 h. After cooling to RT the reaction mixture was diluted with brine and EtOAc and the layers were separated. The organic layer was washed with water, dried over MgSO$_4$, filtered and concentrated under reduced pressure. The resulting residue was purified by silica chromatography (20-100% EtOAc/heptane) to give the title compound (18 mg) as a brown oil. MS m/z 545.1 (M+H)$^+$.

Intermediate 12

(R)-8-(6-Amino-5-((3-amino-2-chlorophenyl)thio)pyrazin-2-yl)-N—((R)-1-(4-methyoxyphenyl)ethyl)-8-azaspiro[4.5]decan-1-amine

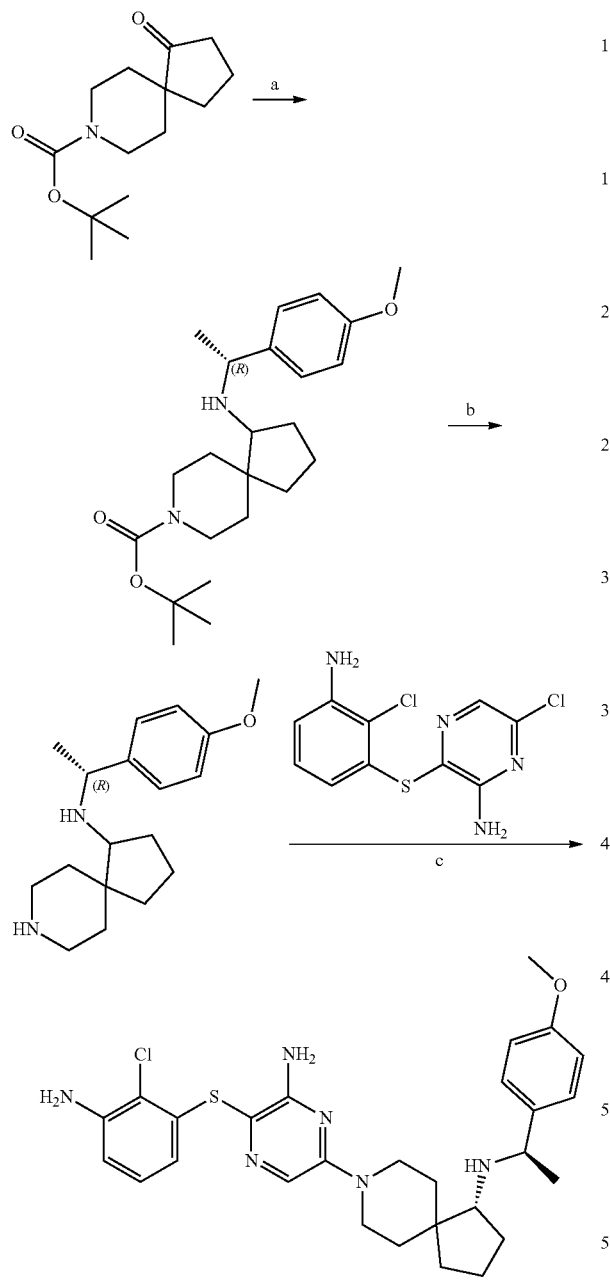

Step a: To a solution of tert-butyl 1-oxo-8-azaspiro[4.5]decane-8-carboxylate (1.15 g, 4.54 mmol), and (R)-1-(4-methoxyphenyl)ethanamine (961 mg, 6.36 mmol) in DCE (3 mL) was added sodium cyanoborohydride in portions and stirred for 16 h at RT. The mixture was diluted with sat. aq. NaHCO₃ solution (5 mL) and extracted with EtOAc (3×10 mL). The combined organic phases were washed with brine and concentrated under reduced pressure. The resulting residue containing a 9:1 mixture of diastereomers was purified by silica chromatography (0-20% EtOAc/heptane) to give tert-butyl 1-(((R)-1-(4-methoxyphenyl)ethyl)amino)-8-azaspiro[4.5]decane-8-carboxylate (major diastereomer; 431 mg). $^1$H NMR (400 MHz, DMSO-d$_6$) δ ppm 7.18-7.24 (m, 2H), 6.81-6.86 (m, 2H), 3.76 (d, J=13.64 Hz, 1H), 3.72 (s, 3H), 3.64-3.70 (m, 2H), 2.65-2.92 (m, 2H), 2.05-2.14 (m, 1H), 1.80-1.91 (m, 1H), 1.65-1.75 (m, 1H), 1.42-1.60 (m, 4H), 1.40 (s, 9H), 1.28-1.35 (m, 1H), 1.20 (d, J=6.6 Hz, 3H), 1.09-1.17 (m, 2H), 0.80 (d, J=11.4 Hz, 1H). MS m/z 389.6 (M+H)⁺.

Step b: To a solution of tert-butyl 1-(((R)-1-(4-methoxyphenyl)ethyl)amino)-8-azaspiro[4.5]decane-8-carboxylate (major diastereomer; 431 mg, 1.11 mmol) in DCM (2 mL) was added TFA (2 mL) and stirred for 10 min at RT. The reaction mixture was concentrated under reduced pressure with further addition of DCM, then diluted with sat. aq. NaHCO₃. The mixture was extracted with DCM (3×20 mL). The organics were washed with brine, dried over Na₂SO₄, filtered and concentrated under reduced pressure to give N—((R)-1-(4-methoxyphenyl)ethyl)-8-azaspiro[4.5]decan-1-amine, used without further purification. $^1$H NMR (400 MHz, Methanol-d$_4$) δ ppm 7.25 (d, J=8.6 Hz, 2H), 6.87 (d, J=8.7 Hz, 2H), 3.85-3.78 (m, 1H), 3.78 (s, 3H), 3.35 (m, 1H), 3.28 (m, 1H), 3.03 (m, 2H), 2.63 (dd, J=9.6, 7.3 Hz, 1H), 2.06-1.85 (m, 2H), 1.83-1.69 (m, 2H), 1.62 (m, 1H), 1.54-1.38 (m, 4H), 1.33 (d, J=6.6 Hz, 3H), 1.31-1.23 (m, 1H). MS m/z 289.5 (M+H)⁺.

Step c: As described for Intermediate 1, a similar procedure was performed using 3-((3-amino-2-chlorophenyl)thio)-6-chloropyrazin-2-amine (0.77 g, 2.63 mmol) and (R)—N—((R)-1-(4-methoxyphenyl)ethyl)-8-azaspiro[4.5]decan-1-amine (0.75 g, 2.60 mmol) to give the titled compound (0.95 g). MS m/z 539.3 (M+H)⁺.

Intermediate 13

N-(3-((3-Amino-5-chloropyrazin-2-yl)thio)-2-chlorophenyl)-2-hydroxy-4-oxo-6,7,8,9-tetrahydro-4H-pyrido[1,2-a]pyrimidine-3-carboxamide

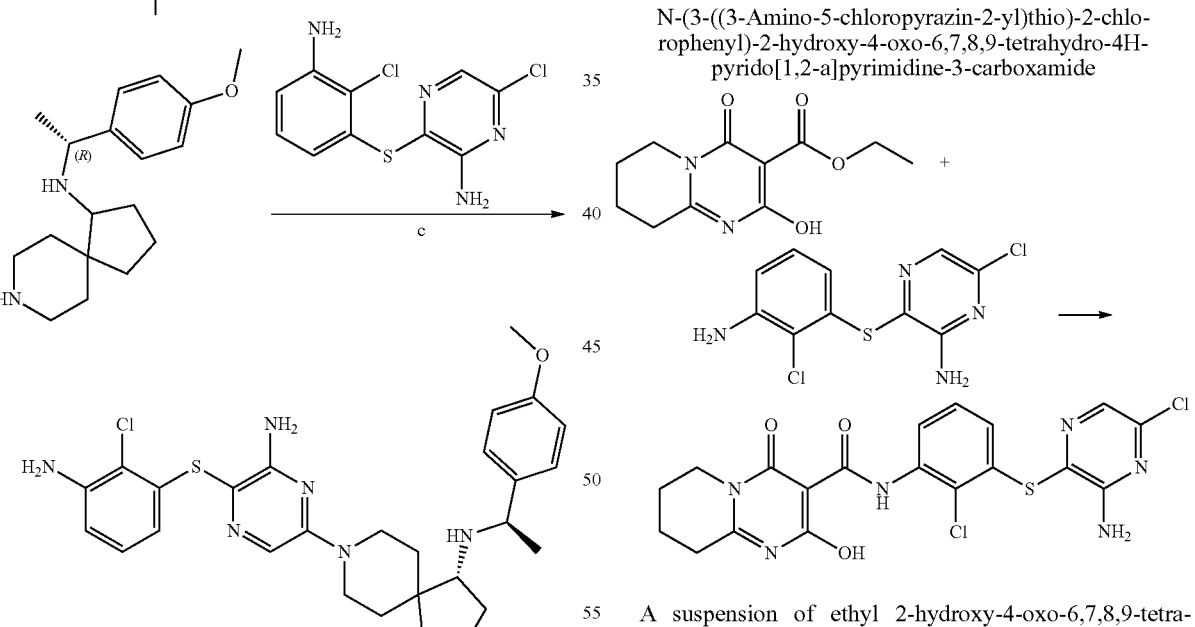

A suspension of ethyl 2-hydroxy-4-oxo-6,7,8,9-tetrahydro-4H-pyrido[1,2-a]pyrimidine-3-carboxylate (1.5 g, 5.6 mmol) and 3-((3-amino-2-chlorophenyl)thio)-6-chloropyrazin-2-amine (1.0 g, 3.5 mmol) in DMF (10 mL) was heated at 160° C. for 2.5 h. After cooling the reaction mixture was partitioned between EtOAc and brine and the layers were separated. The organic layer was washed with water and the aq. layer was extracted with additional EtOAc. The combined organic layers were dried over MgSO₄, filtered, and concentrated under reduced pressure. The concentrate was triturated with MeOH to give the titled compound (1.36 g, 90% pure) as a yellow solid. MS m/z 479.2 (M+H)⁺.

Intermediate 14

(3S,4S)-3-Methyl-2-oxa-8-azaspiro[4.5]decan-4-amine

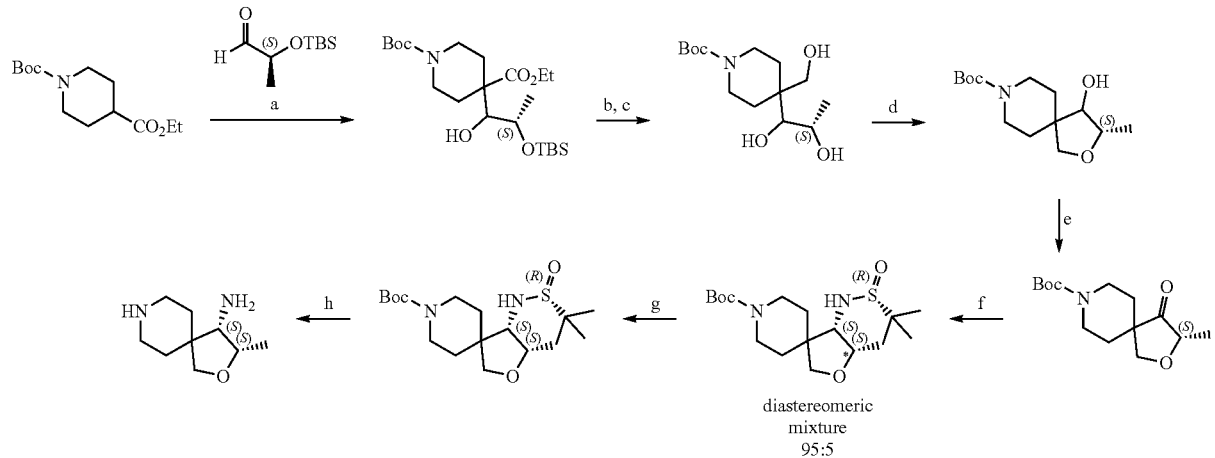

diastereomeric mixture 95:5

Step a: To a −10° C. solution of diisopropylamine (23.4 mL, 166 mmol) in THF (220 mL) was added nBuLi (2.5 M in hexane, 64.1 mL, 160 mmol) dropwise. After stirring for 30 min, 1-tert-butyl 4-ethyl piperidine-1,4-dicarboxylate (27.5 g, 107 mmol) in THF (50 mL) was added dropwise and the resulting mixture was stirred for 30 min at 0° C. (S)-2-((tert-butyldimethylsilyl)oxy)propanal (20.47 mL, 102 mmol) was added and the mixture was stirred for 1 h at 0° C. and 1 h at RT. The reaction mixture was diluted with sat. aq. NaHCO$_3$/H$_2$O (1:4, 125 mL), EtOAc (50 mL) was added, and the phases were separated. The aq. phase was further extracted with EtOAc (3×100 mL). The combined organic phases were dried over Na$_2$SO$_4$, filtered, and the solvent was removed under reduced pressure. The resulting residue was used in next step without further purification. MS m/z 346.4 (M+H−Boc)$^+$.

Step b: To a solution of crude 1-tert-butyl 4-ethyl 4-((2S)-2-((tert-butyldimethylsilyl)oxy)-1-hydroxypropyl)piperidine-1,4-dicarboxylate (95 g, 214 mmol) in THF (600 mL) was added portionwise LiBH$_4$ (7.0 g, 321 mmol) and the resulting mixture was stirred for 16 h at RT. After cooling to 0° C., sat. aq. NaHCO$_3$/H$_2$O (1:2, 150 mL) was added and the resulting mixture was vigorously stirred until frothing ceased. EtOAc (100 mL) was added, the mixture was filtered, the phases were separated, and the aq. phase was extracted with EtOAc (3×50 mL). The combined organic phases were washed with brine, dried over Na$_2$SO$_4$, filtered, and the volatiles were removed under reduced pressure to give tert-butyl 4-((2S)-2-((tert-butyldimethylsilyl)oxy)-1-hydroxypropyl)-4-(hydroxymethyl)piperidine-1-carboxylate (64.8 g) which was used in next step without further purification.

Step c: A solution of tert-butyl 4-((2S)-2-((tert-butyldimethylsilyl)oxy)-1-hydroxypropyl)-4-(hydroxymethyl)piperidine-1-carboxylate (64.8 g, 161 mmol) and TBAF (1 M in THF, 242 mL, 242 mmol) in THF (500 mL) was stirred for 2 h at RT. Sat. aq. NaHCO$_3$/H$_2$O (1:2, 150 mL) were added, the phases were separated, and the aq. phase was further extracted with EtOAc (3×100 mL). The combined organic phases were washed with brine, dried over Na$_2$SO$_4$, filtered, and the volatiles were removed under reduced pressure. The resulting residue was purified by silica chromatography (20-100% EtOAc/heptane) to give tert-butyl 4-((2S)-1,2-dihydroxypropyl)-4-(hydroxymethyl)piperidine-1-carboxylate (39.25 g) as a semi-solid colorless oil.

Step d: To a 0° C. suspension of NaH (10.60 g, 424 mmol) in THF (600 mL) was added dropwise a solution of tert-butyl 4-((2S)-1,2-dihydroxypropyl)-4-(hydroxymethyl)piperidine-1-carboxylate (35.06 g, 121 mmol) and TsCl (23.10 g, 121 mmol) in THF (200 mL). The resulting mixture was stirred for 1 h at 0° C. Sat. aq. NH$_4$Cl (~5 mL) was added slowly at −20° C. and the reaction mixture was vigorously stirred until frothing ceased. Sat. aq. NH$_4$Cl (100 mL) was added followed by brine (100 mL) and the mixture was extracted with EtOAc (3×100 mL). The combined organic phases were dried over Na$_2$SO$_4$, filtered, and concentrated under reduced pressure to give (3S)-tert-butyl 4-hydroxy-3-methyl-2-oxa-8-azaspiro[4.5]decane-8-carboxylate (32.19 g) which was used in next step without further purification. MS m/z 171.1 (M−Boc)$^-$.

Step e: A solution of (3S)-tert-butyl4-hydroxy-3-methyl-2-oxa-8-azaspiro[4.5]decane-8-carboxylate (32.19 g, 119 mmol) and Dess-Martin periodinane (67.4 g, 154 mmol) in DCM (300 mL) was stirred for 2 h at 0° C. After warming to RT, the volatiles were removed under reduced pressure and the resulting residue was purified by silica chromatography (0-40% EtOAc/heptane) to give (S)-tert-butyl3-methyl-4-oxo-2-oxa-8-azaspiro[4.5]decane-8-carboxylate (27.68 g) as a pale yellow oil. $^1$H NMR (400 MHz, Chloroform-d) δ ppm 4.09 (d, J=9.60 Hz, 1H), 3.66-3.86 (m, 4H), 3.03 (ddd, J=13.8, 9.7, 3.8 Hz, 1H), 2.90 (ddd, J=13.6, 10.2, 3.4 Hz, 1H), 1.68 (ddd, J=13.8, 9.9, 4.3 Hz, 1H), 1.41-1.59 (m, 2H), 1.30-1.40 (m, 10H), 1.20-1.25 (m, 3H).

Step f: A solution of (3S)-tert-butyl 3-methyl-4-oxo-2-oxa-8-azaspiro[4.5]decane-8-carboxylate (22.52 g mg, 84 mmol), titanium(IV) ethoxide (70.1 mL, 334 mmol), and (R)-2-methylpropane-2-sulfinamide (21 g, 173 mmol) in THF (300 mL) was stirred for 21 h at 90° C. After cooling to −4° C., MeOH (30 mL) was added, followed by dropwise addition (maintaining reaction temperature below 2° C.) of lithium borohydride (1.82 g, 84 mmol) and the resulting mixture was stirred for 1 h at −4° C. Sat. aq. NH₄Cl was slowly added followed by addition of EtOAc (500 mL). The resulting mixture was vigorously stirred for 15 min at RT and then filtered through a pad of Celite® (EtOAc). The volatiles were removed under reduced pressure and the resulting residue was purified by silica chromatography (0-100% EtOAc/heptane) to give (3S,4S)-tert-butyl 4-((R)-1,1-dimethylethylsulfinamido)-3-methyl-2-oxa-8-azaspiro[4.5]decane-8-carboxylate as a 95:5 diastereomeric mixture (minor diastereomer (3R,4S)-tert-butyl 4-((R)-1,1-dimethylethylsulfinamido)-3-methyl-2-oxa-8-azaspiro[4.5]decane-8-carboxylate).

Step g: The diastereomers were separated by chiral SFC as follows: column: LC-4 30×250 mm, flow rate: 100 g per minute, mobile phase: 30% MeOH in CO₂, detection: 225 nm, $R_t$: 0.95 min (minor diastereomer $R_t$: 0.55 min) to give (3S,4S)-tert-butyl 4-((R)-1,1-dimethylethylsulfinamido)-3-methyl-2-oxa-8-azaspiro[4.5]decane-8-carboxylate (19 g). MS m/z 375.2.

Step h: A mixture of (3S,4S)-tert-butyl 4-((R)-1,1-dimethylethylsulfinamido)-3-methyl-2-oxa-8-azaspiro[4.5]decane-8-carboxylate (51 mg, 0.136 mmol) and HCl (4 M in dioxane, 340 μL, 1.362 mmol) in MeOH (5 mL) was stirred for 1 h at 40° C. After cooling to RT, the volatiles were removed under reduced pressure to give (3S,4S)-3-methyl-2-oxa-8-azaspiro[4.5]decane-4-amine which was used in next step without further purification. MS m/z 171.1 (M+H)⁺.

Intermediate 15

(R)-3,3-Difluoro-8-azaspiro[4.5]decane-1-amine

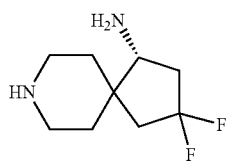

tert-butyl 1-oxo-8-azaspiro[4.5]dec-2-ene-8-carboxylate

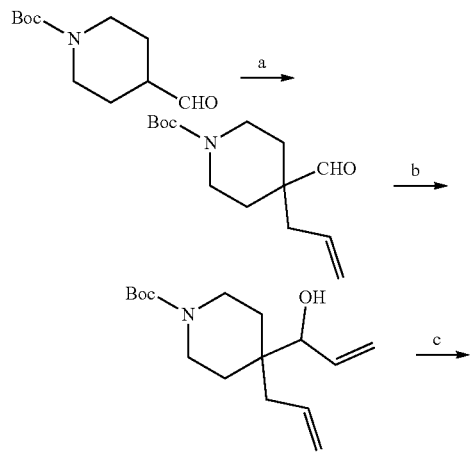

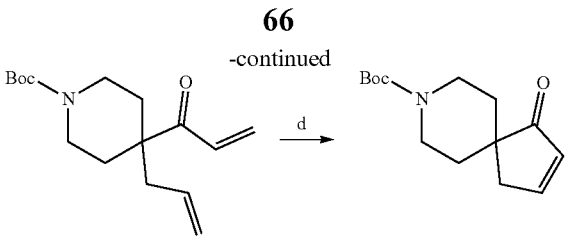

Step a: A mixture of tert-butyl 4-formylpiperidine-1-carboxylate (35.0 g, 164 mmol), lithium tert-butoxide (15.77 g, 197 mmol), and allylbromide (11.54 mL, 189 mmol) in DMF (328 mL) was stirred for 1 h at 0° C. The mixture was poured into a separation funnel containing sat. aq. NH₄Cl/H₂O (1:1, 500 mL) and it was extracted with Et₂O (5×50 mL). The combined organic phases were dried over MgSO₄, filtered, and the volatiles were removed under reduced pressure. The resulting residue was purified by silica chromatography (0-25% EtOAc/heptane) to give tert-butyl 4-allyl-4-formylpiperidine-1-carboxylate (24 g) as colorless oil. ¹H NMR (400 MHz, Chloroform-d) δ ppm 9.52 (s, 1H), 5.53-5.76 (m, 1H), 4.96-5.19 (m, 2H), 3.80 (br. s., 2H), 2.97 (t, J=11.5 Hz, 2H), 2.26 (d, J=7.3 Hz, 2H), 1.95 (dt, J=13.7, 3.1 Hz, 2H), 1.38-1.58 (m, 11H).

Step b: To a −78° C. solution of tert-butyl 4-allyl-4-formylpiperidine-1-carboxylate (24 g, 95 mmol) in THF (300 mL) under N₂ was added vinyl magnesium bromide (1 M in THF, 118 mL, 118 mmol). The resulting solution was slowly warmed up to RT within 1 h. The mixture was poured into a separation funnel containing sat. aq. NH₄Cl (250 mL) and it was extracted with EtOAc (4×50 mL). The combined organic phases were dried over MgSO₄, filtered, and the volatiles were removed under reduced pressure to give tert-butyl 4-allyl-4-(1-hydroxyallyl)piperidine-1-carboxylate (26.7 g, 95 mmol) as colorless oil. ¹H NMR (400 MHz, Chloroform-d) δ ppm 9.52 (s, 1H), 5.56-5.75 (m, 1H), 5.05-5.18 (m, 2H), 3.80 (br. s., 2H), 2.97 (t, J=11.5 Hz, 2H), 2.26 (d, J=7.3 Hz, 2H), 1.96 (dt, J=13.8, 3.1 Hz, 2H), 1.49-1.60 (m, 2H), 1.41-1.49 (m, 9H). This compound was used in next step without further purification.

Step c: A mixture of tert-butyl 4-allyl-4-(1-hydroxyallyl)piperidine-1-carboxylate (26.7 g, 95 mmol) and Dess-Martin periodinane (44.3 g, 105 mmol) in DCM (380 mL) was stirred for 1 h at RT. The mixture was poured into a separation funnel containing sat. aq. NaHCO₃/Na₂SO₃ (1:1, 300 mL) and it was extracted with DCM (4×50 mL). The combined organic phases were dried over MgSO₄, filtered, and the volatiles were removed under reduced pressure. The resulting solid was suspended in heptane (250 mL) and sonicated for 5 min. The white suspension was filtered through a pad of Celite® and the volatiles were removed under reduced pressure to give tert-butyl 4-acryloyl-4-allylpiperidine-1-carboxylate (26.5 g) as yellow oil. ¹H NMR (400 MHz, Chloroform-d) δ ppm 6.81 (dd, J=16.9, 10.4 Hz, 1H), 6.40 (dd, J=16.8, 1.9 Hz, 1H), 5.71 (dd, J=10.4, 2.0 Hz, 1H), 5.46-5.66 (m, 1H), 4.91-5.14 (m, 2H), 3.78 (br. s., 2H), 2.96 (br. s., 2H), 2.25-2.39 (m, 2H), 1.97-2.15 (m, 2H), 1.37-1.57 (m, 11H). This compound was used in next step without further purification.

Step d: To a solution of tert-butyl 4-acryloyl-4-allylpiperidine-1-carboxylate (26.5 g, 95 mmol) in toluene (degassed, 850 mL) was added Grubbs II catalyst (2.02 g, 2.38 mmol) in toluene (degassed, 100 mL). The resulting mixture was stirred for 45 min at 85° C. The solvent was removed under reduced pressure and the resulting residue was purified by silica chromatography (0-40% EtOAc/heptane) to give tert-butyl 1-oxo-8-azaspiro[4.5]dec-2-ene-8-carboxylate (20.76 g, 83 mmol) as brown solid. A solution of this compound and DDQ (565 mg, 2.49 mmol) in toluene (540 mL) was stirred for 15 min at RT. The resulting red solution was filtered through a pad of Celite®. Charcoal (200 g) was added and the resulting suspension was stirred for 2 h at RT. The mixture was filtered through a pad of Celite® and the volatiles were removed under reduce pressure. The resulting residue was purified by silica chromatography (0-40% EtOAc/heptane) to give tert-butyl 1-oxo-8-azaspiro[4.5]dec-2-ene-8-carboxylate (15.6 g) as white solid. $^1$H NMR (400 MHz, Chloroform-d) δ ppm 7.63-7.74 (m, 1H), 6.20 (dt, J=5.8, 2.2 Hz, 1H), 3.99-4.25 (m, 2H), 2.92 (t, J=11.6 Hz, 2H), 2.63 (s, 2H), 1.72-1.86 (m, 2H), 1.49 (s, 9H), 1.29 (d, J=12.9 Hz, 2H).

(1R,3R)-tert-Butyl 3-((tert-butyldimethylsilyl)oxy)-1-((R)-1,1-dimethylethylsulfinamido)-8-azaspiro[4.5]decane-8-carboxylate)

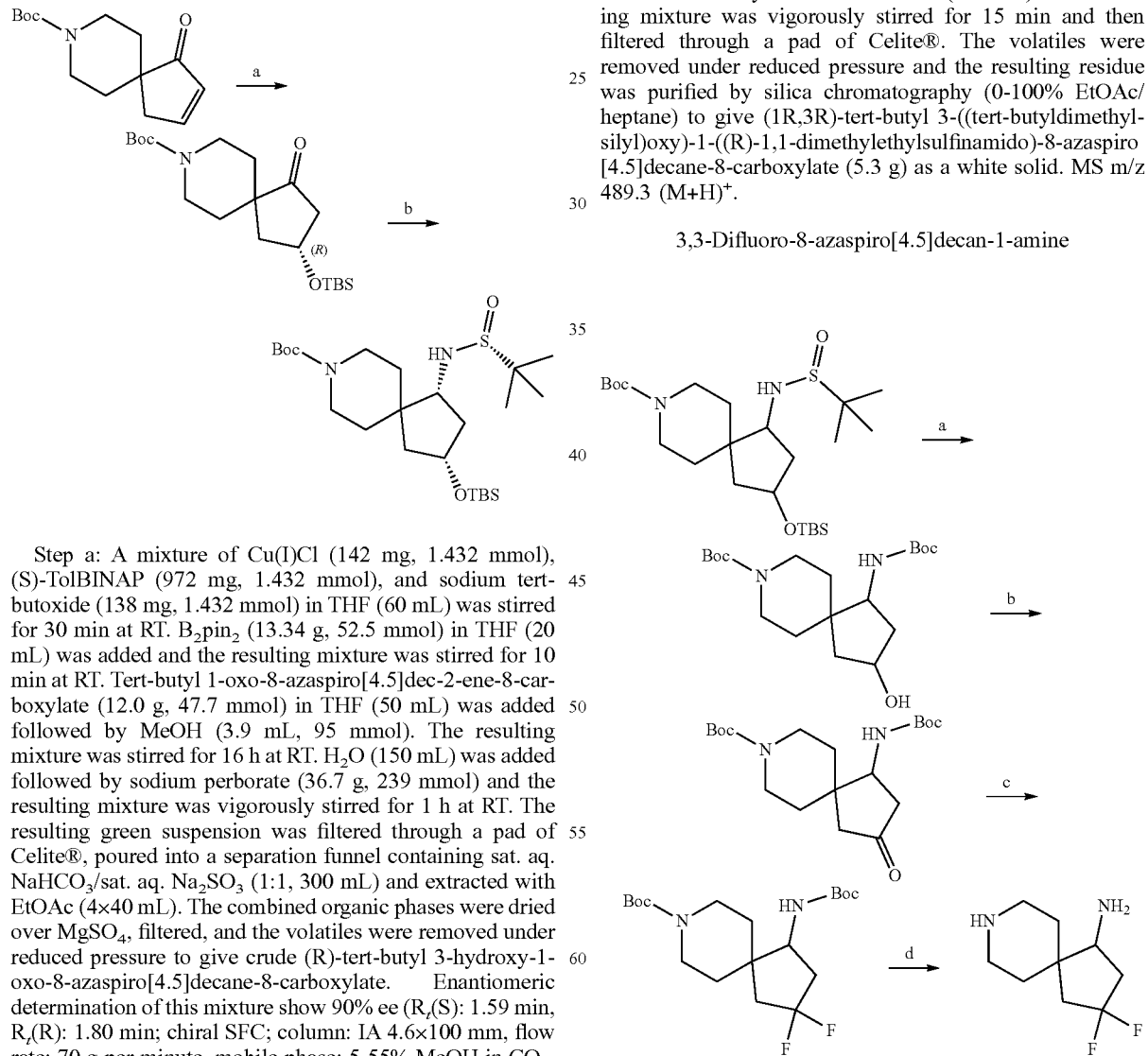

Step a: A mixture of Cu(I)Cl (142 mg, 1.432 mmol), (S)-TolBINAP (972 mg, 1.432 mmol), and sodium tert-butoxide (138 mg, 1.432 mmol) in THF (60 mL) was stirred for 30 min at RT. B$_2$pin$_2$ (13.34 g, 52.5 mmol) in THF (20 mL) was added and the resulting mixture was stirred for 10 min at RT. Tert-butyl 1-oxo-8-azaspiro[4.5]dec-2-ene-8-carboxylate (12.0 g, 47.7 mmol) in THF (50 mL) was added followed by MeOH (3.9 mL, 95 mmol). The resulting mixture was stirred for 16 h at RT. H$_2$O (150 mL) was added followed by sodium perborate (36.7 g, 239 mmol) and the resulting mixture was vigorously stirred for 1 h at RT. The resulting green suspension was filtered through a pad of Celite®, poured into a separation funnel containing sat. aq. NaHCO$_3$/sat. aq. Na$_2$SO$_3$ (1:1, 300 mL) and extracted with EtOAc (4×40 mL). The combined organic phases were dried over MgSO$_4$, filtered, and the volatiles were removed under reduced pressure to give crude (R)-tert-butyl 3-hydroxy-1-oxo-8-azaspiro[4.5]decane-8-carboxylate. Enantiomeric determination of this mixture show 90% ee (R$_t$(S): 1.59 min, R$_t$(R): 1.80 min; chiral SFC; column: IA 4.6×100 mm, flow rate: 70 g per minute, mobile phase: 5-55% MeOH in CO$_2$, detection: 220 nm UV).

A mixture of (R)-tert-butyl 3-hydroxy-1-oxo-8-azaspiro[4.5]decane-8-carboxylate crude (theor 47.7 mmol), imidazole (4.87 g, 71.6 mmol), and TBSCl (8.99 g, 59.6 mmol) in DMF (120 mL) was stirred for 16 h at RT. The reaction mixture was poured into a separation funnel containing sat. aq. NH$_4$Cl/H$_2$O (1:1, 250 mL) and it was extracted with Et$_2$O (5×50 mL). The combined organic phases were dried over MgSO$_4$, filtered and the volatiles were removed under reduced pressure. The resulting residue was purified by silica chromatography (0-30% EtOAc/heptane) to give (R)-tert-butyl 3-((tert-butyldimethylsilyl)oxy)-1-oxo-8-azaspiro[4.5]decane-8-carboxylate (13.11 g) as colorless oil that solidify upon standing.

Step b: A solution of (R)-tert-butyl 3-((tert-butyldimethylsilyl)oxy)-1-oxo-8-azaspiro[4.5]decane-8-carboxylate (8 g, 20.86 mmol), titanium(IV) ethoxide (17.49 mL, 83.0 mmol), and (R)-2-methylpropane-2-sulfinamide (5.06 g, 41.7 mmol) in THF (100 mL) was stirred for 16 h at 65° C. After cooling to −78° C., MeOH (15 mL) was added followed by lithium borohydride (1.363 g, 62.6 mmol). The resulting mixture was stirred for 16 h at −78° C. Sat. aq. NH$_4$Cl was slowly added to quench the excess of borohydride followed by addition of EtOAc (100 mL). The resulting mixture was vigorously stirred for 15 min and then filtered through a pad of Celite®. The volatiles were removed under reduced pressure and the resulting residue was purified by silica chromatography (0-100% EtOAc/heptane) to give (1R,3R)-tert-butyl 3-((tert-butyldimethylsilyl)oxy)-1-((R)-1,1-dimethylethylsulfinamido)-8-azaspiro[4.5]decane-8-carboxylate (5.3 g) as a white solid. MS m/z 489.3 (M+H)$^+$.

3,3-Difluoro-8-azaspiro[4.5]decan-1-amine

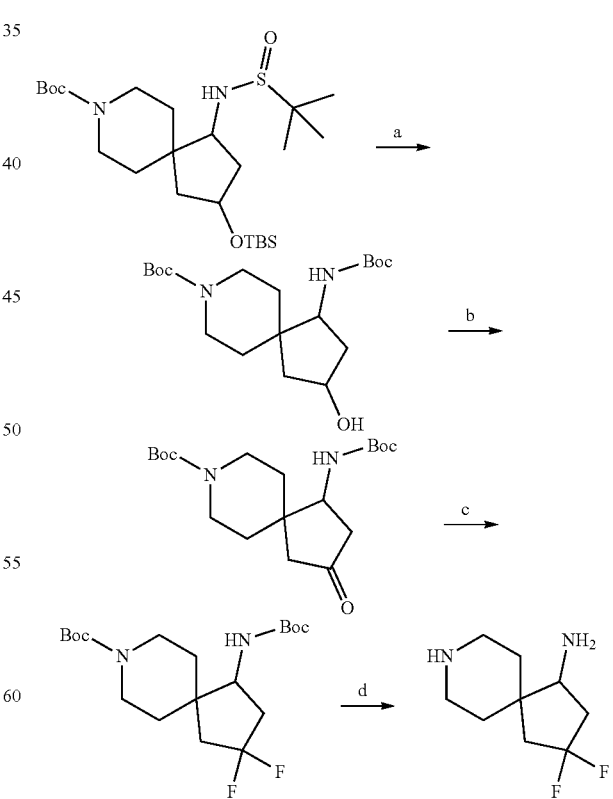

Step a: A mixture of tert-butyl 3-((tert-butyldimethylsilyl)oxy)-1-(1,1-dimethylethylsulfinamido)-8-azaspiro[4.5]decane-8-carboxylate (365 mg, 0.746 mmol) and HCl (4 M in dioxane, 1.86 mL, 7.46 mmol) in MeOH (4 mL) was stirred for 1 h at 40° C. After cooling to RT, the volatiles were removed under reduced pressure to give a white solid. MS m/z 171.1 (M+H)$^+$. A mixture of this residue, DIPEA (2.6 mL, 14.92 mmol), and Boc$_2$O (407 mg, 1.865 mmol) in THF (15 mL) was stirred for 16 h at RT. The mixture was poured into a separation funnel containing sat. aq. NH$_4$Cl and it was extracted with Et$_2$O (5×10 mL). The combined organic phases were dried over MgSO$_4$, filtered, and the volatiles were removed under reduced pressure. The resulting residue was purified by silica chromatography (10-80% EtOAc/heptane) to give tert-butyl 1-((tert-butoxycarbonyl)amino)-3-hydroxy-8-azaspiro[4.5]decane-8-carboxylate (275 mg, 0.742 mmol). MS m/z 271.3 (M+H-Boc)$^+$.

Step b: A mixture of tert-butyl 1-((tert-butoxycarbonyl)amino)-3-hydroxy-8-azaspiro[4.5]decane-8-carboxylate (275 mg, 0.742 mmol) and Dess-Martin periodinane (472 mg, 1.113 mmol) in DCM (7.5 mL) was stirred for 2 h at 0° C. The mixture was poured into a separation funnel containing sat. aq. NaHCO$_3$ and it was extracted with DCM (3×10 mL). The combined organic phases were dried over MgSO$_4$, filtered, and the volatiles were removed under reduced pressure. The resulting residue was purified by silica chromatography (5-75% EtOAc/heptane) to give tert-butyl 1-((tert-butoxycarbonyl)amino)-3-oxo-8-azaspiro[4.5]decane-8-carboxylate (135 mg). $^1$H NMR (400 MHz, Chloroform-d) δ ppm 4.57 (d, J=9.1 Hz, 1H), 4.16 (d, J=8.1 Hz, 1H), 3.89-4.08 (m, 2H), 2.77-2.93 (m, 2H), 2.71 (dd, J=19.0, 8.1 Hz, 1H), 2.50 (d, J=18.2 Hz, 1H), 2.07-2.24 (m, 2H), 1.76 (td, J=12.8, 4.7 Hz, 1H), 1.58-1.70 (m, 1H), 1.42-1.53 (m, 18H), 1.25-1.38 (m, 1H).

Step c: A mixture of tert-butyl 1-((tert-butoxycarbonyl)amino)-3-oxo-8-azaspiro[4.5]decane-8-carboxylate (95 mg, 0.258 mmol) and DeoxoFluor (190 μL, 1.031 mmol) in DCM (1 mL) was stirred for 48 h at 50° C. The mixture was poured into a separation funnel containing sat. aq. NaHCO$_3$/ice and it was extracted with EtOAc (3×5 mL). The combined organic phases were dried over MgSO$_4$, filtered, and the volatiles were removed under reduced pressure. The resulting residue was purified by silica chromatography (0-30% EtOAc/heptane) to give tert-butyl 1-((tert-butoxycarbonyl)amino)-3,3-difluoro-8-azaspiro[4.5]decane-8-carboxylate (52 mg, 0.133 mmol). $^1$H NMR (400 MHz, Chloroform-d) δ ppm 4.55 (d, J=9.4 Hz, 1H), 3.78-4.02 (m, 3H), 2.64-2.86 (m, 2H), 2.38-2.59 (m, 1H), 2.10-2.32 (m, 1H), 1.79-2.10 (m, 2H), 1.58 (qd, J=12.7, 3.8 Hz, 1H), 1.27-1.52 (m, 21H).

tert-Butyl (R)-1-((tert-butoxycarbonyl)amino)-3,3-difluoro-8-azaspiro[4.5]decane-8-carboxylate was synthesized using the above procedure or modifications to the above procedure using the chirally pure (1R,3R)-tert-butyl 3-((tert-butyldimethylsilyl)oxy)-1-((R)-1,1-dimethylethylsulfinamido)-8-azaspiro[4.5]decane-8-carboxylate as starting material.

Step d: To a suspension of tert-butyl (R)-1-((tert-butoxycarbonyl)amino)-3,3-difluoro-8-azaspiro[4.5]decane-8-carboxylate (252 mg, 0.644 mmol) in 1,4-dioxane (4 mL) was added HCl (1.6 mL, 4 M in 1,4-dioxane). The solution was stirred at RT for 16 h and then concentrated under reduced pressure to a white solid. In a small Erlenmeyer flask Na$_2$CO$_3$ (400 mg) was dissolved in 2 mL water and the crude solid was added and stirred until dissolution occurred. The solution was transferred to a separatory funnel, diluted with 6 mL of CF$_3$CH$_2$OH (20% in DCM), and the mixture was shaken vigorously. The pH of the top aq. layer was basic (~10). The layers were separated and the aq. layer was extracted 3× with DCM (20% trifluroethanol, 8 mL). The combined organic extracts were dried and concentrated under reduced pressure to a brown semi-solid that was used in the next step with no further purification. MS 191.2 nm/z (M+H)$^+$.

Intermediate 16

(1S,2S,3R)-2-Fluoro-3-methyl-8-azaspiro[4.5]decan-1-amine

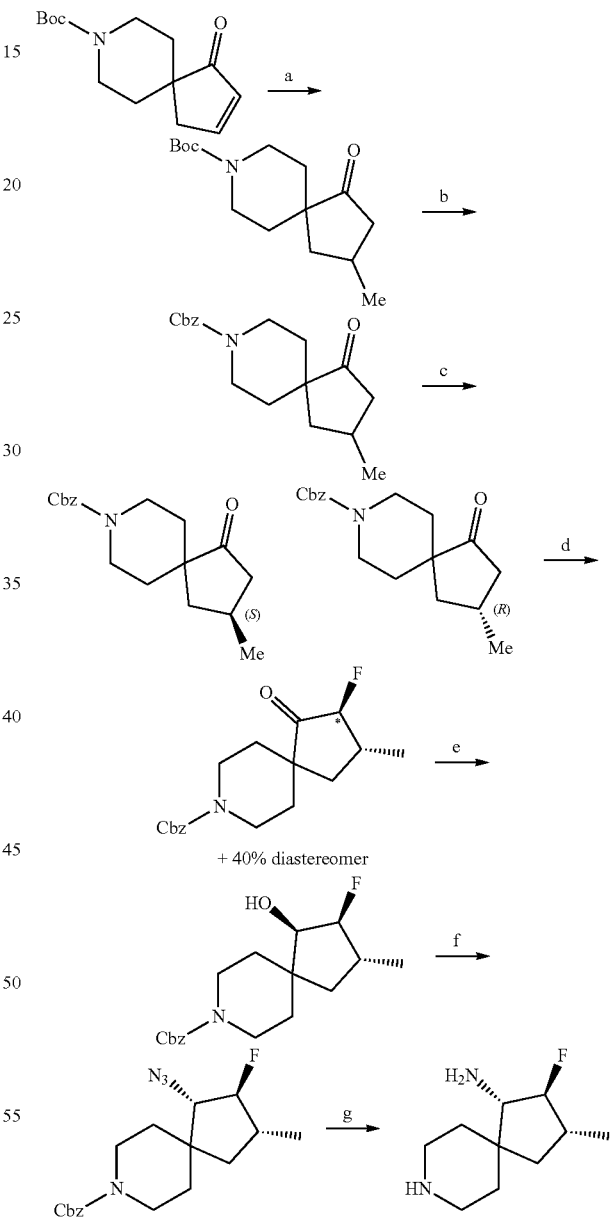

Step a: To a 0° C. suspension of tert-butyl 1-oxo-8-azaspiro[4.5]dec-2-ene-8-carboxylate (4.2 g, 16.71 mmol) under N$_2$ and Cu(I)I (6.37 g, 33.4 mmol) in Et$_2$O (100 mL) was added MeLi (1.6 M in THF, 31.3 mL, 50.1 mmol). After stirring for 90 min at 0° C., the mixture was poured into a separation funnel containing sat. aq. NH$_4$Cl and it was extracted with EtOAc (3×15 mL). The combined organic phases were dried over MgSO$_4$, filtered, and the volatiles were removed under reduced pressure. The resulting residue was purified by silica chromatography (0-50% EtOAc/heptane) to give tert-butyl 3-methyl-1-oxo-8-azaspiro[4.5]dec-2-ene-8-carboxylate (4.23 g) as colorless oil. $^1$H NMR (400 MHz, Chloroform-d) δ ppm 3.89-4.00 (m, 1H), 3.83 (d, J=13.4 Hz, 1H), 3.11 (ddd, J=13.6, 10.4, 3.3 Hz, 1H), 2.99 (ddd, J=13.6, 10.4, 3.5 Hz, 1H), 2.47-2.59 (m, 1H), 2.19-2.36 (m, 2H), 1.74-1.97 (m, 2H), 1.50-1.65 (m, 2H), 1.48 (s, 9H), 1.33-1.44 (m, 2H), 1.17 (d, J=6.3 Hz, 3H).

Step b: A mixture of tert-butyl 3-methyl-1-oxo-8-azaspiro[4.5]dec-2-ene-8-carboxylate (4.23 g, 15.82 mmol) and TFA (17 mL) in DCM (80 mL) was stirred for 30 min at RT. The volatiles were removed under reduced pressure. A mixture of the resulting residue, DIPEA (13.82 mL, 79 mmol), and benzyl chloroformate (3.39 mL, 23.73 mmol) in DCM (80 mL) was stirred for 16 h at RT. The mixture was poured into a separation funnel containing sat. aq. NH$_4$Cl and it was extracted with DCM (3×25 mL). The combined organic phases were dried over MgSO$_4$, filtered and the volatiles were removed under reduced pressure. The resulting residue was purified by silica chromatography (0-40% EtOAc/heptane) to give benzyl 3-methyl-1-oxo-8-azaspiro[4.5]decane-8-carboxylate (4.58 g) as light yellow oil. MS m/z 302.2 (M+H)$^+$.

Step c: Benzyl 3-methyl-1-oxo-8-azaspiro[4.5]decane-8-carboxylate (4.58 g, 15.20 mmol) was further purified by chiral SFC as follows: column: IA 21×250 mm, flow rate: 70 g per min, mobile phase: 45% (9:1 EtOH/MeCN) in CO$_2$, detection: 220 nm UV to give (R)-benzyl 3-methyl-1-oxo-8-azaspiro[4.5]decane-8-carboxylate (2.02 g, 6.70 mmol), R$_t$: 2.0 min; and (S)-benzyl 3-methyl-1-oxo-8-azaspiro[4.5]decane-8-carboxylate (2.11 g, 7.0 mmol), R$_t$: 3.6 min.

Step d: LiHMDS solution (1 M in THF, 8.87 mL, 8.87 mmol) was added to THF (36 mL). The solution was cooled to −78° C. then a solution of (R)-benzyl 3-methyl-1-oxo-8-azaspiro[4.5]decane-8-carboxylate (2.43 g, 8.06 mmol) in THF (12 mL) was added to above solution at −78° C. The resulting mixture was stirred at −78° C. for 30 min. A solution of N-fluoro-N-(phenylsulfonyl)benzenesulfonamide (2.80 g, 8.87 mmol) was added dropwise at −78° C. and the resulting solution was stirred at −78° C. for 30 min. To this solution was added 1:1 mixture of water and sat. NaHCO$_3$ solution (20 mL) and the mixture was warmed to RT. The solution was extracted with EtOAc 3×, the combined organic phase was washed with brine. The organic phase was dried over MgSO$_4$, filtered, and the volatiles were removed under reduced pressure. The resulting residue was purified by silica chromatography (0-50% EtOAc/heptane) to give (2S,3R)-benzyl 2-fluoro-3-methyl-1-oxo-8-azaspiro[4.5]decane-8-carboxylate (1.89 g, contains 40% of diastereomer). MS m/z 320.2 (M+H)$^+$.

Step e: To a solution of (2S,3R)-benzyl 2-fluoro-3-methyl-1-oxo-8-azaspiro[4.5]decane-8-carboxylate (1.89 g, 5.92 mmol, contains 40% of diastereomer) in THF/MeOH (9:1, 20 mL) was added lithium tetrahydroborate solution (2 M in THF, 11.84 mL, 23.67 mmol) at −78° C. The resulting mixture was stirred at −78° C. for 30 min. The solution was added sat. aq. NH$_4$Cl slowly and warmed to RT. The solution was extracted with EtOAc 3×, the combined organic phase was washed with brine. The organic phase was dried over MgSO$_4$, filtered, and the volatiles were removed under reduced pressure. The resulting residue was purified by silica chromatography (0-50% EtOAc/heptane) to give (1R,2S,3R)-benzyl 2-fluoro-1-hydroxy-3-methyl-8-azaspiro[4.5]decane-8-carboxylate (970 mg). MS m/z 322.2 (M+H)$^+$. $^1$H NMR (400 MHz, Methanol-d$_4$) δ ppm 7.37-7.28 (m, 5H), 5.10 (s, 2H), 4.47 (dt, J=54.4, 4.7 Hz, 1H), 3.86 (d, J=12.9 Hz, 2H), 3.65 (dd, J=18.0, 4.7 Hz, 1H), 3.20-3.03 (m, 2H), 2.39-2.21 (m, 1H), 2.20-2.10 (m, 1H), 1.75-1.60 (m, 2H), 1.45 (d, J=13.4 Hz, 1H), 1.29 (d, J=13.1 Hz, 1H), 1.08 (d, J=7.1 Hz, 3H), 0.96 (dd, J=13.3, 8.5 Hz, 1H).

Step f: To a solution of benzyl (1R,2S,3R)-2-fluoro-1-hydroxy-3-methyl-8-azaspiro[4.5]decane-8-carboxylate (760 mg, 2.365 mmol) in THF (16.5 mL) was added triphenylphosphine (744 mg, 2.85 mmol) and DIAD (0.557 mL, 2.84 mmol). The resulting mixture was stirred at 0° C. for 20 min. Diphenyl phosphorazidate (0.787 mL, 3.55 mmol) was added to the reaction mixture. The reaction mixture was warmed up to RT and stirred for 18 h at RT. The reaction mixture was poured into a separation funnel containing EtOAc (30 mL). The organic phase was washed sat. aq. NH$_4$Cl and brine. The organic phases were dried over MgSO$_4$, filtered, and the volatiles were removed under reduced pressure. The resulting residue was purified by silica chromatography (0-50% EtOAc/heptane) to give benzyl (1S,2S,3R)-1-azido-2-fluoro-3-methyl-8-azaspiro[4.5]decane-8-carboxylate (432 mg). MS m/z 347.2 (M+H)$^+$. $^1$H NMR (400 MHz, Chloroform-d) δ ppm 7.43-7.31 (m, 5H), 5.15 (s, 2H), 4.48 (dt, J=54.4, 7.5 Hz, 1H), 3.93 (s, 2H), 3.61 (dd, J=16.1, 6.9 Hz, 1H), 3.13-2.95 (m, 2H), 2.31-2.13 (m, 1H), 1.96 (dd, J=13.1, 9.3 Hz, 1H), 1.81-1.64 (m, 2H), 1.47 (s, 1H), 1.32-1.19 (m, 2H), 1.16 (d, J=6.7 Hz, 3H).

Step g: A suspension of Pd/C (10% wt, 65 mg) and benzyl (1S,2S,3R)-1-azido-2-fluoro-3-methyl-8-azaspiro[4.5]decane-8-carboxylate (423 mg, 1.221 mmol) in EtOH (12.2 mL) was stirred vigorously under an H$_2$ atmosphere (balloon) for 16 h. The reaction mixture was filtered through a pad of Celite® and the volatiles were removed under reduced pressure to give (1S,2S,3R)-2-fluoro-3-methyl-8-azaspiro[4.5]decan-1-amine (235 mg). MS m/z 187.2 (M+H)$^+$. $^1$H NMR (400 MHz, Chloroform-d) δ ppm 4.15 (dt, J=55.5, 8.1 Hz, 1H), 2.95 (dt, J=12.5, 3.7 Hz, 2H), 2.87 (dd, J=16.6, 8.0 Hz, 1H), 2.74 (tdd, J=12.4, 7.3, 2.8 Hz, 2H), 2.19-2.02 (m, 1H), 1.95 (dd, J=13.4, 8.4 Hz, 1H), 1.71-1.48 (m, 4H), 1.34-1.23 (m, 3H), 1.18-1.09 (m, 4H).

Intermediate 17 tert-Butyl ((1-(5-amino-6-((3-amino-2-chlorophenyl)thio)-1,2,4-triazin-3-yl)-4-methylpiperidin-4-yl)methyl)carbamate

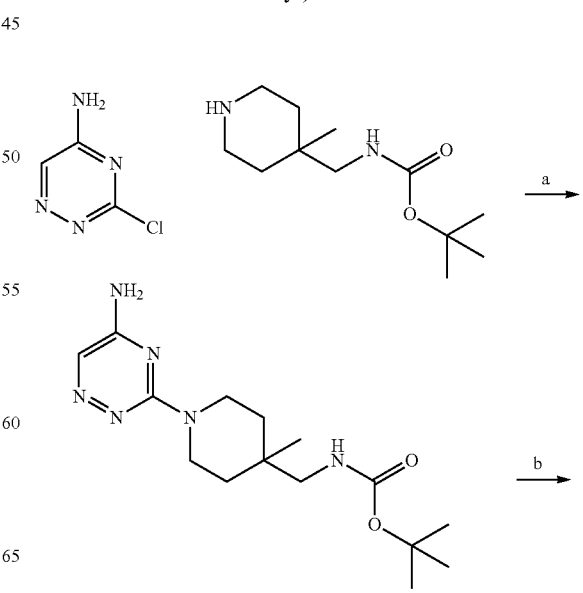

-continued

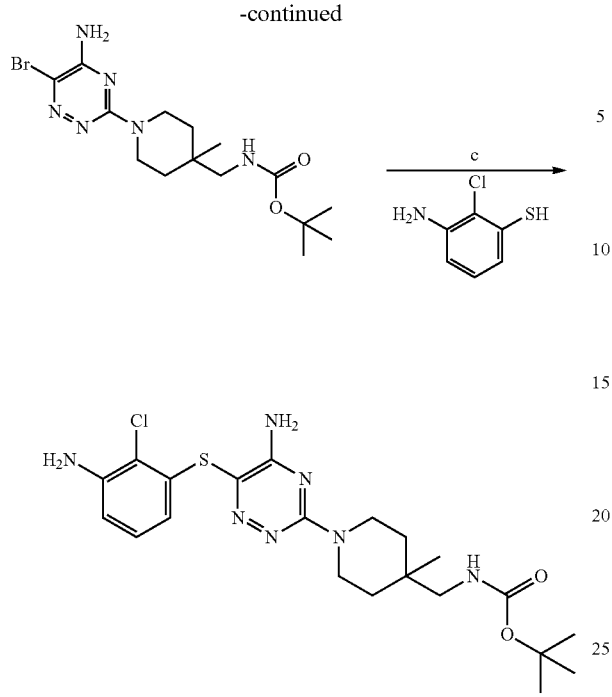

Step a: A solution of 3-chloro-1,2,4-triazine-5-amine (1.3 g, 9.96 mmol), tert-butyl ((4-methylpiperidin-4-yl)methyl) carbamate (2.7 g, 11.82 mmol) and N-methylmorpholine (3.3 mL, 30.0 mmol) in NMP (20 mL) was heated in a sealed glass reactor to 130° C. for 2 h. After cooling the reaction mixture was diluted with EtOAc (250 mL), washed with water and brine, dried over MgSO₄, filtered, and concentrated under reduced pressure. The concentrate was purified by silica chromatography (0-50% EtOAc/DCM) to give tert-butyl ((1-(5-amino-1,2,4-triazin-3-yl)-4-methylpiperidin-4-yl)methyl)carbamate (2.43 g). MS m/z 323.5 (M+H)⁺.

Step b: To a suspension of tert-butyl ((1-(5-amino-1,2,4-triazin-3-yl)-4-methylpiperidin-4-yl)methyl)carbamate (2.4 g, 7.44 mmol) in chloroform (100 mL) at 0° C. was added N-bromosuccinimide (1.5 g, 8.53 g). After 1 h at 0° C. the reaction mixture was concentrated under reduced pressure, dissolved in warm DCM (50 mL), diluted with EtOAc (300 mL), washed with 5% aq. K₂CO₃ solution, water and brine. The organics were dried over MgSO₄, filtered, and concentrated under reduced pressure. Silica chromatography (0-10% MeOH/DCM) afforded tert-butyl((1-(5-amino-6-bromo-1,2,4-triazin-3-yl)-4-methylpiperidin-4-yl)methyl) carbamate (2.88 g). MS m/z 401.5 (M+H)⁺.

Step c: A mixture of 3-amino-2-chlorobenzenethiol hydrochloride (1.71 g, 8.72 mmol), tert-butyl (1-(5-amino-6-bromo-1,2,4-triazin-3-yl)-4-methylpiperidin-4-yl)carbamate (2.80 g, 6.98 mmol), Cu(I)I (0.27 g, 1.40 mmol), TMEDA (4.21 mL, 27.9 mmol) in dioxane (30 mL) was radiated in a microwave reactor for 2 h at 125° C. After cooling the reaction mixture was diluted with DCM/MeOH (9:1, 100 mL) and filtered through a plug of Celite®. The filtrate was concentrated under reduced pressure, resuspended in EtOAc (200 mL), washed with water and brine, dried over MgSO₄, filtered and concentrated under reduced pressure. The concentrate was purified by silica chromatography chromatography (0-50% EtOAc/heptane) to the titled compound (3.29 g). MS m/z 480.4 (M+H)⁺.

Intermediate 18

Ethyl 4-hydroxy-2-oxo-2H-pyrimido[2,1-a]isoquinoline-3-carboxylate

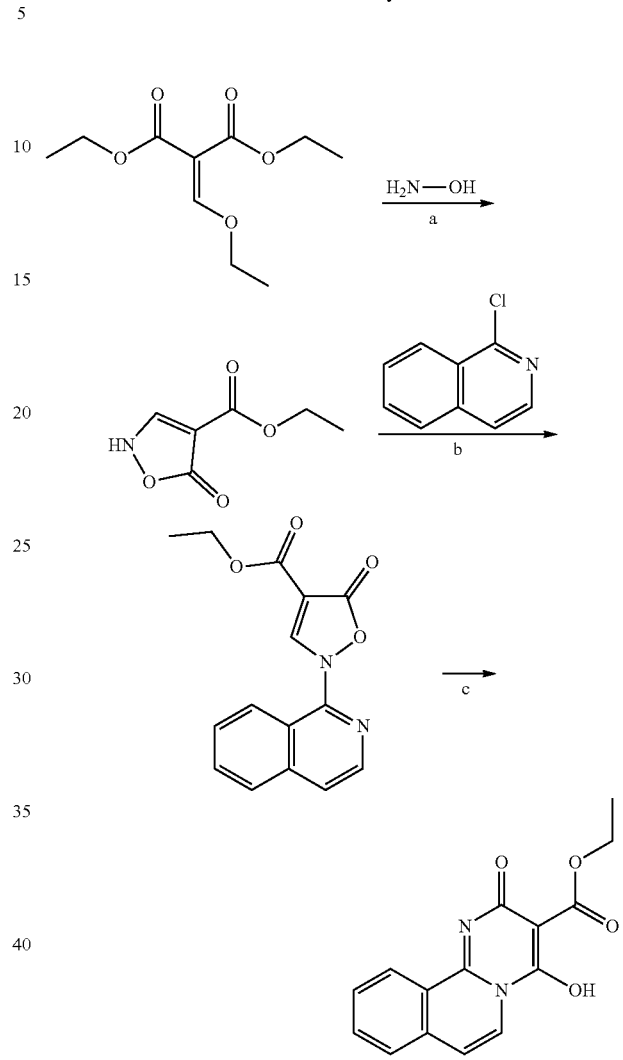

Step a: To a suspension of hydroxylamine hydrochloride (5.2 g, 75 mmol) in EtOH/water (3:2, 20 mL) was added finely ground KOH (4.2 g, 75 mmol). After stirring for 1 h at RT, the suspension was cooled to 0° C. and filtered to remove precipitated KCl. To the filtrate at 0° C. was added dropwise a solution of diethyl (2-ethoxymethylene)malonate (5.4 g, 25 mmol) dissolved in EtOH (4 mL). The reaction mixture was stirred overnight at RT and then heated to 75° C. for 2 h. After cooling to 50° C. the reaction mixture was acidified with conc. HCl (25 mL) and stirred at 50° C. for 2 h. The reaction mixture was concentrated under reduced pressure to half its original volume and the resulting precipitate was collected by filtration and dried to give ethyl 5-oxo-2,5-dihydroisoxazole-4-carboxylate as a white powder (3.5 g). MS m/z 158.0 (M+H)⁺.

Step b: A suspension of 1-chloroisoquinoline (0.82 g, 5.0 mmol) and ethyl 5-oxo-2,5-dihydroisoxazole-4-carboxylate (0.79 g, 5.0 mmol) in EtOH (20 mL) was radiated in a microwave reactor for 1 h at 100° C. After cooling the resulting precipitate was filtered and dried. The crude product was dissolved in 5% MeOH in DCM (15 mL) and purified by silica chromatography (0-20% EtOAc/DCM) to give ethyl 2-(isoquinolin-1-yl)-5-oxo-2,5-dihydroisoxazole-4-carboxylate (0.43 g). MS m/z 285.1 (M+H)⁺.

Step c: To a solution of ethyl 2-(isoquinolin-1-yl)-5-oxo-2,5-dihydroisoxazole-4-carboxylate (0.79 g, 2.78 mmol) in THF (20 mL) was added at RT a solution of Na$_2$CO$_3$ (1.4 g, 2.8 mmol) in water (20 mL). The resulting two phase reaction mixture was stirred at RT for 3 h. The THF was removed and the remaining reaction mixture was acidified to pH 1 with 6 M aq. HCl. The acidified reaction mixture was extracted with EtOAc (2×) and the combined organic layers were washed with water and brine, dried over MgSO$_4$, filtered, and concentrated under reduced pressure. The crude product was dissolved in EtOAc/DCM (10%) and purified by silica chromatography (0-20% EtOAc/DCM) to give the titled compound (0.43 g). MS m/z 285.1 (M+H)⁺.

Intermediate 19

Ethyl 1-hydroxy-3-oxo-6a,10a-dihydro-3H-pyrimido[1,2-a]quinoline-2-carboxylate

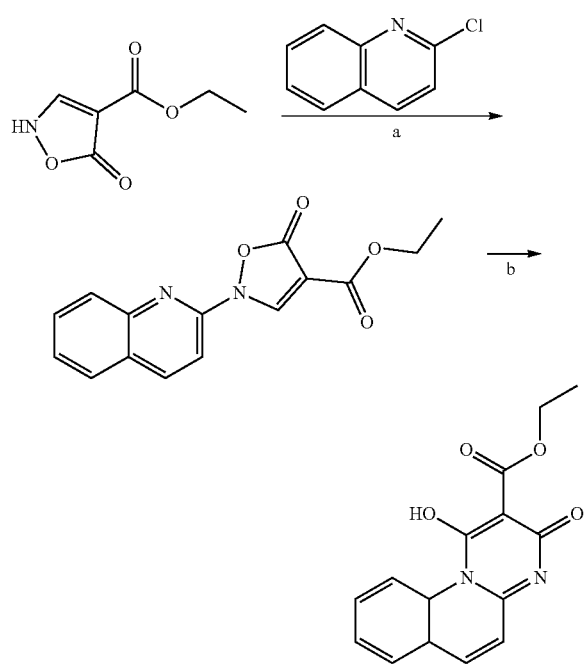

Step a: A suspension of 2-chloroisoquinoline (0.82 g, 5.0 mmol) and ethyl 5-oxo-2,5-dihydroisoxazole-4-carboxylate (0.79 g, 5.0 mmol) in EtOH (20 mL) was radiated in a microwave reactor for 1 h at 100° C. After cooling to RT the reaction mixture was concentrated under reduced pressure, re-dissolved in 5% MeOH/DCM (15 mL) and purified by silica chromatography (0-20% EtOAc/DCM) to give 0.78 g of ethyl 5-oxo-2-(quinolin-2-yl)-2,5-dihydroisoxazole-4-carboxylate. MS m/z 285.1 (M+H)⁺.

Step b: To a RT solution of ethyl 5-oxo-2-(quinolin-2-yl)-2,5-dihydroisoxazole-4-carboxylate (0.20 g, 0.70 mmol) in THF (50 mL) was added a solution of Na$_2$CO$_3$ (0.85 g, 0.80 mmol) in water (5 mL). The resulting mixture was stirred at RT for 3 h. The THF was removed under reduced pressure and the reaction mixture was acidified to pH 1 with 2 M aq. HCl. The reaction mixture was extracted with EtOAc (2×) and the combined organic layers were washed with water and brine, dried over MgSO$_4$, filtered, and concentrated under reduced pressure. The crude product was dissolved in 5% MeOH/DCM and purified by silica chromatography (0-10% EtOAc/DCM) to give the titled compound (0.054 g). MS m/z 285.1 (M−H)⁺.

Intermediate 20 tert-Butyl (1-(5-amino-6-((3-amino-2-chlorophenyl)thio)-1,2,4-triazin-3-yl)-4-methylpiperidin-4-yl)carbamate

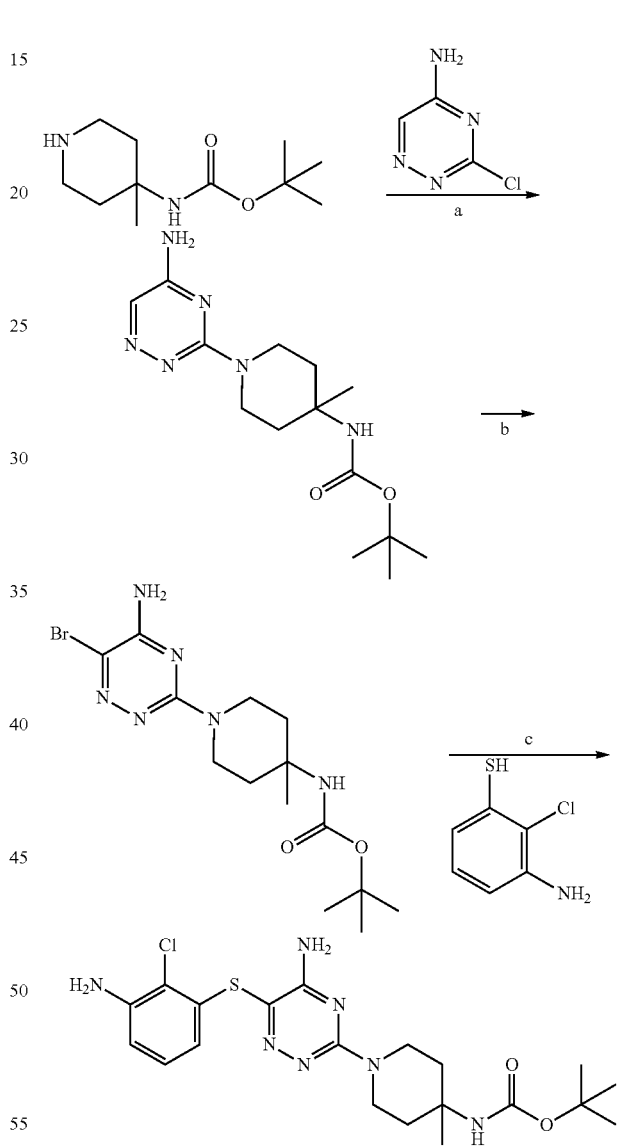

Step a: As described above for Intermediate 17, a similar procedure with 3-chloro-1,2,4-triazine-5-amine (3.0 g, 23.0 mmol) and tert-butyl (4-methylpiperidin-4-yl)carbamate (9.9 g) was used to give 7.4 g. MS m/z 309.4 (M+H)⁺.

Step b: As described for Intermediate 17, a similar procedure with tert-butyl (1-(5-amino-1,2,4-triazin-3-yl)-4-methylpiperidin-4-yl)carbamate (3.8 g, 12.3 mmol) was used to give tert-butyl (1-(5-amino-6-bromo-1,2,4-triazin-3-yl)-4-methylpiperidin-4-yl)carbamate (3.5 g). MS m/z 389.2 (M+H)⁺.

Step c: As described for Intermediate 17, a similar procedure with 3-amino-2-chlorobenzenethiol (0.32 g, 1.62 mmol) and tert-butyl (1-(5-amino-6-bromo-1,2,4-triazin-3-yl)-4-methylpiperidin-4-yl)carbamate (0.50 g, 1.30 mmol) was used to give the titled compound (0.41 g). MS m/z 466.4 (M+H)$^+$.

Intermediate 21

(R)-8-(5-Amino-6-((3-amino-2-chlorophenyl)thio)-1,2,4-triazin-3-yl)-N—((R)-1-(4-methoxyphenyl)ethyl)-8-azaspiro[4.5]decan-1-amine

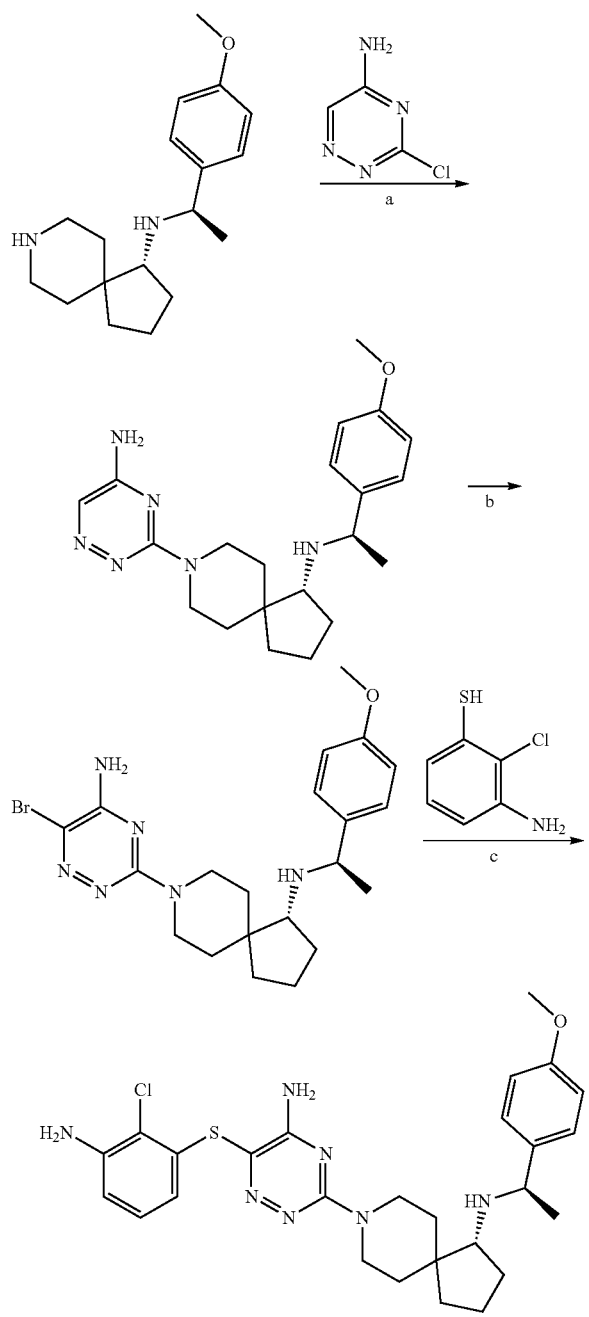

Step a: As described for Intermediate 17, a similar procedure using 3-chloro-1,2,4-triazine-5-amine (0.51 g, 3.93 mmol) and (R)—N—((R)-1-(4-methoxyphenyl)ethyl)-8-azaspiro[4.5]decan-1-amine (1.08 g, 3.74 mmol) was used to give 0.78 g of (R)-8-(5-amino-1,2,4-triazin-3-yl)-N—((R)-1-(4-methoxyphenyl)ethyl)-8-azaspiro[4.5]decan-1-amine. MS m/z 383.3 (M+H)$^+$.

Step b: As described for Intermediate 17, a similar procedure with (R)-8-(5-amino-1,2,4-triazin-3-yl)-N—((R)-1-(4-methoxyphenyl)ethyl)-8-azaspiro[4.5]decan-1-amine (0.48 g, 1.26 mmol) was used to give 0.23 g (0.49 mmol). MS m/z 461.1 (M+H)$^+$.

Step c: As described for Intermediate 17, a similar procedure with 3-amino-2-chlorobenzenethiol (0.07 g, 0.35 mmol) and (R)-8-(5-amino-6-bromo-1,2,4-triazin-3-yl)-N—((R)-1-(4-methoxyphenyl)ethyl)-8-azaspiro[4.5]decan-1-amine (0.13 g, 0.27 mmol) was used to give 0.12 g (R)-8-(5-amino-6-((3-amino-2-chlorophenyl)thio)-1,2,4-triazin-3-yl)-N—((R)-1-(4-methoxyphenyl)ethyl)-8-azaspiro[4.5]decan-1-amine. MS m/z 540.3 (M+H)$^+$.

Intermediate 22 tert-Butyl (1-(5-((3-amino-2-chlorophenyl)thio)pyrazin-2-yl)-4-methylpiperidin-4-yl)carbamate

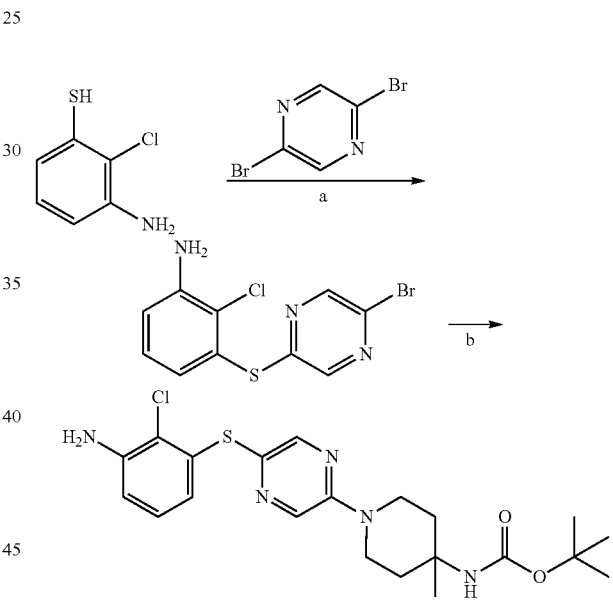

Step a: A mixture of 3-amino-2-chlorobenzenethiol hydrochloride (0.21 g, 1.05 mmol), 2,5-dibromopyrazine (0.62 g, 2.61 mmol), Cu(I) iodide (0.04 g, 0.21 mmol), 1,10-phenanthroline (0.08 g, 0.42 mmol) and potassium phosphate (0.44 g, 2.10 mmol) in dioxane (7 mL) was radiated in a microwave reactor for 1 h at 100° C. After cooling to RT the reaction mixture was filtered through a pad of Celite® (EtOAc) and the filtrate was concentrated under reduced pressure. The concentrate was purified by silica chromatography (0-100% EtOAc/heptane) to give 0.17 g of 3-((5-bromopyrazin-2-yl)thio)-2-chloroaniline. MS m/z 317.9 (M+H)$^+$.

Step b: To a mixture of 3-((5-bromopyrazin-2-yl)thio)-2-chloroaniline (0.70 g, 2.21 mmol), tert-butyl((4-methylpiperidin-4-yl)methyl)carbamate (0.76 g, 3.32 mmol), dicyclohexyl(2',6'-diisopropoxybiphenyl-2-yl)phosphine (52 mg, 0.11 mmol), chloro(2-dicyclohexylphosphino-2',6'-diisopropoxy-1,1'-biphenyl) [2-(2'-amino-1,1'-biphenyl)]palladium(II), (81 mg, 0.11 mmol) in dioxane (25 mL) was added at RT sodium tert-butoxide (0.30 g, 3.10 mmol). After stirring for 14 h at 90° C., the reaction mixture was cooled to RT, combined with silica gel and concentrated under reduced pressure to dryness. The resulting residue was purified by silica chromatography (0-100% EtOAc/heptane) to give the titled compound (0.50 g). MS m/z 450.2 (M+H)+.

Intermediate 23 tert-Butyl ((1-(5-((3-amino-2-chlorophenyl)thio)pyrazin-2-yl)-4-methylpiperidin-4-yl)methyl)carbamate

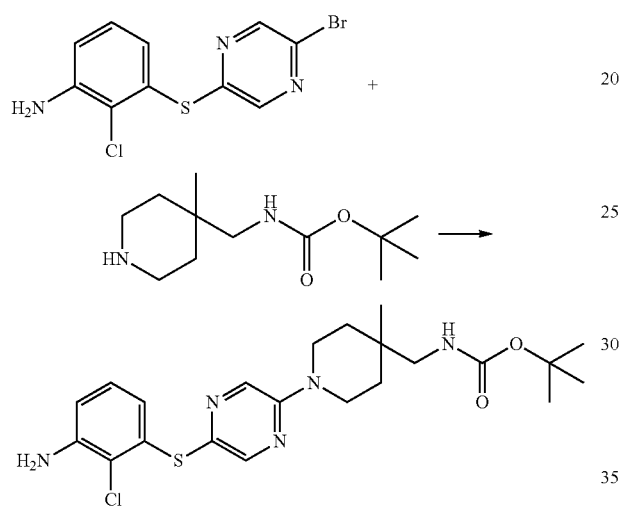

As described for Intermediate 1, a similar procedure was performed using 3-((5-bromopyrazin-2-yl)thio)-2-chloroaniline (0.70 g, 2.21 mmol) and tert-butyl ((4-methylpiperidin-4-yl)methyl)carbamate (0.76 g, 3.32 mmol) to give the titled compound (0.46 g). MS m/z 464.2 (M+H)+.

Intermediate 24 tert-Butyl (1-(6-amino-5-((4-amino-2-chlorophenyl)thio)pyrazin-2-yl)-4-methylpiperidin-4-yl)carbamate

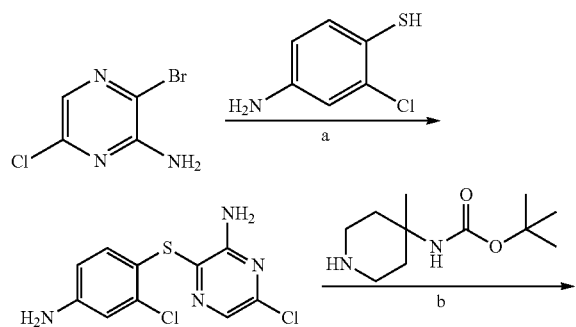

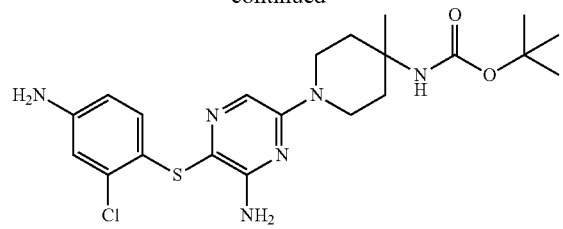

Step a: As described for Intermediate 1, a similar procedure was performed using 4-amino-2-chlorobenzenethiol (1.0 g, 6.3 mmol), 3-bromo-6-chloropyrazin-2-amine (1.3 g, 6.26 mmol), Cu(I) iodide (0.239 g, 1.3 mmol), 1,10-phenanthroline (0.45 g, 2.5 mmol) and potassium phosphate (3.32 g, 15.7 mmol) to give 3-((4-amino-2-chlorophenyl)thio)-6-chloropyrazin-2-amine (0.95 g). MS m/z 287.0 (M+H)+.

Step b: As described for Intermediate 2, a similar procedure was performed using 3-((4-amino-2-chlorophenyl)thio)-6-chloropyrazin-2-amine (0.74 g, 3.5 mmol) and tert-butyl ((4-methylpiperidin-4-yl)methyl)carbamate (0.83 g, 2.9 mmol) to give the titled compound (0.30 g). MS m/z 465.0 (M+H)+.

Intermediate 25

Ethyl 4-hydroxy-1,5,5-trimethyl-2-oxo-2,5-dihydro-1H-pyrrole-3-carboxylate

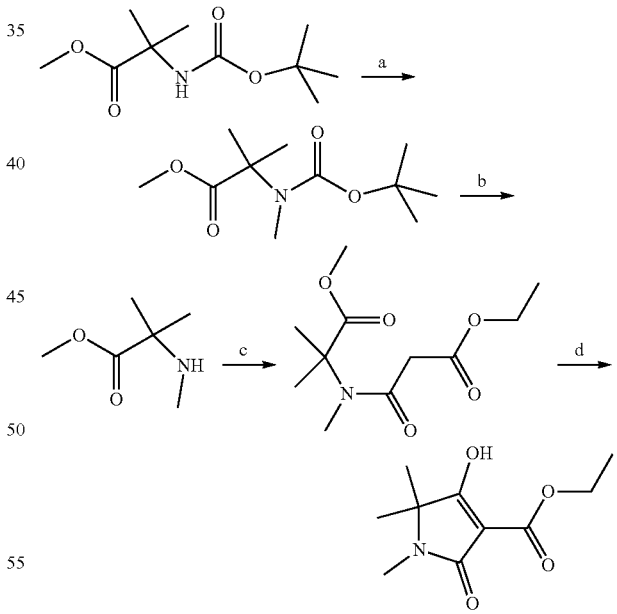

Step a: To a THF (20 mL) solution of methyl 2-((tert-butoxycarbonyl)amino)-2-methylpropanoate (1.49 g, 6.86 mmol) at 0° C. was added sodium hydride (60% in mineral oil), 0.49 g, 20.57 mmol). The reaction mixture was stirred for 5 min, iodomethane (0.52 mL, 8.23 mmol) was added dropwise into the reaction mixture. The reaction mixture was warmed up to RT and stirred overnight. The reaction mixture was quenched with water until frothing ceased. THF was removed under reduced pressure and the crude product was extracted with EtOAc and purified by flash silica chromatography (0-25% EtOAc/heptane) to afford methyl 2-((tert-butoxycarbonyl)(methyl)amino)-2-methylpropanoate. (585 mg). ¹H NMR (400 MHz, Chloroform-d) δ ppm 3.69 (s, 3H), 2.90 (s, 3H), 1.42 (s, 15H).

Step b: To a solution of methyl 2-((tert-butoxycarbonyl)(methyl)amino)-2-methylpropanoate (563 mg, 2.43 mmol) in DCM (5 mL) was added TFA (5.0 mL, 64.9 mmol). The reaction mixture was stirred at RT for 3 h and then concentrated under reduced pressure to afford methyl 2-methyl-2-(methylamino)propanoate, a white crystalline solid. (597 mg, 2.43 mmol). ¹H NMR (400 MHz, Methanol-d₄) δ ppm 3.88 (s, 3H), 2.70 (s, 3H), 1.59 (s, 6H).

Step c: To a suspension of methyl 2-methyl-2-(methylamino)propanoate (319 mg, 2.43 mmol) in THF (10 mL) was added triethylamine (1.02 mL, 7.29 mmol). The resulting mixture was cooled to 0° C. and ethyl 3-chloro-3-oxopropanoate (530 mg, 3.52 mmol) was added. The reaction mixture was warmed to RT and stirred for 1 h. The reaction mixture was concentrated under reduced pressure and purified by flash silica chromatography (0-50% EtOAc/heptane) to afford ethyl 3-((1-methoxy-2-methyl-1-oxopropan-2-yl)(methyl)amino)-3-oxopropanoate as a pale yellow oil (455 mg). MS m/z 246.3 (M+H)⁺. ¹H NMR (400 MHz, Chloroform-d) δ ppm 4.27-4.11 (m, 2H), 3.68 (d, J=0.9 Hz, 3H), 3.44 (s, 2H), 2.97 (s, 3H), 1.43 (s, 6H), 1.26 (t, J=7.1 Hz, 3H).

Step d: To a solution of ethyl 3-((1-methoxy-2-methyl-1-oxopropan-2-yl)(methyl)amino)-3-oxopropanoate (450 mg, 1.83 mmol) in EtOH (6 mL) was added sodium ethanolate (1.03 mL, 2.75 mmol) at RT. The reaction mixture was heated at 85° C. for 5 min, was cooled and was diluted with Et₂O. The precipitate was filtered and washed with Et₂O. The dried solid was dissolved in water and acidified with 2 M HCl. The mixture was concentrated under reduced pressure and purified by flash silica chromatography (0-10% MeOH/DCM) to afford ethyl 4-hydroxy-1,5,5-trimethyl-2-oxo-2,5-dihydro-1H-pyrrole-3-carboxylate (306 mg). MS m/z 214.1 (M+H)⁺. ¹H NMR (400 MHz, Chloroform-d) δ ppm 11.27 (s, 1H), 4.37 (q, J=7.0 Hz, 2H), 2.97-2.72 (m, 3H), 1.49-1.22 (m, 9H).

Intermediate 26

(S)-Ethyl 4-hydroxy-2-oxo-5-phenyl-2,5-dihydro-1H-pyrrole-3-carboxylate

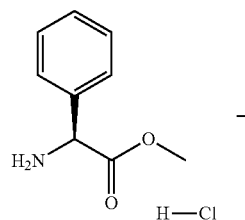

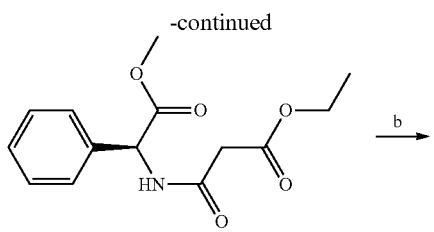

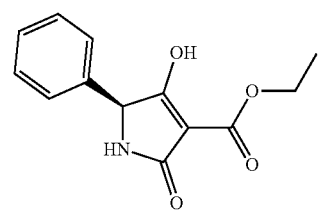

Step a: To a suspension of (S)-methyl 2-amino-2-phenylacetate hydrochloride (1.5 g, 7.44 mmol) in THF (14.9 mL) was added triethylamine (2.6 ml, 18.6 mmol). The resulting mixture was cooled to 0° C. and ethyl 3-chloro-3-oxopropanoate (1.17 g, 7.81 mmol) was added. The reaction mixture was warmed up to RT and stirred for 1 h. The reaction mixture was concentrated under reduced pressure and purified by flash silica chromatography (0-50% EtOAc/heptane) to afford (S)-ethyl 3-((2-methoxy-2-oxo-1-phenylethyl)amino)-3-oxopropanoate as a pale yellow solid (1.72 g). MS m/z 280.1 (M+H)⁺.

Step b: To a solution of (S)-ethyl 3-((2-methoxy-2-oxo-1-phenylethyl)amino)-3-oxopropanoate (1.0 g, 3.58 mmol) in EtOH (12 mL) was added sodium ethanolate (1.27 mL, 3.4 mmol) at RT. The reaction mixture was heated at 85° C. for 5 min, was cooled and was diluted with Et₂O. The precipitate was filtered and washed with Et₂O. The dried solid was dissolved in water and acidified with 2 M HCl. The mixture was concentrated under reduced pressure and the resulting solid was washed with water to give (S)-ethyl 4-hydroxy-2-oxo-5-phenyl-2,5-dihydro-1H-pyrrole-3-carboxylate (600 mg). MS m/z 248.1 (M+H)⁺.

Example 1

N-(3-((3-Amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide

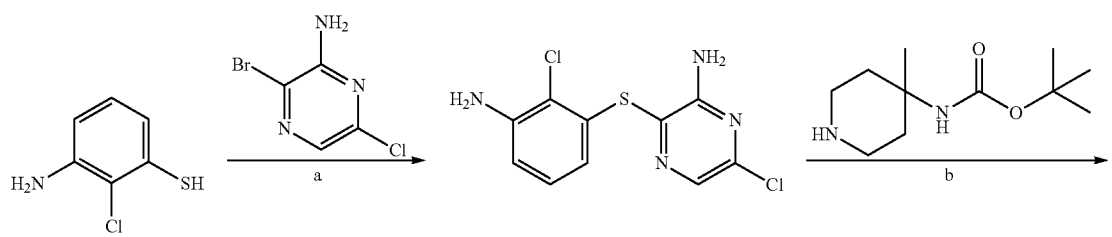

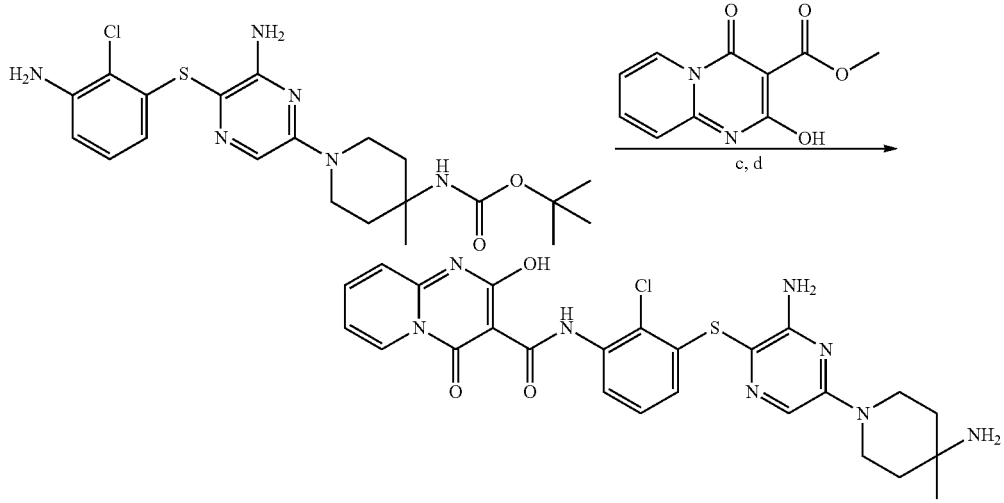

Step a: A suspension of 3-amino-2-chlorobenzenethiol hydrochloride (8.0 g, 40.8 mmol), 3-bromo-6-chloropyrazin-2-amine (6.0 g, 28.8 mmol), Cu(I) iodide (1.1 g, 5.8 mmol), 1,10-phenanthroline (2.1 g, 11.7 mmol) and potassium phosphate (12.5 g, 58.9 mmol) in dioxane (80 mL) was heated to 85° C. for 4 h. After cooling to RT, the reaction mixture was diluted with EtOAc (100 mL), filtered through a pad of Celite®, concentrated under reduced pressure to an oil and suspended in DCM (100 mL). The resulting off-white precipitate was collected by filtration and dried to give 3-((3-amino-2-chlorophenyl)thio)-6-chloropyrazin-2-amine (6.5 g). MS m/z 287.1 (M+H)$^+$.

Step b: A suspension of 3-((3-amino-2-chlorophenyl)thio)-6-chloropyrazin-2-amine (0.29 g, 1.0 mmol), tert-butyl (4-methylpiperidin-4-yl)carbamate (0.43 g, 2.0 mmol) and DIPEA (0.87 mL, 5.0 mmol) in NMP (5 mL) was radiated in a microwave reactor to 150° C. for 2 h. After cooling to RT, the reaction mixture was diluted with EtOAc (100 mL), washed with water and brine, dried over MgSO$_4$, filtered and concentrated under reduced pressure. The crude product was purified by silica chromatography (10-50% EtOAc/heptane) to give 0.44 g of tert-butyl (1-(6-amino-5-((3-amino-2-chlorophenyl)thio)pyrazin-2-yl)-4-methylpiperidin-4-yl)carbamate. MS m/z 465.2 (M+H)$^+$.

Step c: A suspension of tert-butyl (1-(6-amino-5-((3-amino-2-chlorophenyl)thio)pyrazin-2-yl)-4-methylpiperidin-4-yl)carbamate (0.13 g, 0.26 mmol) and methyl 2-hydroxy-4-oxo-4H-pyrido[1,2-a]pyrimidine-3-carboxylate (69.1 mg, 0.314 mmol) in bromobenzene (2 mL) was heated to 170° C. in a microwave reactor for 1 h. After cooling the reaction mixture to RT, it was concentrated under reduced pressure and the resulting residue was purified by HPLC (15-40% MeCN in water, 0.1% NH$_4$OH modifier), to give tert-butyl (1-(6-amino-5-((2-chloro-3-(2-hydroxy-4-oxo-4H-pyrido[1,2-a]pyrimidine-3-carboxamido)phenyl)thio)pyrazin-2-yl)-4-methylpiperidin-4-yl)carbamate (0.09 g). MS m/z 653.3 (M+H)$^+$.

Step d: To a solution of tert-butyl (1-(6-amino-5-((2-chloro-3-(2-hydroxy-4-oxo-4H-pyrido[1,2-a]pyrimidine-3-carboxamido)phenyl)thio)pyrazin-2-yl)-4-methylpiperidin-4-yl)carbamate (0.09 g, 0.14 mmol) in DCM (0.5 mL) was added TFA (0.5 mL). After stirring at RT for 2 h, the volatiles were removed under reduced pressure and the resulting residue was purified by HPLC (15-40% MeCN in water, 0.1% TFA modifier). The lyophilized product was dissolved in MeOH containing HCl (1.2 M) and dried to give N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide as the HCl salt (0.085 g). $^1$H NMR (400 MHz, Methanol-d$_4$) δ ppm 9.19 (d, J=6.8 Hz, 1H), 8.34 (d, J=8.0 Hz, 1H), 8.24 (t, J=7.9 Hz, 1H), 7.81 (s, 1H), 7.61 (d, J=8.7 Hz, 1H), 7.52 (d, J=7.1 Hz, 1H), 7.29 (t, J=8.3 Hz, 1H), 6.74 (d, J=7.9 Hz, 1H), 4.26 (d, J=14.2 Hz, 2H), 3.52 (m, 2H), 1.93 (m, 4H), 1.53 (s, 3H). HRMS calcd for C$_{25}$H$_{26}$ClN$_8$O$_3$S (M+H)$^+$553.1537, found 553.1524. The IC$_{50}$=0.006 μM.

The following compounds identified in Table 1 were made using the procedure or modifications to the procedure as exemplified for Example 1.

TABLE 1

| Example | Compound | Characterization | IC$_{50}$ (μM) |
|---|---|---|---|
| 2 | (structure shown) | as TFA salt: $^1$H NMR (400 MHz, Methanol-d$_4$) δ ppm 9.17-9.10 (m, 1 H), 8.28 (dd, J = 8.3, 1.4 Hz, 1 H), 8.13 (ddd, J = 8.7, 6.8, 1.6 Hz, 1 H), 7.58 (s, 1 H), 7.55 (dt, J = 8.8, 1.1 Hz, 1 H), 7.42 (td, J = 7.0, 1.3 Hz, 1 H), 7.15 (t, J = 8.1 Hz, 1 H), 6.50 (dd, J = 8.0, 1.4 Hz, 1 H), 4.03 (dt, J = 13.9, 4.7 Hz, 2 H), 3.43 (ddd, J = 13.7, 9.4, 4.1 Hz, 2 H), | 0.007 |

TABLE 1-continued

| Example | Compound | Characterization | IC$_{50}$ (μM) |
|---|---|---|---|
| | N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide | 2.90 (s, 2 H), 1.58 (tdd, J = 14.1, 9.1, 4.5 Hz, 4 H), 1.19 (s, 3 H). HRMS calcd for C$_{26}$H$_{28}$ClN$_8$O$_3$S (M + H)$^+$ 567.1694, found 567.1717. | |
| 3 | N-(3-((3-amino-5-(4-(aminomethyl)-4-methylpiperidin-1-yl)pyrazin-2-yl)thio)-2-chlorophenyl)-7-hydroxy-5-oxo-5H-thiazolo[3,2-a]pyrimidine-6-carboxamide | as TFA salt: $^1$H NMR (400 MHz, Methanol-d$_4$) δ ppm 8.23 (dd, J = 8.3, 1.5 Hz, 1 H), 8.07 (d, J = 4.8 Hz, 1 H), 7.58 (s, 1 H), 7.43 (d, J = 4.7 Hz, 1 H), 7.14 (t, J = 8.1 Hz, 1 H), 6.51 (dd, J = 7.9, 1.4 Hz, 1 H), 4.11-3.93 (m, 2 H), 3.43 (ddd, J = 13.7, 9.4, 4.0 Hz, 2 H), 2.92 (s, 2 H), 1.66-1.50 (m, 4 H), 1.20 (s, 3 H). HRMS calcd for C$_{24}$H$_{26}$ClN$_8$O$_3$S$_2$ (M + H)$^+$ 573.1258, found 573.1266. | 0.006 |
| 4 | N-(3-((3-amino-5-(4-(aminomethyl)-4-methylpiperidin-1-yl)pyrazin-2-yl)thio)-2-chlorophenyl)-3-cyclopropyl-4-hydroxy-7-methyl-6-oxo-6,7-dihydrothieno[2,3-b]pyridine-5-carboxamide | as TFA salt: $^1$H NMR (400 MHz, Methanol-d$_4$) δ ppm 12.97 (s, 1 H), 8.26 (dd, J = 8.4, 1.5 Hz, 1 H), 7.60 (s, 1 H), 7.17 (t, J = 8.1 Hz, 1 H), 6.68 (s, 1 H), 6.54 (dd, J = 8.0, 1.3 Hz, 1 H), 4.05 (dt, J = 13.9, 4.7 Hz, 2 H), 3.69 (s, 3 H), 3.45 (ddd, J = 13.6, 9.4, 4.0 Hz, 2 H), 2.93 (s, 2 H), 2.52 (d, J = 5.8 Hz, 1 H), 1.68-1.52 (m, 4 H), 1.21 (s, 3 H), 1.02-0.93 (m, 2 H), 0.78-0.68 (m, 2 H). HRMS calcd for C$_{29}$H$_{33}$ClN$_7$O$_3$S2 (M + H)$^+$ 626.1775, found 626.1785. | 1.03 |
| 5 | N-(3-((3-amino-5-(4-(aminomethyl)-4-methylpiperidin-1-yl)pyrazin-2-yl)thio)-2-chlorophenyl)-2-hydroxy-4-oxo-4H-pyrazino[1,2-a]pyrimidine-3-carboxamide | as TFA salt: $^1$H NMR (400 MHz, DMSO-d$_6$) δ ppm 15.18 (s, 1 H), 12.05 (s, 1 H), 9.13 (d, J = 1.2 Hz, 1 H), 8.83 (dd, J = 4.7, 1.2 Hz, 1 H), 8.37 (d, J = 4.7 Hz, 1 H), 8.12 (dd, J = 8.3, 1.4 Hz, 1 H), 7.75 (t, J = 6.2 Hz, 3 H), 7.66 (s, 1 H), 7.27 (t, J = 8.1 Hz, 1 H), 6.47 (dd, J = 8.0, 1.4 Hz, 1 H), 6.42-5.99 (m, 2 H), 3.88 (dt, J = 13.7, 4.7 Hz, 2H), 3.36 (ddd, J = 13.3, 9.3, 3.5 Hz, 2 H), 2.80 (q, J = 5.8 Hz, 2 H), 1.51 (ddd, J = 13.3, 9.5, 4.1 Hz, 2 H), 1.45-1.35 (m, 2 H), 1.07 (s, 3 H). HRMS calcd for C$_{25}$H$_{27}$ClN$_9$O$_3$S (M + H)$^+$ 568.1646, found 568.1631. | 0.003 |

TABLE 1-continued

| Example | Compound | Characterization | IC₅₀ (μM) |
|---|---|---|---|
| 6 | 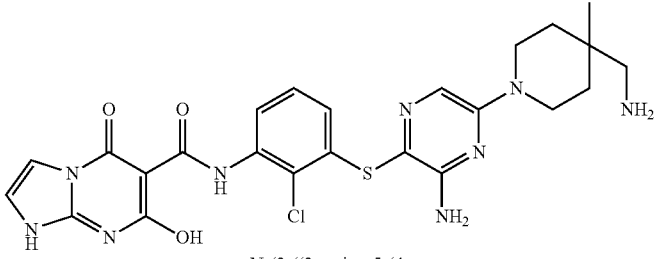<br>N-(3-((3-amino-5-(4-(aminomethyl)-4-methylpiperidin-1-yl)pyrazin-2-yl)thio)-2-chlorophenyl)-7-hydroxy-5-oxo-1,5-dihydroimidazo[1,2-a]pyrimidine-6-carboxamide | as TFA salt: $^1$H NMR (400 MHz, DMSO-$d_6$) δ ppm 14.98 (s, 1 H), 13.23 (s, 1 H), 12.19 (s, 1 H), 8.14 (dd, J = 8.2, 1.4 Hz, 1 H), 7.79-7.72 (m, 3 H), 7.65 (s, 1 H), 7.56 (d, J = 2.7 Hz, 1 H), 7.22 (t, J = 8.1 Hz, 1 H), 6.41 (dd, J = 8.0, 1.4 Hz, 1 H), 6.17 (s, 2 H), 3.86 (q, J = 5.1, 4.3 Hz, 2 H), 3.35 (ddd, J = 13.3, 9.3, 3.6 Hz, 2 H), 2.79 (q, J = 5.8 Hz, 2 H), 1.50 (ddd, J = 13.6, 9.4, 4.2 Hz, 2 H), 1.40 (dt, J = 13.4, 4.4 Hz, 2 H), 1.06 (s, 3 H). HRMS calcd for $C_{24}H_{27}ClN_9O_3S$ (M + H)$^+$ 556.1646, found 556.1633. | 0.005 |
| 7 | 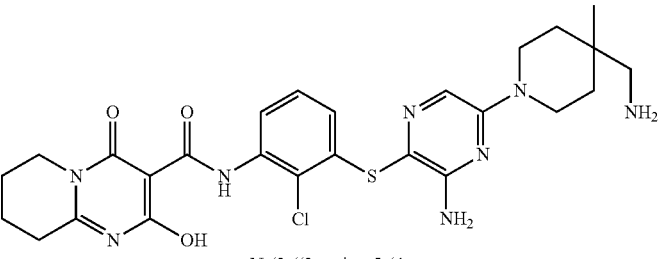<br>N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-$d_4$) δ ppm 8.31 (dd, J = 8.3, 1.3 Hz, 1 H), 7.76 (s, 1 H), 7.29 (t, J = 8.2 Hz, 1 H), 6.75 (dd, J = 7.9, 1.3 Hz, 1 H), 4.10 (dt, J = 13.9, 4.8 Hz, 2 H), 3.99 (t, J = 6.1 Hz, 2 H), 3.56 (ddd, J = 13.7, 9.3, 4.2 Hz, 2 H), 3.34 (s, 2 H), 2.94 (s, 2 H), 2.09-1.96 (m, 2H), 1.98-1.88 (m, 2 H), 1.73-1.56 (m, 4 H), 1.22 (s, 3 H). HRMS calcd for $C_{26}H_{32}ClN_8O_3S$ (M + H)$^+$ 571.2007, found 571.1993. | 0.006 |
| 8 | 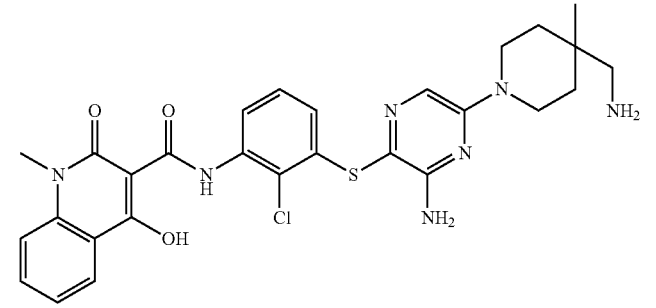 [SMILES: Cn1c(=O)c(C(=O)Nc2cccc(Sc3ncc(N4CCC(C)(CN)CC4)nc3N)c2Cl)c(O)c2ccccc21]<br>N-(3-((3-amino-5-(4-(aminomethyl)-4-methylpiperidin-1-yl)pyrazin-2-yl)thio)-2-chlorophenyl)-4-hydroxy-1-methyl-2-oxo-1,2-dihydroquinoline-3-carboxamide | as HCl salt: $^1$H NMR (400 MHz, Methanol-$d_4$) δ ppm 13.15 (s, 1 H), 8.33 (dd, J = 8.3, 1.4 Hz, 1 H), 8.24 (dd, J = 8.0, 1.5 Hz, 1 H), 7.83 (ddd, J = 8.6, 7.1, 1.6 Hz, 1 H), 7.67 (s, 1 H), 7.65 (d, J = 8.6 Hz, 1 H), 7.40 (t, J = 7.6 Hz, 1 H), 7.24 (t, J = 8.1 Hz, 1 H), 6.64 (dd, J = 8.0, 1.3 Hz, 1 H), 4.08 (dt, J = 14.0, 4.7 Hz, 2 H), 3.78 (s, 3 H), 3.56-3.43 (m, 2 H), 2.92 (s, 2H), 1.61 (dt, J = 8.6, 4.4 Hz, 4 H), 1.21 (s, 3H). HRMS calcd for $C_{28}H_{31}ClN_7O_3S$ (M + H)$^+$ 580.1898, found 580.1902. | 0.044 |
| 9 | 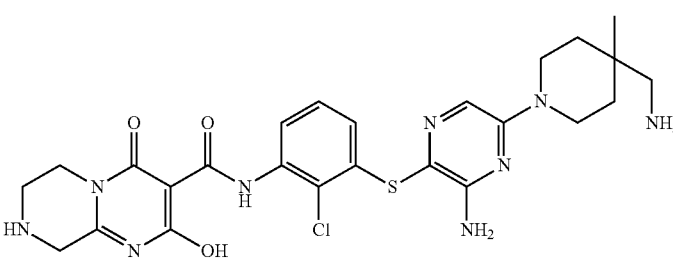<br>N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrazino[1,2-a]pyrimidine-3-carboxamide | as TFA salt: $^1$H NMR (400 MHz, DMSO-$d_6$) δ ppm 12.05 (s, 1 H), 8.09 (dd, J = 8.2, 1.4 Hz, 1 H), 7.74 (d, J = 6.3 Hz, 3 H), 7.66 (s, 1 H), 7.26 (t, J = 8.1 Hz, 1 H), 6.46 (dd, J = 8.0, 1.4 Hz, 1 H), 6.18 (s, 2 H), 4.35 (s, 2 H), 4.04 (t, J = 5.7 Hz, 2 H), 3.93-3.82 (m, 2 H), 3.54 (t, J = 5.8 Hz, 2 H), 2.80 (d, J = 5.9 Hz, 2 H), 1.50 (ddd, J = 13.4, 9.1, 4.1 Hz, 2 H), 1.41 (dt, J = 13.3, 4.5 Hz, 2 H), 1.07 (s, 3 H). HRMS calcd for $C_{25}H_{31}ClN_9O_3S$ (M + H)$^+$ 572.1959, found 572.1971. | 0.007 |

TABLE 1-continued

| Example | Compound | Characterization | IC$_{50}$ (μM) |
|---|---|---|---|
| 10 | 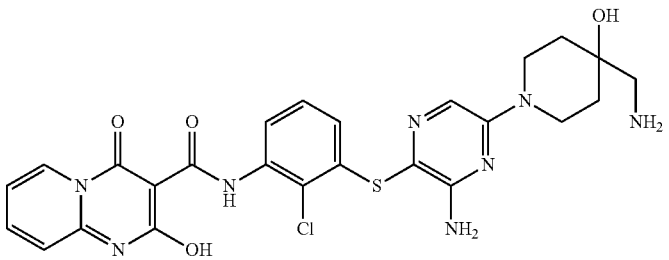 [SMILES: NCC1(O)CCN(c2cnc(Sc3cccc(NC(=O)c4c(O)nc5ccccn5c4=O)c3Cl)c(N)n2)CC1]  N-(3-((3-amino-5-(4-(aminomethyl)-4-hydroxypiperidin-1-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ ppm 12.15 (s, 1 H), 9.07 (d, J = 6.9 Hz, 1 H), 8.21 (ddd, J = 8.6, 5.1, 1.6 Hz, 2 H), 8.00 (d, J = 7.4 Hz, 3 H), 7.69 (s, 1 H), 7.59 (d, J = 8.7 Hz, 1 H), 7.49-7.42 (m, 1 H), 7.23 (t, J = 8.1 Hz, 1 H), 6.43 (dd, J = 8.1, 1.4 Hz, 1 H), 4.08-4.02 (m, 2 H), 3.33 (ddd, J = 13.6, 10.6, 3.5 Hz, 2 H), 2.82 (q, J = 5.7 Hz, 2 H), 1.69-1.51 (m, 4 H). HRMS calcd for C$_{25}$H$_{26}$N$_8$O$_4$SCl (M + H)$^+$ 569.1486, found 569.1463. | 0.006 |
| 11 | 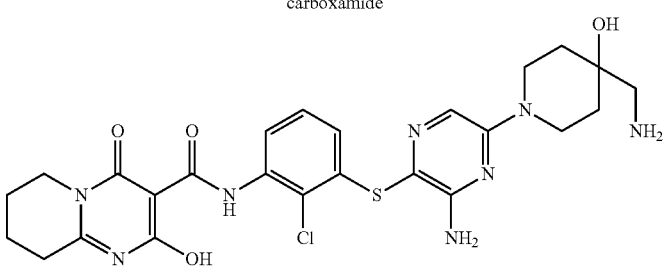  N-(3-((3-amino-5-(4-(aminomethyl)-4-hydroxypiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.30 (dd, J = 8.3, 1.3 Hz, 1 H), 7.80 (s, 1 H), 7.30 (t, J = 8.2 Hz, 1 H), 6.76 (dd, J = 8.0, 1.3 Hz, 1 H), 4.32 (d, J = 13.4 Hz, 2 H), 3.99 (t, J = 6.1 Hz, 2 H), 3.57-3.44 (m, 2 H), 3.34 (s, 2 H), 2.96 (s, 2H), 2.09-1.99 (m, 2 H), 1.97-1.88 (m, 2 H), 1.85-1.65 (m, 4 H). HRMS calcd for C$_{25}$H$_{30}$ClN$_8$O$_4$S (M + H)$^+$ 573.1799, found 573.1792. | 0.012 |
| 12 | 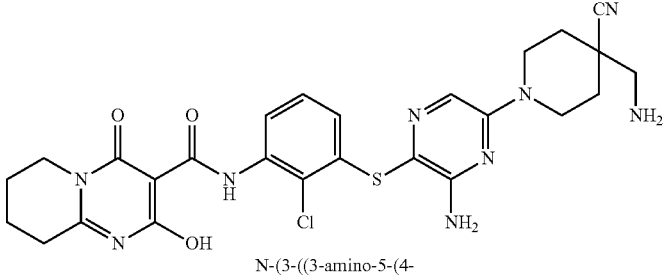  N-(3-((3-amino-5-(4-(aminomethyl)-4-cyanopiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.30 (dd, J = 8.2, 1.4 Hz, 1 H), 7.43 (s, 1 H), 7.25 (t, J = 8.1 Hz, 1 H), 6.69 (dd, J =7.9, 1.4 Hz, 1 H), 3.98 (t, J = 6.1 Hz, 2 H), 3.88 (s, 2 H), 3.56 (dt, J = 14.0, 3.5 Hz, 2 H), 3.31 m, 2H), 3.21 (td, J = 13.2, 3.0 Hz, 2 H), 2.28 (d, J = 15.0 Hz, 2 H), 2.09-1.97 (m, 4 H), 1.96-1.88 (m, 2 H). HRMS calcd for C$_{26}$H$_{29}$ClN$_9$OS (M + H)$^+$ 582.1803, found 582.1782. | 0.26 |
| 13 | 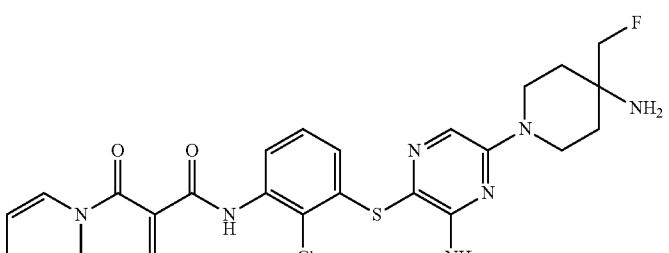  N-(3-((3-amino-5-(4-amino-4-(fluoromethyl)piperidin-1-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ 9.28-9.06 (m, 1H), 8.40-8.29 (m, 1 H), 8.28-8.13 (m, 1 H), 7.79 (s, 1 H), 7.67-7.55 (m, 1 H), 7.51-7.39 (m, 1 H), 7.36-7.16 (m, 1 H), 6.80-6.59 (m, 1 H), 4.45 (d, J = 14.0 Hz, 2 H), 3.46-3.35 (m, 2 H), 3.28-3.22 (m, 2 H), 2.14-2.01 (m, 2 H), 2.00-1.76 (m, 2 H). HRMS calcd for C$_{25}$H$_{25}$ClN$_8$O$_3$SF (M + H)$^+$ 571.1443, found 571.1410. | 0.0046 |

TABLE 1-continued

| Example | Compound | Characterization | IC$_{50}$ (μM) |
|---|---|---|---|
| 14 | 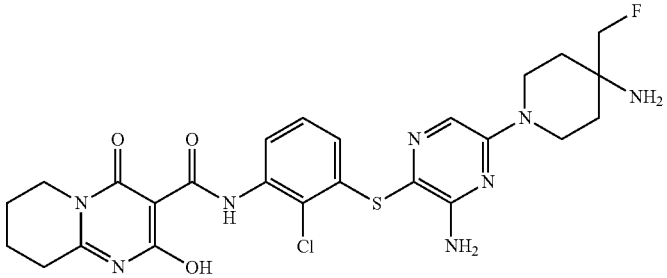 [SMILES: Nc1nc(N2CCC(N)(CF)CC2)cnc1Sc1cccc(NC(=O)c2c(O)nc3n(c2=O)CCCC3)c1Cl]<br>N-(3-((3-amino-5-(4-amino-4-(fluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.30 (d, J = 7.5 Hz, 1 H), 7.85 (s, 1 H), 7.31 (t, J = 8.2 Hz, 1 H), 6.89-6.65 (m, 1 H), 4.48 (d, J = 13.5 Hz, 2 H), 4.00 (t, J = 6.1 Hz, 2 H), 3.42 (t, J = 11.9 Hz, 2 H), 3.29 (s, 1 H), 3.24 (s, 1 H), 2.16-1.80 (m, 8 H). MS m/z (M + H)$^+$ 575.2 | 0.0059 |
| 15 | 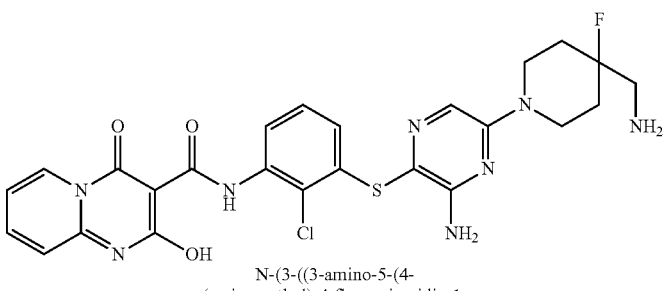<br>N-(3-((3-amino-5-(4-(aminomethyl)-4-fluoropiperidin-1-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ ppm 9.16 (d, J = 6.8 Hz, 1 H), 8.34 (d, J = 8.2 Hz, 1 H), 8.18 (t, J = 7.8 Hz, 1 H), 7.73 (s, 1 H), 7.57 (d, J = 8.8 Hz, 1 H), 7.45 (t, J = 6.9 Hz, 1 H), 7.22 (t, J = 8.1 Hz, 1 H), 6.62 (d, J = 8.0 Hz, 1 H), 4.43 (d, J = 13.5 Hz, 2 H), 3.45-3.35 (m, 2 H), 3.28-3.21 (m, 2 H), 2.14-1.99 (m, 2 H), 1.99-1.71 (m, 2 H). HRMS calcd for C$_{25}$H$_{25}$ClFN$_8$O$_3$S (M + H)$^+$ 571.1443, found 571.1427. | 0.010 |
| 16 | 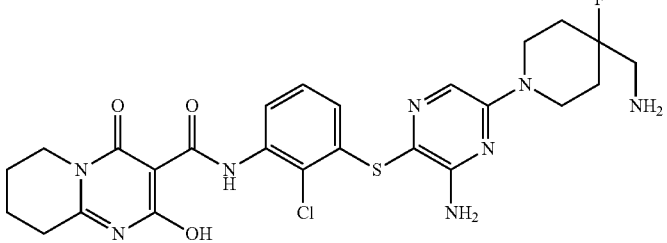<br>N-(3-((3-amino-5-(4-(aminomethyl)-4-fluoropiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.39-8.19 (m, 1 H), 7.72 (s, 1 H), 7.30-7.11 (m, 1 H), 6.73-6.49 (m, 1 H), 4.42 (d, J = 13.8 Hz, 2H), 4.05-3.89 (m, 2 H), 3.28-3.22 (m, 4 H), 2.10-2.00 (m, 6 H), 1.97-1.86 (m, 4 H). MS m/z (M + H)$^+$ 575.1. HRMS calcd for C$_{25}$H$_{29}$ClFN$_8$O$_3$S (M + H)$^+$ 575.1756, found 575.1727. | 0.008 |
| 17 | 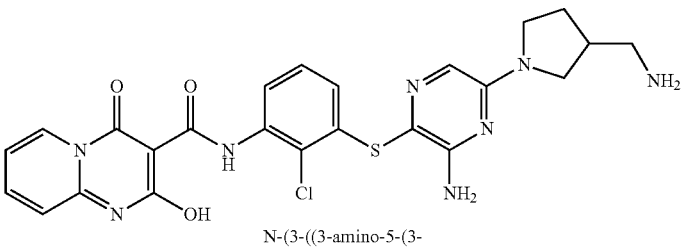<br>N-(3-((3-amino-5-(3-(aminomethyl)pyrrolidin-1-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, DMSO-d$_6$) δ ppm 12.14 (s, 1 H), 9.07 (d, J = 6.4 Hz, 1 H), 8.21 (t, J = 7.1 Hz, 2 H), 7.91 (br. s, 3 H), 7.58 (d, J = 8.5 Hz, 1 H), 7.45 (td, J = 7.0, 1.2 Hz, 1 H), 7.30 (s, 1 H), 7.27-7.19 (m, 1 H), 6.38 (d, J = 7.6 Hz, 1 H), 6.14 (br. s, 2 H), 3.68-3.57 (m, 4 H), 3.47-3.38 (m, 1 H), 3.23 (dd, J = 10.9, 6.9 Hz, 1 H), 3.01-2.85 (m, 2 H), 2.62-2.54 (m, 1 H), 2.21-2.07 (m, 1 H), 1.88-1.68 (m, 1 H). HRMS calcd for C$_{24}$H$_{24}$ClN$_8$O$_3$S (M + H)$^+$ 539.1381, found 539.1373. | 0.013 |

TABLE 1-continued

| Example | Compound | Characterization | IC$_{50}$ (μM) |
|---|---|---|---|
| 18 | 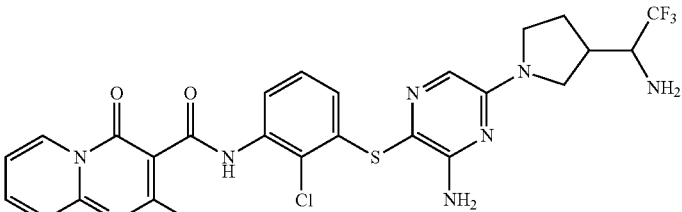<br>N-(3-((3-amino-5-(3-(1-amino-2,2,2-trifluoroethyl)pyrrolidin-1-yl)pyrazin-2-yl)thio)-2-chlorophenyl)-2-hydroxy-4-oxo-4H-pyrido[1,2-a]pyrimidine-3-carboxamide | as HCl salt. $^1$H NMR (400 MHz, Methanol-d$_4$) δ ppm 9.30-9.06 (m, 1 H), 8.43-8.04 (m, 2 H), 7.74-7.28 (m, 3 H), 7.18-7.06 (m, 1 H), 6.60-6.42 (m, 1 H), 4.43-4.33 (m, 1 H), 4.02-3.91 (m, 1 H), 3.89-3.79 (m, 1 H), 3.56-3.48 (m, 1 H), 3.43-3.36 (m, 1 H), 2.92-2.80 (m, 1 H), 2.42-2.30 (m, 1 H), 2.12-1.97 (m, 1 H). HRMS calcd for C$_{25}$H$_{23}$ClF$_3$N$_8$O$_3$S (M + H)$^+$ 607.1254, found 607.1241. | 0.789 |
| 19 | 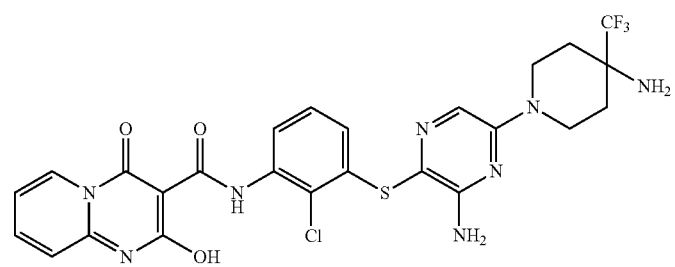 [SMILES: Nc1nc(N2CCC(N)(C(F)(F)F)CC2)cnc1Sc1cccc(NC(=O)c2c(O)nc3ccccn3c2=O)c1Cl]<br>N-(3-((3-amino-5-(4-amino-4-(trifluoromethyl)piperidin-1-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, DMSO-d$_6$) δ ppm 12.13 (s, 1 H), 9.36 (br. s, 1 H), 9.17-8.99 (m, 1 H), 8.30-8.10 (m, 2 H), 7.69 (s, 1 H), 7.58 (d, J = 8.7 Hz, 1 H), 7.45 (td, J = 7.0, 1.3 Hz, 1 H), 7.33-7.18 (m, 1 H), 6.44 (dd, J = 7.9, 1.5 Hz, 1 H), 6.25 (br. s, 1 H), 4.12 (s, 2 H), 3.63 (d, J = 10.4 Hz, 2 H), 2.17-1.81 (m, 4 H). HRMS calcd for C$_{25}$H$_{23}$ClF$_3$N$_8$O$_3$S (M + H)$^+$ 607.1254, found 607.1253. | 2.19 |
| 20 | 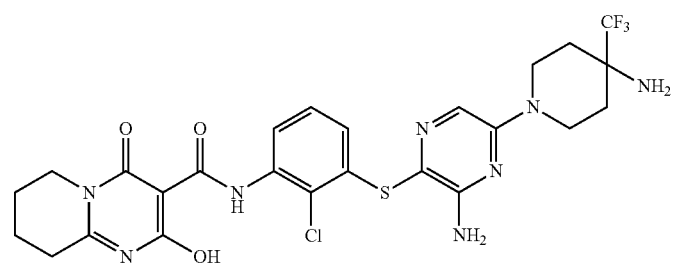 [SMILES: Nc1nc(N2CCC(N)(C(F)(F)F)CC2)cnc1Sc1cccc(NC(=O)c2c(O)nc3n(c2=O)CCCC3)c1Cl]<br>N-(3-((3-amino-5-(4-amino-4-(trifluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.32 (d, J = 8.2 Hz, 1 H), 7.78 (s, 1 H), 7.27 (t, J = 8.1 Hz, 1 H), 6.72 (d, J = 7.0 Hz, 1 H), 4.35-4.19 (m, 2 H), 4.01 (t, J = 6.1 Hz, 2 H), 3.81-3.65 (m, 2 H), 3.39-3.34 (m, 2 H), 2.45-2.29 (m, 2 H), 2.21-2.11 (m, 2 H), 2.11-2.01 (m, 2 H), 1.99-1.90 (m, 2 H). HRMS calcd for C$_{25}$H$_{27}$ClF$_3$N$_8$O$_3$S (M + H)$^+$ 611.1567, found 611.1569. | 5.0 |
| 21 | 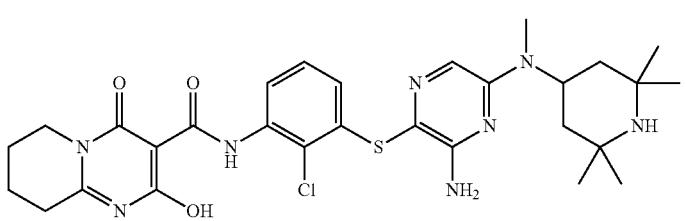 [SMILES: CN(c1cnc(Sc2cccc(NC(=O)c3c(O)nc4n(c3=O)CCCC4)c2Cl)c(N)n1)C1CC(C)(C)NC(C)(C)C1]<br>N-(3-((3-Amino-5-(methyl(2,2,6,6-tetramethylpiperidin-4-yl)amino)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.33 (d, J = 8.3 Hz, 1 H), 7.63 (s, 1 H), 7.27 (t, J = 8.2 Hz, 1 H), 6.72 (d, J = 8.0 Hz, 1 H), 3.99 (t, J = 6.1 Hz, 2 H), 3.07 (s, 3 H), 2.08-1.85 (m, 9 H), 1.64 (s, 6 H), 1.54 (s, 6 H); MS m/z (M + H)$^+$ 614.2. | 5.38 |

TABLE 1-continued

| Example | Compound | Characterization | IC$_{50}$ (μM) |
|---|---|---|---|
| 22 | 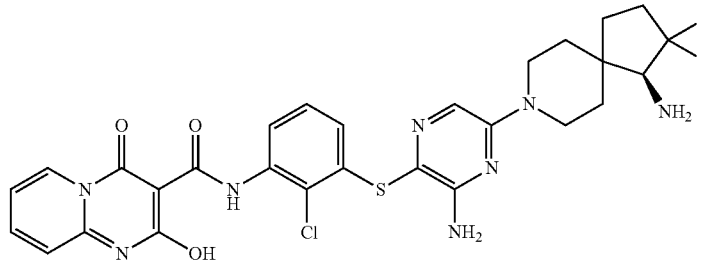

(S)-N-(3-((3-amino-5-(1-amino-2,2-difluoro-8-azaspiro[4.5]decan-8-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ ppm 9.41-9.04 (m, 1 H), 8.54-8.07 (m, 2 H), 7.80-7.45 (m, 3 H), 7.33-7.10 (m, 1 H), 6.75-6.50 (m, 1 H), 4.60-4.28 (m, 2 H), 3.73-3.62 (m, 1 H), 3.24-3.12 (m, 2 H), 2.45-2.23 (m, 3 H), 2.03-1.89 (m, 2 H), 1.74-1.57 (m, 3H). MS m/z (M + H)$^+$ 629.1. | 0.010 |
| 23 | 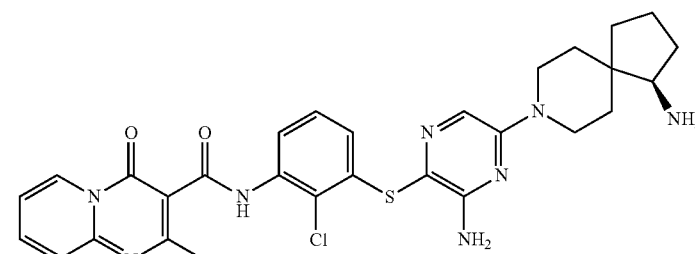

(R)-N-(3-((3-amino-5-(1-amino-8-azaspiro[4.5]decan-8-yl)pyrazin-2-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ ppm 9.16 (d, J = 7.0 Hz, 1 H), 8.36 (d, J = 8.2 Hz, 1 H), 8.20 (ddd, J = 8.7, 6.9, 1.6 Hz, 1 H), 7.76 (s, 1 H), 7.58 (d, J = 8.8 Hz, 1 H), 7.47 (t, J = 7.0 Hz, 1 H), 7.27 (t, J = 8.2 Hz, 1 H), 6.71 (d, J = 7.9 Hz, 1 H), 4.43 (d, J = 13.7 Hz, 1 H), 4.34 (d, J = 13.6 Hz, 1 H), 3.29-3.23 (m, 3 H), 2.33-2.16 (m, 1 H), 1.99-1.52 (m, 10 H), HRMS calcd for C$_{28}$H$_{30}$ClN$_8$O$_3$S (M + H)$^+$ 593.1850, found 593.1854. | 0.005 |
| 24 | 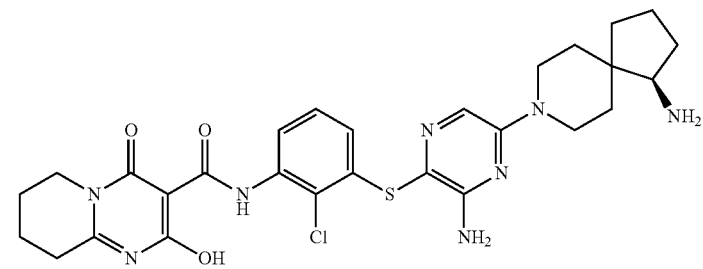 [SMILES: Nc1nc(N2CCC3(CCC[C@H]3N)CC2)cnc1Sc1cccc(NC(=O)c2c(O)nc3n(c2=O)CCCC3)c1Cl]

(R)-N-(3-((3-amino-5-(1-amino-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, DMSO-d$_6$) δ ppm 12.24 (s, 1 H), 8.13 (dd, J = 8.2, 1.4 Hz, 1 H), 8.04 (d, J = 6.5 Hz, 3 H), 7.68 (s, 1 H), 7.24 (t, J = 8.1 Hz, 1 H), 6.44 (dd, J = 8.0, 1.4 Hz, 1 H), 4.26-4.15 (m, 2 H), 3.87 (t, J = 6.1 Hz, 2 H), 3.16-2.98 (m, 3 H), 2.89 (t, J = 6.5 Hz, 2 H), 2.05 (m, 1 H), 1.97-1.86 (m, 2 H), 1.85-1.61 (m, 8 H), 1.59-1.29 (m, 3 H), HRMS calcd for C$_{28}$H$_{34}$ClN$_8$O$_3$S (M + H)$^+$ 597.2163, found 597.2171. | 0.001 |

Example 25

(5-Methyl-2-oxo-1,3-dioxol-4-yl)methyl ((1-(6-amino-5-((2-chloro-3-(2-hydroxy-4-oxo-4H-pyrido[1,2-a]pyrimidine-3-carboxamido)phenyl)thio)pyrazin-2-yl)-4-methylpiperidin-4-yl)methyl) carbamate

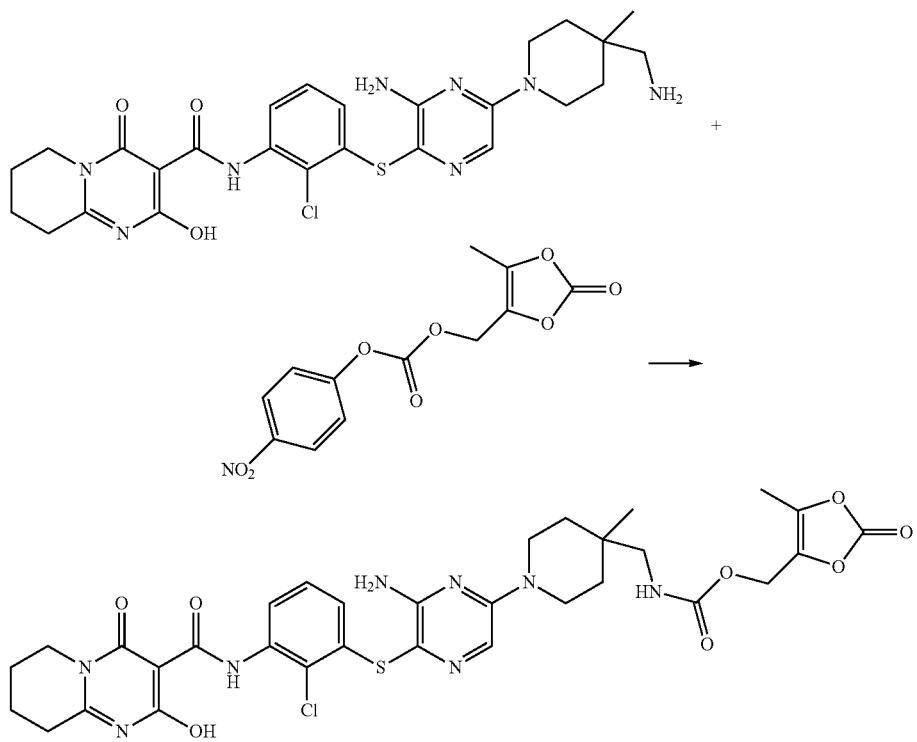

To a DMSO (1 mL) solution of N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide (50 mg, 0.078 mmol) was added DIPEA (0.055 mL, 0.313 mmol) and (5-methyl-2-oxo-1,3-dioxol-4-yl)methyl(4-nitrophenyl)carbonate (24.2 mg, 0.082 mmol). After stirring at RT for 1 h, the crude material was filtered and was purified by HPLC (45-70% MeCN/water, 0.1% formic acid), to give the title compound (28 mg). $^1$H NMR (400 MHz, Acetonitrile-$d_3$) δ ppm 15.15 (s, 1H), 12.14 (s, 1H), 9.00 (d, J=7.1 Hz, 1H), 8.19 (d, J=8.2 Hz, 1H), 8.02 (ddd, J=8.9, 6.9, 1.8 Hz, 1H), 7.62 (s, 1H), 7.54 (d, J=8.9 Hz, 1H), 7.32 (t, J=7.0 Hz, 1H), 7.19 (t, J=8.1 Hz, 1H), 6.54 (dd, J=8.0, 1.7 Hz, 1H), 5.78 (t, J=6.8 Hz, 1H), 5.20 (s, 2H), 4.81 (s, 2H), 3.83 (dt, J=13.4, 5.1 Hz, 2H), 3.41 (ddd, J=13.5, 9.4, 3.6 Hz, 2H), 3.06 (d, J=6.7 Hz, 2H), 2.12 (s, 3H), 1.48 (ddd, J=13.3, 8.7, 3.8 Hz, 2H), 1.36 (dt, J=13.6, 4.7 Hz, 2H), 0.97 (s, 3H). HRMS calcd for $C_{32}H_{32}ClN_8O_8S$ (M+H)$^+$ 723.1752, found 723.1728. The $IC_{50}$=0.08 μM.

Example 26

(S)—N-(3-((3-Amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide

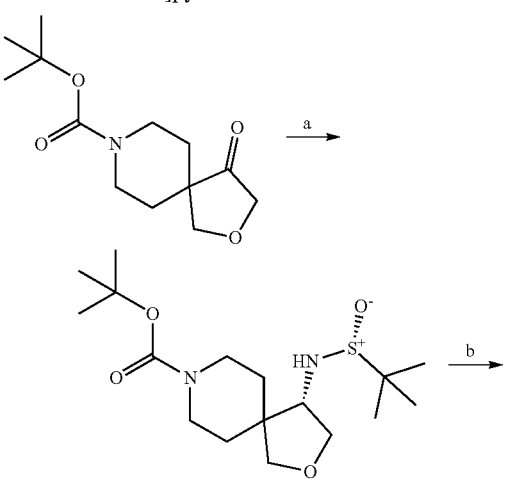

-continued

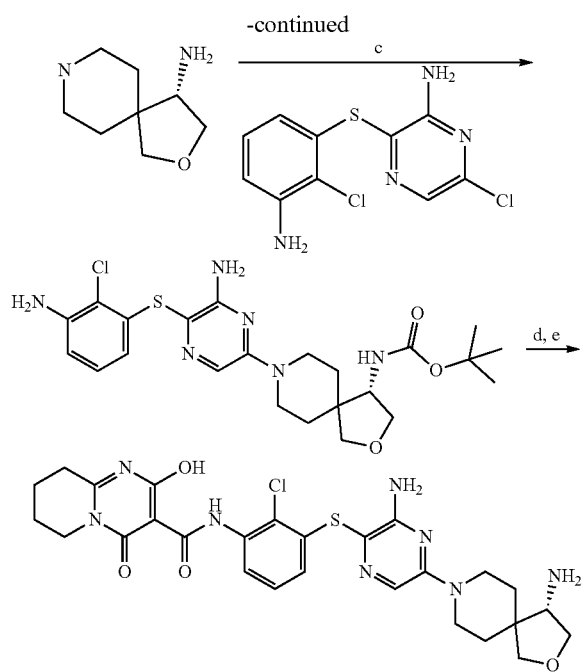

Step a: To a 20 mL microwave vial containing a solution of tert-butyl 4-oxo-2-oxa-8-azaspiro[4.5]decane-8-carboxylate (220 mg, 0.86 mmol) in THF (4 mL) was added (R)-2-methylpropane-2-sulfinamide (209 mg, 1.72 mmol) followed by titanium tetraethoxide (0.723 mL, 3.45 mmol). The vial was capped and heated at 90° C. for 1 h. The mixture was cooled to 0° C., then LiBH$_4$ was added (23 mg, 1.06 mmol). The reaction mixture stirred 30 min, then was quenched by the slow addition of MeOH until frothing ceased. The mixture was diluted with MeOH, then concentrated under reduced pressure. The residue was diluted with brine (with sonication). The mixture was extracted EtOAc (4×10 mL), then the organics were washed with brine, dried with Na$_2$SO$_4$, filtered, and concentrated under reduced pressure. Silica gel flash chromatography (0-100% EtOAc/heptane) afforded (S)-tert-butyl 4-((R)-1,1-dimethylethylsulfinamido)-2-oxa-8-azaspiro[4.5]decane-8-carboxylate (170 mg), MS m/z 361.1 (M+H)$^+$.

Step b: To a solution of (S)-tert-butyl 4-((R)-1,1-dimethylethylsulfinamido)-2-oxa-8-azaspiro[4.5]decane-8-carboxylate (800 mg, 2.22 mmol) in MeOH (20 mL), was added 4 M HCl in dioxane (3.33 mL, 13.3 mmol) and heated to 40° C. for 20 min. The reaction mixture was concentrated under reduced pressure with three further additions of MeOH to obtain (S)-2-oxa-8-azaspiro[4.5]decane-4-amine HCl salt, MS m/z 157.2 (M+H)$^+$. The crude residue was taken to the next step with no further purification.

Alternate procedure: To a solution of (S)-tert-butyl 4-((R)-1,1-dimethylethylsulfinamido)-2-oxa-8-azaspiro[4.5]decane-8-carboxylate (891 mg, 2.47 mmol) in MeOH (9 mL), added 4 M HCl in dioxane (3.71 mL, 14.8 mmol) and heated to 40° C. for 20 min. The reaction mixture was concentrated under reduced pressure, and then triturated from MeCN with sonication. The mixture was filtered through 0.45 um PTFE membrane to obtain (S)-2-oxa-8-azaspiro[4.5]decane-4-amine as the bis-HCl salt (510 mg). $^1$H NMR (400 MHz, Methanol-d$_4$) δ ppm 4.19 (dd, J=10.8, 5.5 Hz, 1H), 3.92 (d, J=9.4 Hz, 1H), 3.88-3.81 (m, 2H), 3.69 (dd, J=5.6, 2.6 Hz, 1H), 3.48-3.34 (m, 2H), 3.20-3.03 (m, 2H), 2.10-1.97 (m, 2H), 1.94-1.84 (m, 2H). MS m/z 157.2 (M+H)$^+$.

Step c: A suspension of 3-((3-amino-2-chlorophenyl)thio)-6-chloropyrazin-2-amine (0.10 g, 0.24 mmol), (S)-2-oxa-8-azaspiro[4.5]decan-4-amine dihydrochloride (0.084 g, 0.29 mmol) and DIPEA (0.5 mL, 2.7 mmol) in DMSO (0.8 mL) was heated at 120° C. for 1 h. After cooling to RT and the addition of MeCN, a brown precipitate was collected by filtration and purified by trituration with MeCN/MeOH (approx. 4 mL, 9:1) to give crude (S)-8-(6-amino-5-((3-amino-2-chlorophenyl)thio)pyrazin-2-yl)-2-oxa-8-azaspiro[4.5]decan-4-amine as a brown solid. This material was suspended in a DCM/DMF mixture (1.1 mL, 10:1) and added to a solution of DIPEA (0.04 mL, 0.23 mmol), and Boc$_2$O (0.10 g, 0.48 mmol). After stirring for 60 h at RT and then at 40° C. for 5 h, the reaction mixture was concentrated under reduced pressure. The resulting solid was dissolved in EtOAc, washed with sat. aq. NH$_4$Cl followed by water. The organics were dried over MgSO$_4$, filtered and concentrated under reduced pressure to give tert-butyl(S)-(8-(6-amino-5-((3-amino-2-chlorophenyl)thio)pyrazin-2-yl)-2-oxa-8-azaspiro[4.5]decan-4-yl)carbamate, as a brown solid (0.11 g) that was used without further purification. MS m/z 507.3 (M+H)$^+$.

Steps d and e were performed according to Example 1 using 4 M HCl in dioxane to afford (S)—N-(3-((3-amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide as HCl salt. $^1$H NMR (400 MHz, Methanol-d$_4$) δ ppm 8.25 (d, J=7.1 Hz, 1H), 7.60 (s, 1H), 7.16 (t, J=8.1 Hz, 1H), 6.51 (d, J=8.0 Hz, 1H), 4.36-4.13 (m, 3H), 4.02-3.96 (m, 2H), 3.90 (d, J=9.2 Hz, 1H), 3.82 (dd, J=10.6, 2.6 Hz, 1H), 3.61-3.54 (m, 1H), 3.37-3.34 (m, 1H), 3.27-3.25 (m, 1H), 3.23-3.14 (m, 1H), 2.95 (t, J=6.5 Hz, 2H), 2.06-1.99 (m, 2H), 1.97-1.89 (m, 2H), 1.81-1.67 (m, 3H). HRMS calcd for: C$_{27}$H$_{32}$ClN$_8$O$_4$S (M+H)$^+$599.1956, found 599.1947. IC$_{50}$=0.018 μM.

Example 27

N-(3-((3-Amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide

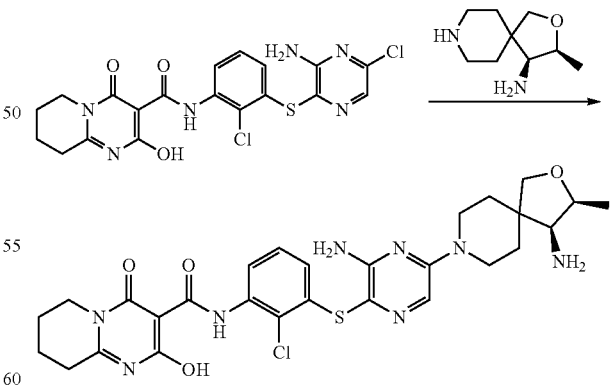

A solution of N-(3-((3-amino-5-chloropyrazin-2-yl)thio)-2-chlorophenyl)-2-hydroxy-4-oxo-6,7,8,9-tetrahydro-4H-pyrido[1,2-a]pyrimidine-3-carboxamide (0.13 g, 0.27 mmol), (3S,4S)-3-methyl-2-oxa-8-azaspiro[4.5]decan-4-amine (0.20 g, 0.81 mmol, approx. 70% pure) and DIPEA (0.1 mL, 0.55 mmol) in DMF (2 mL) was radiated in a microwave reactor for 90 min at 100° C. After cooling to RT the reaction mixture was mixed with diethyl ether and the resulting brown precipitate was collected by filtration. The precipitate was purified by reverse phase HPLC (15-40% MeCN in water, 0.1% TFA modifier) to give the title compound as a TFA salt. The pure fractions were concentrated under reduced pressure and then diluted with HCl (1.25 M in MeOH) and evaporated (3×) to give the titled compound as the HCl salt (56 mg).

The following compounds identified in Table 2 were made using the procedure or modifications to the procedure as exemplified by Example 27 with N-(3-((3-amino-5-chloropyrazin-2-yl)thio)-2-chlorophenyl)-2-hydroxy-4-oxo-6,7,8,9-tetrahydro-4H-pyrido[1,2-a]pyrimidine-3-carboxamide and the appropriate amine.

TABLE 2

| Example | Compound | Characterization | IC$_{50}$ (μM) |
|---|---|---|---|
| 27 | N-(3-((3-amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt:: $^1$H NMR (400 MHz, Methanol-d$_4$) δ ppm 8.32 (d, J = 8.3 Hz, 1 H), 7.75 (s, 1 H), 7.24 (t, J = 8.2 Hz, 1 H), 6.67 (d, J = 8.0 Hz, 1 H), 4.44-4.21 (m, 3 H), 4.06-3.93 (m, 3 H), 3.88 (d, J = 9.2 Hz, 1 H), 3.47 (d, J = 4.0 Hz, 1 H), 3.27-3.17 (m, 2 H), 3.01-2.91 (m, 1 H), 2.07-1.99 (m, 2 H), 1.98-1.79 (m, 6 H), 1.78-1.69 (m, 1 H), 1.32 (d, J = 6.5 Hz, 3H). HRMS calcd for C$_{28}$H$_{34}$ClN$_8$O$_4$S (M + H)$^+$ 613.2112, found 613.2142. | 0.023 |
| 28 | (R)-N-(3-((3-amino-5-(1-amino-3,3-difluoro-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.31 (d, J = 8.1 Hz, 1 H), 7.72 (s, 1 H), 7.23 (t, J = 8.1 Hz, 1 H), 6.65 (d, J = 7.9 Hz, 1 H), 4.49 (d, J = 13.8 Hz, 1 H), 4.40 (d, J = 13.7 Hz, 1 H), 3.98 (t, J = 6.0 Hz, 2 H), 3.60 (t, J = 7.9 Hz, 1 H), 3.26-3.12 (m, 2 H), 3.00-2.89 (m, 1 H), 2.88-2.71 (m, 1 H), 2.71-2.55 (m, 1 H), 2.50-2.32 (m, 2 H), 2.07-1.99 (m, 2 H), 1.92 (q, J = 5.6 Hz, 4 H), 1.71 (dt, J = 15.0, 12.6 Hz, 3 H), HRMS calcd for C$_{28}$H$_{32}$ClF$_2$N$_8$O$_3$S (M + H)$^+$ 633.1975, found 633.1967. | 0.042 |
| 29 | N-(3-((3-amino-5-((3S,4S)-4-amino-3-ethyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.30 (d, J = 7.1 Hz, 1 H), 7.72 (s, 1 H), 7.24 (t, J = 8.2 Hz, 1 H), 6.66 (d, J = 6.9 Hz, 1 H), 4.40-4.23 (m, 2 H), 4.06-3.95 (m, 3 H), 3.90 (d, J = 9.3 Hz, 1 H), 3.49 (dd, J = 9.3, 2.7 Hz, 1 H), 3.34 (s, 2 H), 3.24-3.16 (m, 1 H), 3.01-2.90 (m, 1 H), 2.06-1.99 (m, 5 H), 1.96-1.81 (m, 5 H), 1.77-1.70 (m, 1 H), 1.68-1.54 (m, 2 H), 1.32-1.27 (m, 1 H), 1.09 (t, J = 7.3 Hz, 3 H). HRMS calcd for C$_{29}$H$_{36}$ClN$_8$O$_4$S (M + H)$^+$ 627.2260. found 627.2271. | 0.012 |

TABLE 2-continued

| Example | Compound | Characterization | IC$_{50}$ (μM) |
|---|---|---|---|
| 30 | 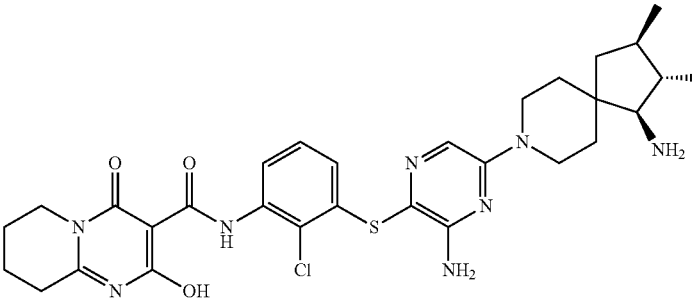<br>N-(3-((3-amino-5-((1S,2S,3R)-1-amino-2-fluoro-3-methyl-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, Methanol-d$_4$) δ ppm 8.31 (d, J = 8.2 Hz, 1 H), 7.76 (s, 1 H), 7.29 (t, J = 8.1 Hz, 1 H), 6.74 (d, J = 7.9 Hz, 1 H), 4.68-4.37 (m, 3 H), 3.99 (t, J = 6.1 Hz, 2 H), 3.38 (dd, J = 15.2, 8.5 Hz, 1 H), 3.27-3.12 (m, 2 H), 2.99-2.91 (m, 1 H), 2.37-2.24 (m, 2 H), 2.07-1.99 (m, 2 H), 1.97-1.88 (m, 3 H), 1.77-1.63 (m, 2 H), 1.61-1.55 (m, 1 H), 1.47-1.44 (m, 1 H), 1.32 (d, J = 6.5 Hz, 1 H), 1.21 (d, J = 6.0 Hz, 3 H).<br>HRMS calcd for C$_{29}$H$_{35}$ClFN$_8$O$_3$S (M + H)$^+$ 629.2225, obtained: 629.2228 | 0.016 |

The following compounds identified in Table 3 were made using the procedure or modifications to the procedure as exemplified for Example 1.

TABLE 3

| Example | Compound | Characterization | IC$_{50}$ (μM) |
|---|---|---|---|
| 31 | 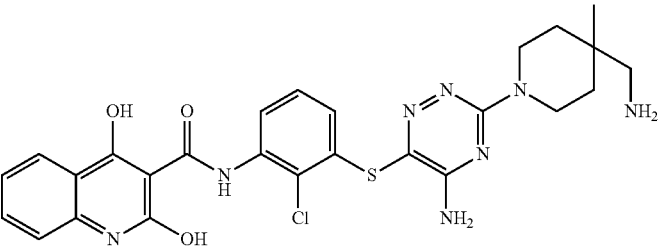 [SMILES: CC1(CN)CCN(c2nnc(Sc3cccc(NC(=O)c4c(O)nc5ccccc5c4O)c3Cl)c(N)n2)CC1]<br>N-(3-((5-amino-3-(4-(aminomethyl)-4-methylpiperidin-1-yl)-1,2,4-triazin-yl)thio)-2-chlorophenyl)-2,4-dihydroxyquinoline-3-carboxamide | as TFA salt: $^1$H NMR (400 MHz, Methanol-d$_4$) δ ppm 13.03 (s, 1 H), 8.59 (d, J = 7.2 Hz, 1 H), 8.14 (d, J = 8.1 Hz, 1 H), 7.72 (t, J = 7.7 Hz, 1 H), 7.52-7.29 (m, 4 H), 3.99 (br, s, 2 H), 3.60-3.47 (m, 2 H), 2.93 (s, 2 H), 1.75-1.57 (m, 4 H), 1.20 (s, 3 H).<br>HRMS calcd for C$_{26}$H$_{28}$ClN$_8$O$_3$S (M + H)$^+$ 567.1694, found 567.1707. | 0.038 |
| 32 | 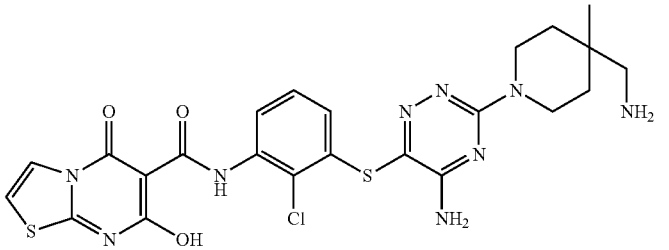 [SMILES: CC1(CN)CCN(c2nnc(Sc3cccc(NC(=O)c4c(O)nc5sccn5c4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-7-hydroxy-5-oxo-5H-thiazolo[3,2-a]pyrimidine-6-carboxamide | as HCl salt: $^1$H NMR (400 MHz, DMSO-d$_6$) δ ppm 15.16 (s, 1 H), 12.06 (s, 1 H), 9.11 (s, 1 H), 8.38 (d, J = 8.2 Hz, 1 H), 8.19 (d, J = 4.8 Hz, 1 H), 8.05 (d, J = 6.2 Hz, 3 H), 7.62 (d, J = 4.8 Hz, 1 H), 7.46 (t, J = 8.1 Hz, 1 H), 7.27 (s, 1 H), 3.91 (m, 2 H), 3.54 (m, 2 H), 2.77 (m, 2 H), 1.57 (m, 2 H), 1.50-1.36 (m, 2 H), 1.07 (s, 3 H).<br>HRMS calcd for C$_{23}$H$_{25}$ClN$_9$O$_3$S$_2$ (M + H)$^+$ 574.1210, found 574.1165. | 0.008 |

TABLE 3-continued

| Example | Compound | Characterization | IC$_{50}$ (μM) |
|---|---|---|---|
| 33 | N-(3-((5-amino-3-(4-(aminomethyl)-4-methylpiperidin-1-yl)-1,2,4-triazin-6-yl)thio)-2-chlorophenyl)-2-hydroxy-4-oxo-4H-pyrido[1,2-a]pyrimidine-3-carboxamide | $^1$H NMR (400 MHz, Methanol-d$_4$) δ ppm 9.20-9.07 (m, 1 H), 8.61 (dd, J = 7.0, 2.9 Hz, 1 H), 8.17 (ddd, J = 8.6, 6.9, 1.6 Hz, 1 H), 7.57 (d, J = 8.8 Hz, 1 H), 7.48-7.35 (m, 3 H), 3.98 (br. s, 2 H), 3.63-3.49 (m, 2 H), 2.91 (s, 2 H), 1.71-1.52 (m, 4 H), 1.18 (s, 3 H). HRMS calcd for C$_{25}$H$_{27}$ClN$_9$O$_5$S (M + H)$^+$ 568.1646, found 568.1642. | 0.010 |
| 34 | N-(3-((5-amino-3-(4-(aminomethyl)-4-methylpiperidin-1-yl)-1,2,4-triazin-6-yl)thio)-2-chlorophenyl)-2-hydroxy-4-oxo-4H-pyrazino[1,2-a]pyrimidine-3-carboxamide | as HCl salt: $^1$H NMR (400 MHz, DMSO-d$_6$) δ ppm 15.03 (s, 1 H), 12.10 (s, 1 H), 9.15 (d, J = 1.2 Hz, 1 H), 8.81 (dd, J = 4.7, 1.2 Hz, 1 H), 8.40 (q, J = 3.5, 2.9 Hz, 2 H), 7.99 (d, J = 6.4 Hz, 3 H), 7.48 (t, J = 8.1 Hz, 1 H), 7.30 (s, 1 H), 3.90 (s, 2 H), 2.77 (d, J = 5.8 Hz, 2 H), 1.70-1.32 (m, 4 H), 1.07 (s, 3 H). HRMS calcd for C$_{24}$H$_{26}$ClN$_{10}$O$_3$S (M + H)$^+$ 569.1599, found 569.1626. | 0.014 |
| 35 | N-(3-((5-amino-3-(4-(aminomethyl)-4-methylpiperidin-1-yl)-1,2,4-triazin-6-yl)thio)-2-chlorophenyl)-7-hydroxy-5-oxo-1,5-dihydroimidazo[1,2-a]pyrimidine-6-carboxamide | as HCl salt: $^1$H NMR (400 MHz, DMSO-d$_6$) δ ppm 14.85 (s, 1 H), 13.35 (s, 1 H), 12.26 (s, 1 H), 9.35 (s, 1 H), 8.67 (s, 1 H), 8.43 (d, J = 8.2 Hz, 1 H), 8.20 (d, J = 6.0 Hz, 3 H), 7.74 (d, J = 2.5 Hz, 1 H), 7.58 (d, J = 2.5 Hz, 1 H), 7.45 (t, J = 8.0 Hz, 1 H), 7.34 (d, J = 7.9 Hz, 1 H), 3.88 (m, 2 H), 3.55 (m, 2 H), 2.75 (m, 2 H), 1.58 (m, 2 H), 1.44 (m, 2 H), 1.07 (s, 3 H). HRMS calcd for C$_{23}$H$_{26}$ClN$_{10}$O$_3$S (M + H)$^+$ 557.1599, found 557.1614. | 0.035 |
| 36 | N-(3-((5-amino-3-(4-(aminomethyl)-4-methylpiperidin-1-yl)-1,2,4-triazin-6-yl)thio)-2-chlorophenyl)-2-hydroxy-4-oxo-6,7,8,9-tetrahydro-4H-pyrido[1,2-a]pyrimidine-3-carboxamide | as TFA salt: $^1$H NMR (400 MHz, Methanol-d$_4$) δ ppm 12.24 (d, J = 3.2 Hz, 1 H), 8.51 (dt, J = 6.7, 2.4 Hz, 1 H), 7.34 (q, J = 2.8, 1.9 Hz, 2 H), 3.92 (t, J = 6.3 Hz, 4 H), 3.48 (ddd, J = 13.7, 8.8, 4.4 Hz, 2 H), 2.95-2.82 (m, 4 H), 2.02-1.93 (m, 2 H), 1.88 (q, J = 6.1 Hz, 2H), 1.57 (q, J = 5.0 Hz, 4 H), 1.14 (s, 3 H). HRMS calcd for C$_{25}$H$_{31}$ClN$_9$O$_3$S (M + H)$^+$ 572.1959, found 572.1947. | 0.012 |

TABLE 3-continued

| Example | Compound | Characterization | IC$_{50}$ (µM) |
|---|---|---|---|
| 37 | 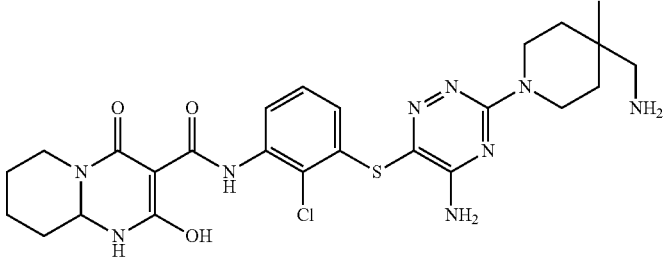 [SMILES: CC1(CN)CCN(c2nnc(Sc3cccc(NC(=O)C4=C(O)NC5CCCCN5C4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-2-hydroxy-4-oxo-4,6,7,8,9,9a-hexahydro-1H-pyrido[1,2-a]pyrimidine-3-carboxamide | $^{1}$H NMR (400 MHz, Methanol-d$_4$) δ ppm 8.17 (dd, J = 8.3, 1.5 Hz, 1 H), 7.12 (t, J = 8.2 Hz, 1 H), 6.54 (dd, J = 8.0, 1.3 Hz, 1 H), 4.71-4.61 (m, 1 H), 4.42 (ddt, J = 13.5, 4.1, 2.1 Hz, 1 H), 4.21 (dt, J = 13.8, 4.7 Hz, 2 H), 3.49 (ddd, J = 13.7, 9.8, 3.6 Hz, 2 H), 2.70-2.56 (m, 3 H), 1.97-1.83 (m, 2 H), 1.75-1.38 (m, 8 H), 1.09 (s, 3 H). HRMS calcd for C$_{25}$H$_{33}$ClN$_9$O$_3$S (M + H)$^+$ 574.2116, found 574.2100. | 0.006 |
| 38 | 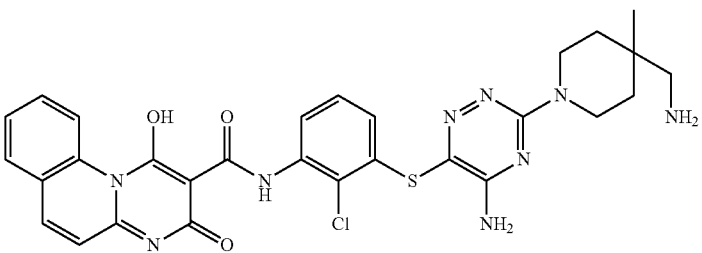 [SMILES: CC1(CN)CCN(c2nnc(Sc3cccc(NC(=O)c4c(O)n5c(ccc6ccccc65)nc4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-3-hydroxy-1-oxo-1H-pyrimido[1,2-a]quinoline-2-carboxamide | as TFA salt: $^{1}$H NMR (400 MHz, DMSO-d$_6$) δ ppm 12.27 (s, 1 H), 9.49 (s, 1 H), 8.44 (d, J = 9.1 Hz, 1 H), 8.37 (d, J = 6.6 Hz, 1 H), 8.08 (dd, J = 7.8, 1.5 Hz, 1 H), 7.86 (ddd, J = 8.9, 7.3, 1.6 Hz, 1 H), 7.77 (s, 3 H), 7.75-7.70 (m, 1 H), 7.43 (d, J = 10.2 Hz, 1 H), 7.40 (s, 1 H), 3.50 (s, 2 H), 2.79 (d, J = 5.7 Hz, 2 H), 1.58-1.47 (m, 2 H), 1.42 (dd, J = 9.1, 5.2 Hz, 2 H), 1.06 (s, 3 H). HRMS calcd for C$_{29}$H$_{29}$ClN$_9$O$_3$S (M + H)$^+$ 618.1803, found 618.1801. | 0.015 |
| 39 | 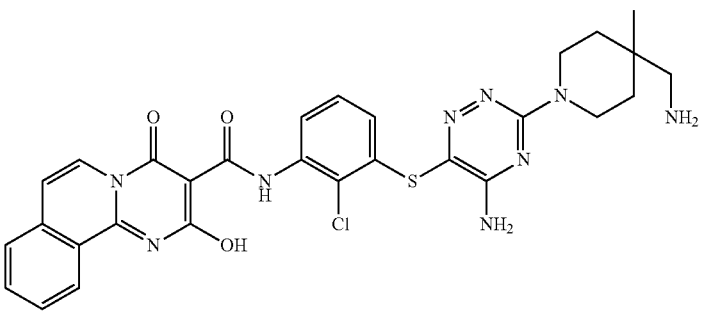 [SMILES: CC1(CN)CCN(c2nnc(Sc3cccc(NC(=O)c4c(O)nc5c6ccccc6ccn5c4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-2-hydroxy-4-oxo-4H-pyrimido[2,1-a]isoquinoline-3-carboxamide | as TFA salt: $^{1}$H NMR (400 MHz, DMSO-d$_6$) δ ppm 15.10 (s, 1 H), 12.28 (s, 1 H), 8.90 (d, J = 8.3 Hz, 1 H), 8.77 (d, J = 7.6 Hz, 1 H), 8.38 (d, J = 8.2 Hz, 1 H), 8.06 (d, J = 1.9 Hz, 1 H), 8.03 (dd, J = 7.9, 1.1 Hz, 1 H), 7.87 (ddd, J = 8.3, 6.7, 1.7 Hz, 1 H), 7.78 (s, 3H), 7.71 (d, J = 7.7 Hz, 1 H), 7.44 (t, J = 8.1 Hz, 1 H), 3.93 (s, 2 H), 2.79 (d, J = 5.7 Hz, 2H), 1.59-1.47 (m, 2 H), 1.42 (dd, J = 9.2, 5.2 Hz, 2 H), 1.06 (s, 3 H). HRMS calcd for C$_{29}$H$_{29}$ClN$_9$O$_3$S (M + H)$^+$ 618.1803, found 618.1796. | 0.013 |
| 40 | 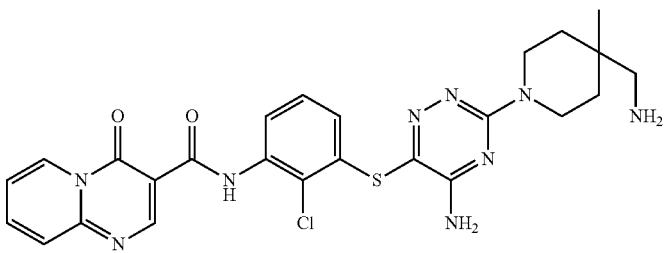 [SMILES: CC1(CN)CCN(c2nnc(Sc3cccc(NC(=O)c4cnc5ccccn5c4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-4-oxo-4H-quinolizine-3-carboxamide | as HCl salt: $^{1}$H NMR (400 MHz, Methanol-d$_4$) δ ppm 9.44 (d, J = 7.2 Hz, 1 H), 8.82-8.64 (m, 2 H), 8.07-7.88 (m, 2 H), 7.54 (t, J = 7.0 Hz, 1 H), 7.49-7.37 (m, 2 H), 7.17 (d, J = 8.6 Hz, 1 H), 4.00 (br, s, 2 H), 3.59-3.50 (m, 2 H), 2.93 (s, 2 H), 1.73-1.56 (m, 4 H), 1.20 (s, 3 H). HRMS calcd for C$_{26}$H$_{28}$ClN$_8$O$_2$S (M + H)$^+$ 551.1744, found 551.1727. | 0.173 |

TABLE 3-continued

| Example | Compound | Characterization | IC$_{50}$ (μM) |
|---|---|---|---|
| 41 | 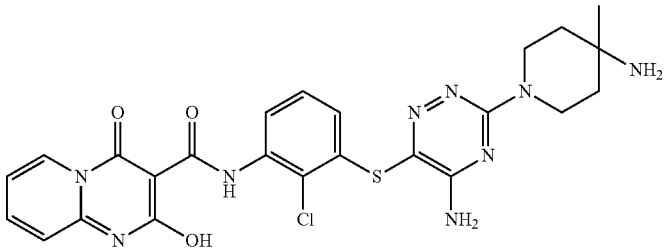 [SMILES: CC1(N)CCN(c2nnc(Sc3cccc(NC(=O)c4c(O)nc5ccccn5c4=O)c3Cl)c(N)n2)CC1]<br>N-(3-((5-amino-3-(4-amino-4-methylpiperidin-1-yl)-1,2,4-triazin-6-yl)thio)-2-chlorophenyl)-2-hydroxy-4-oxo-4H-pyrido[1,2-a]pyrimidine-3-carboxamide | as HCl salt: $^1$H NMR (400 MHz, Methanol-d$_4$) δ ppm 9.16 (d, J = 7.1 Hz, 1 H), 8.71-8.59 (m, 1 H), 8.19 (t, J = 7.8 Hz, 1 H), 7.59 (d, J = 8.7 Hz, 1 H), 7.52-7.39 (m, 3 H), 4.15 (br, s, 2 H), 3.60-3.45 (m, 2 H), 2.05-1.84 (m, 4 H), 1.52 (s, 3H). MS m/z (M + H)$^+$ 554.3. HRMS calcd for C$_{24}$H$_{25}$ClN$_9$O$_3$S (M + H)$^+$ 554.1490, found 554.1474. | 0.011 |
| 42 | 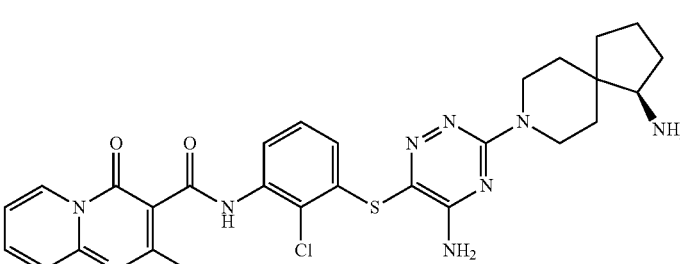<br>(R)-N-(3-((5-amino-3-(1-amino-8-azaspiro[4.5]decan-8-yl)-1,2,4-triazin-6-yl)thio)-2-chlorophenyl)-2-hydroxy-4-oxo-4H-pyrido[1,2-a]pyrimidine-3-carboxamide | as TFA salt: $^1$H NMR (400 MHz, Methanol-d$_4$) δ ppm 12.22 (s, 1 H), 9.13 (d, J = 7.0 Hz, 1 H), 8.59 (dt, J = 8.2, 2.1 Hz, 1 H), 8.16 (ddd, J = 8.8, 6.8, 1.7 Hz, 1 H), 7.56 (d, J = 8.8 Hz, 1 H), 7.49-7.29 (m, 3 H), 4.26 (d, J = 40.7 Hz, 2 H), 3.29-3.19 (m, 3 H), 2.32-2.11 (m, 1 H), 1.96-1.47 (m, 9 H). HRMS calcd for C$_{27}$H$_{29}$ClN$_9$O$_3$S (M + H)$^+$ 594.1803, found 594.1808. | 0.016 |
| 43 | 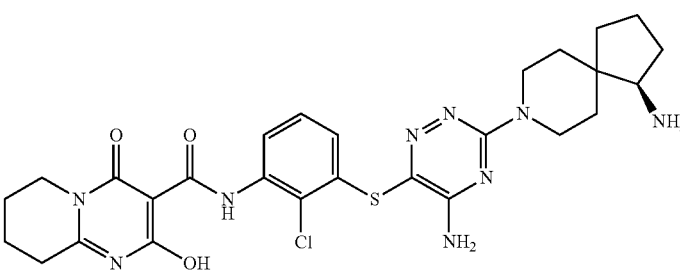<br>(R)-N-(3-((5-amino-3-(1-amino-8-azaspiro[4.5]decan-8-yl)-1,2,4-triazin-6-yl)thio)-2-chlorophenyl)-2-hydroxy-4-oxo-6,7,8,9-tetrahydro-4H-pyrido[1,2-a]pyrimidine-3-carboxamide | as TFA salt: $^1$H NMR (400 MHz, DMSO-d$_6$) δ ppm 14.75 (s, 1 H), 12.28 (s, 1 H), 8.33 (d, J = 8.4 Hz, 1 H), 7.88 (d, J = 5.7 Hz, 3H), 7.38 (t, J = 8.1 Hz, 1 H), 7.10-6.80 (s, 1 H), 4.27 (d, J = 19.1 Hz, 2 H), 3.85 (s, 2 H), 3.24-3.09 (m, 4 H), 2.89 (t, J = 6.5 Hz, 2 H), 2.06 (dt, J = 9.5, 4.6 Hz, 1 H), 1.91 (p, J = 5.9 Hz, 2 H), 1.85-1.60 (m, 7 H), 1.57-1.35 (m, 3 H). HRMS calcd for C$_{27}$H$_{33}$ClN$_9$O$_3$S (M + H)$^+$ 598.2085, found 598.2116. | 0.0015 |

The following compounds identified in Table 4 were made using the procedure or modifications to the procedure as exemplified for Example 1 with the appropriate pyrimidine-3-carboxylic ester and tert-butyl (1-(5-((3-amino-2-chlorophenyl)thio)pyrazin-2-yl)-4-methylpiperidin-4-yl)carbamate.

TABLE 4

| Example | Compound | Characterization | IC$_{50}$ (μM) |
| --- | --- | --- | --- |
| 44 | 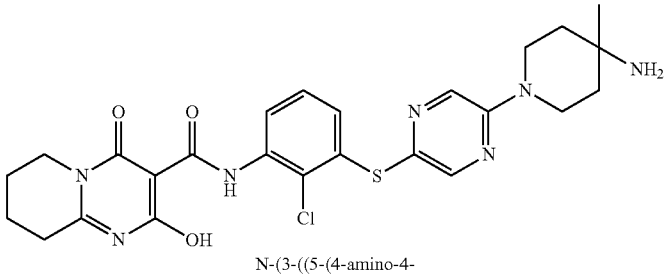<br>N-(3-((5-(4-amino-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, DMSO-d$_6$) δ ppm 12.25 (s, 1 H), 8.48 (s, 1 H), 8.30 (d, J = 1.1 Hz, 1 H), 8.22 (d, J = 8.1 Hz, 1 H), 8.05 (br. s, 2 H), 7.28 (t, J = 8.1 Hz, 1 H), 6.72 (d, J = 7.8 Hz, 1 H), 4.18-4.05 (m, 2 H), 3.90-3.82 (m, 2 H), 3.42-3.37 (m, 3 H), 2.55-2.53 (m, 2 H), 1.96-1.87 (m, 2 H), 1.85-1.67 (m, 6 H), 1.39 (s, 3 H). HRMS calcd for C$_{25}$H$_{29}$ClN$_7$O$_3$S (M + H)$^+$ 542.1741, found 542.1757. | 0.014 |
| 45 | 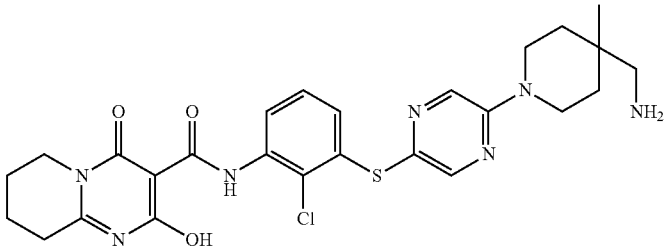 [SMILES: CC1(CN)CCN(c2cnc(Sc3cccc(NC(=O)c4c(O)nc5n(c4=O)CCCC5)c3Cl)cn2)CC1]<br>N-(3-((5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide | as HCl salt: $^1$H NMR (400 MHz, DMSO-d$_6$) δ ppm 12.23 (s, 1 H), 8.44 (d, J = 1.1 Hz, 1 H), 8.27 (d, J = 1.2 Hz, 1 H), 8.19 (dd, J = 8.2, 1.2 Hz, 1 H), 8.09 (br. s, 3 H), 7.27 (t, J = 8.1 Hz, 1 H), 6.70 (dd, J = 8.0, 1.3 Hz, 1 H), 3.96-3.82 (m, 4 H), 3.50-3.39 (m, 2H), 2.88 (t, J = 6.4 Hz, 2 H), 2.82-2.73 (m, 2 H), 1.95-1.86 (m, 2 H), 1.85-1.76 (m, 2 H), 1.61-1.51 (m, 2 H), 1.51-1.41 (m, 2 H), 1.09 (s, 3 H). HRMS calcd for C$_{26}$H$_{31}$ClN$_7$O$_3$S (M + H)$^+$ 556.1898, found 556.1898. | 0.007 |

Example 46

N-(3-((2-(4-Amino-4-methylpiperidin-1-yl)-3H-imidazo[4,5-b]pyridin-5-yl)thio)phenyl)-4-hydroxy-2-oxo-1-phenyl-2,5-dihydro-1H-pyrrole-3-carboxamide

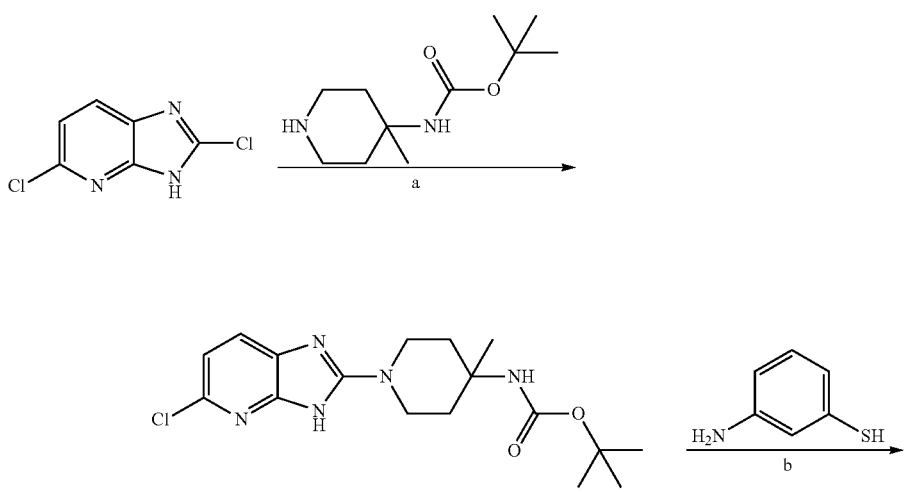

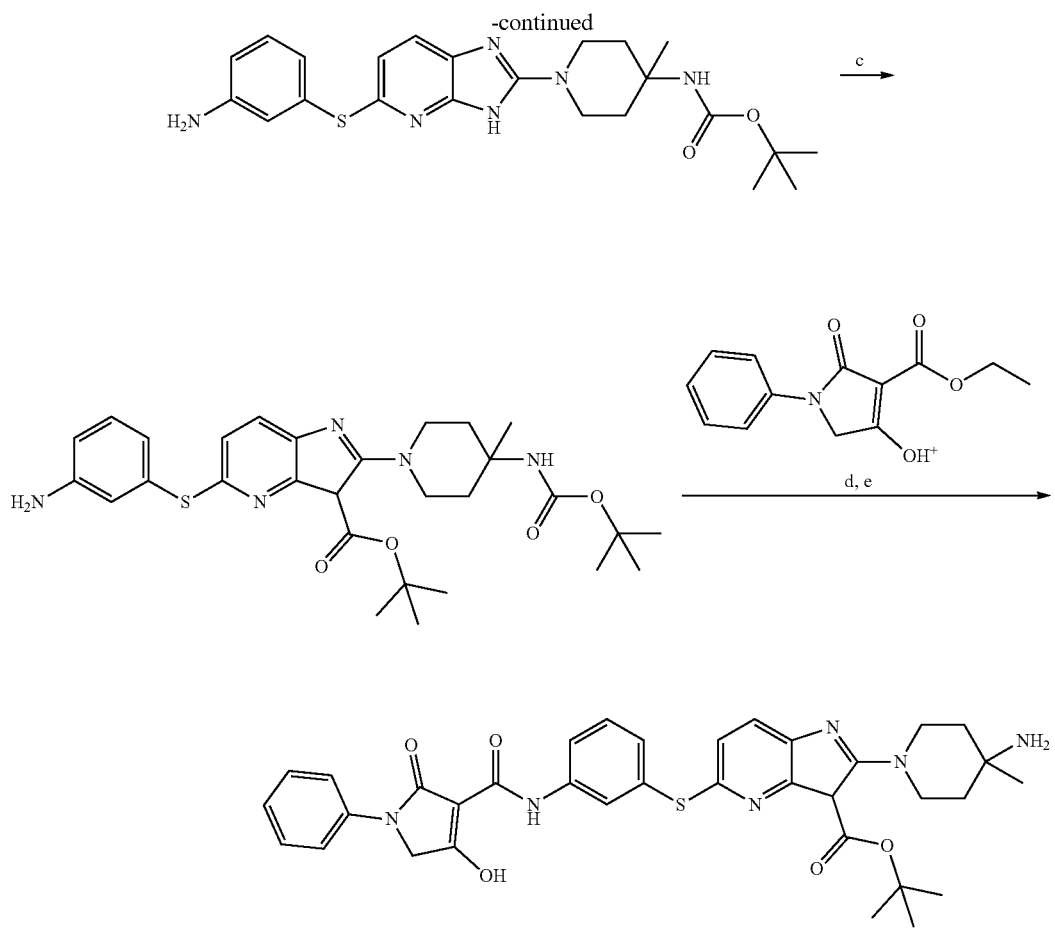

Step a: A mixture of 2,5-dichloro-3H-imidazo[4,5-b]pyridine (2.0 g, 10.64 mmol), tert-butyl (4-methylpiperidin-4-yl)carbamate (3.19 g, 14.89 mmol) and N-methylmorpholine (1.29 mL, 11.70 mmol) in NMP (13 mL) was radiated in a microwave reactor at 110° C. for 1 h. After cooling to RT, the reaction mixture was poured into ice water (800 mL), and filtered. The solid residue was washed with water and dried under reduced pressure at 45° C. to give tert-butyl (1-(5-chloro-3H-imidazo[4,5-b]pyridin-2-yl)-4-methylpiperidin-4-yl)carbamate (3.11 g). MS m/z 366.3 (M+H)+.

Step b: A suspension of tert-butyl (1-(5-chloro-3H-imidazo[4,5-b]pyridin-2-yl)-4-methylpiperidin-4-yl)carbamate (0.350 g, 0.957 mmol), 3-aminobenzenethiol (0.599 g, 4.78 mmol) and N-methylmorpholine (1.578 mL, 14.35 mmol) in NMP (3 mL) was radiated in a microwave reactor at 230° C. for 45 min. After cooling, the reaction mixture was poured into DCM, and filtered. The crude solid was purified by HPLC (15-40% MeCN in water, 5 mM NH4OH modifier) to give 61 mg tert-butyl (1-(5-((3-aminophenyl)thio)-3H-imidazo[4,5-b]pyridin-2-yl)-4-methylpiperidin-4-yl)carbamate. MS m/z 355.2 (M+H)+.

Step c: To a solution of tert-butyl (1-(5-((3-aminophenyl)thio)-3H-imidazo[4,5-b]pyridin-2-yl)-4-methylpiperidin-4-yl)carbamate (60 mg, 0.169 mmol), Boc2O (85 mg, 0.389 mmol) in THF (4 mL) was added TEA (0.083 mL, 0.592 mmol) and heated to 70° C. for 4 h. The reaction mixture was concentrated under reduced pressure to afford 94 mg tert-butyl 5-((3-aminophenyl)thio)-2-(4-((tert-butoxycarbonyl)amino)-4-methylpiperidin-1-yl)-3H-imidazo[4,5-b]pyridine-3-carboxylate. MS m/z 554.8 (M+H)+.

Step d: A suspension of tert-butyl 5-((3-aminophenyl)thio)-2-(4-((tert-butoxycarbonyl)amino)-4-methylpiperidin-1-yl)-3H-imidazo[4,5-b]pyridine-3-carboxylate (90 mg, 0.162 mmol) and ethyl 4-hydroxy-2-oxo-1-phenyl-2,5-dihydro-1H-pyrrole-3-carboxylate (48.1 mg, 0.195 mmol) in THF (2 mL) was radiated in a microwave reactor at 125° C. for 20 min. After cooling the reaction mixture to RT, the precipitate was filtered and rinsed with MeOH to give tert-butyl 2-(4-((tert-butoxycarbonyl)amino)-4-methylpiperidin-1-yl)-5-((3-(4-hydroxy-2-oxo-1-phenyl-2,5-dihydro-1H-pyrrole-3-carboxamido)phenyl)thio)-3H-imidazo[4,5-b]pyridine-3-carboxylate (0.095 g). MS m/z 555.3 (M+H-2Boc)+.

Step e: To a solution of tert-butyl 2-(4-((tert-butoxycarbonyl)amino)-4-methylpiperidin-1-yl)-5-((3-(4-hydroxy-2-oxo-1-phenyl-2,5-dihydro-1H-pyrrole-3-carboxamido)phenyl)thio)-3H-imidazo[4,5-b]pyridine-3-carboxylate (0.091 g, 0.120 mmol) in dioxane (0.2 mL) was added 4 M HCl in dioxane (0.121 mL). After stirring at ambient temperature for 14 h, the volatiles were removed under reduced pressure. The crude residue was titurated with MeOH several times and the solid was purified by HPLC (15-40% MeCN in water, 5 mM NH4OH modifier) to provide N-(3-((2-(4-amino-4-methylpiperidin-1-yl)-3H-imidazo[4,5-b]pyridin-5-yl)thio)phenyl)-4-hydroxy-2-oxo-1-phenyl-2,5-dihydro-1H-pyrrole-3-carboxamide (3.5 mg).

The following compounds identified in Table 5 was made using the procedure or modifications to the procedure as exemplified for Example 46.

TABLE 5

| Example | Compound | Characterization | IC$_{50}$ (μM) |
|---|---|---|---|
| 46 | 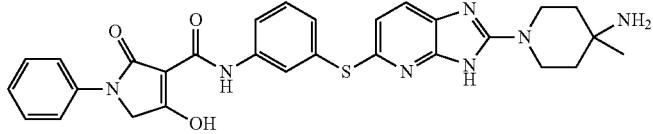 [SMILES: CC1(N)CCN(c2nc3ccc(Sc4cccc(NC(=O)C5=C(O)CN(c6ccccc6)C5=O)c4)nc3[nH]2)CC1]<br>N-(3-((2-(4-amino-4-methylpiperidin-1-yl)-3H-imidazo[4,5-b]pyridin-5-yl)thio)phenyl)-4-hydroxy-2-oxo-1-phenyl-2,5-dihydro-1H-pyrrole-3-carboxamide | $^1$H NMR (400 MHz, DMSO-d$_6$) δ ppm 11.08 (s, 1 H), 7.80 (s, 2 H), 7.68 (d, J = 7.8 Hz, 3 H), 7.44 (s, 2 H), 7.33-7.20 (m, 5 H), 6.97-6.87 (m, 3 H), 3.98-3.88 (m, 2 H), 3.83 (s, 2 H), 3.39-3.31 (m, 2 H), 1.85-1.64 (m, 4H), 1.36 (s, 3 H). HRMS calcd for C$_{29}$H$_{30}$N$_7$O$_3$S (M + H)$^+$ 556.2158, found 556.2133. | 0.07 |
| 47 | 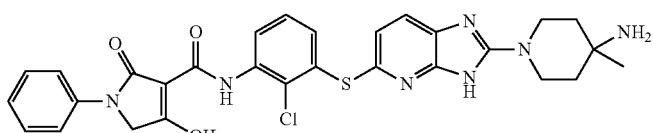<br>N-(3-((2-(4-amino-4-methylpiperidin-1-yl)-3H-imidazo[4,5-b]pyridin-5-yl)thio)-2-chlorophenyl)-4-hydroxy-2-oxo-1-phenyl-2,5-dihydro-1H-pyrrole-3-carboxamide | $^1$H NMR (400 MHz, DMSO-d$_6$) δ ppm 11.37 (s, 1 H), 8.51 (d, J = 7.9 Hz, 1 H), 7.71 (d, J = 7.9 Hz, 2 H), 7.46 (d, J = 7.8 Hz, 1 H), 7.29-7.23 (m, 2 H), 7.01 (dt, J = 76.8, 7.7 Hz, 3 H), 6.73 (d, J = 7.7 Hz, 1 H), 3.95-3.75 (m, 4 H), 3.50-3.42 (m, 2 H), 1.74-1.60 (m, 4 H), 1.30 (s, 3 H). HRMS calcd for C$_{29}$H$_{29}$ClN$_7$O$_3$S (M + H)$^+$ 590.1748, found 590.1742. | 0.003 |
| 48 | 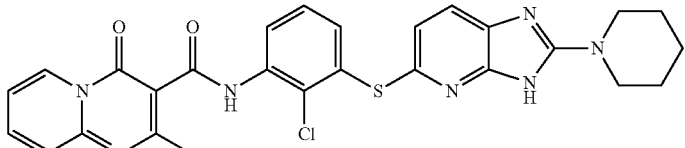<br>N-(2-chloro-3-((2-(piperidin-1-yl)-3H-imidazo[4,5-b]pyridin-5-yl)thio)phenyl)-2-hydroxy-4-oxo-4H-pyrido[1,2-a]pyrimidine-3-carboxamide | as free base: $^1$H NMR (400 MHz, DMSO-d$_6$) δ ppm 12.31 (s, 1 H), 12.14 (bs, 1 H), 11.65 (bs, 1 H), 9.02 (d, J = 6.9 Hz, 1 H), 8.33 (s, 1 H), 8.14 (t, J = 7.6 Hz, 1 H), 7.56-7.34 (m, 3 H), 7.27 (d, J = 6.6 Hz, 1 H), 7.21-6.77 (m, 2 H), 3.55 (m, 4 H), 1.58 (m, 6 H). HRMS calcd for C$_{26}$H$_{23}$ClN$_7$O$_3$S (M + H)$^+$ 548.1272, found 548.1263. | 0.061 |
| 49 | 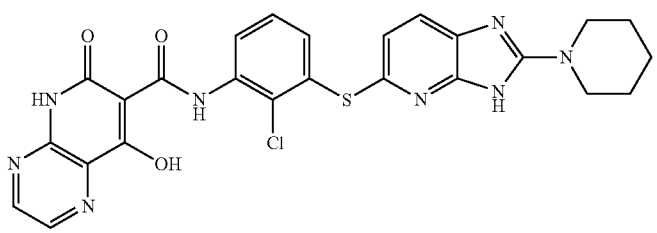 [SMILES: O=C(Nc1cccc(Sc2ccc3nc(N4CCCCC4)[nH]c3n2)c1Cl)c1c(O)c2nccnc2[nH]c1=O]<br>N-(2-chloro-3-((2-(piperidin-1-yl)-3H-imidazo[4,5-b]pyridin-5-yl)thio)phenyl)-8-hydroxy-6-oxo-5,6-dihydropyrido[2,3-b]pyrazine-7-carboxamide | as free base: $^1$H NMR (400 MHz, DMSO-d$_6$) δ ppm 16.07 (s, 1H), 12.98 (s, 2H), 12.16 (s, 1H), 8.80 (s, 1H), 8.70 (s, 1H), 8.25 (s, 1H), 7.46 (s, 1H), 7.31 (s, 1H), 7.06 (m, 2H), 3.56 (m, 4H), 1.58 (m, 6H). HRMS calcd for C$_{25}$H$_{22}$ClN$_8$O$_3$S (M + H)$^+$ 549.1224, found 549.1210. | 0.036 |

Example 50

N-(4-((3-Amino-5-(4-amino-4-methylpiperidin-1-yl)pyrazin-2-yl)thio)-3-chlorophenyl)-4-hydroxy-2-oxo-1-phenyl-2,5-dihydro-1H-pyrrole-3-carboxamide

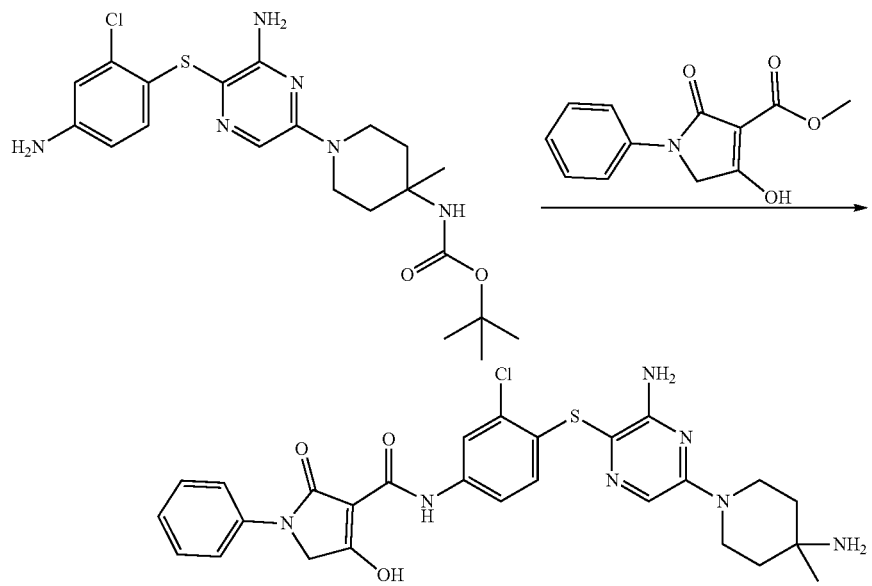

A suspension of tert-butyl(1-(6-amino-5-((4-amino-2-chlorophenyl)thio)pyrazin-2-yl)-4-methylpiperidin-4-yl)carbamate (50 mg, 0.108 mmol) and methyl 4-hydroxy-2-oxo-1-phenyl-2,5-dihydro-1H-pyrrole-3-carboxylate (30 mg, 0.140 mmol) in THF (1 mL) was radiated to 115° C. in a microwave reactor for 1.5 h. After cooling the reaction mixture, the volatiles were removed under reduce pressure and the crude mixture was dissolved in DCM (2 mL). A solution of 4 M HCl (in dioxane, 2 mL) was added and the resulting mixture was heated to 40° C. for 1 h. After cooling to RT, the solution was concentrated under reduced pressure and the resulting residue was purified by HPLC (15-40% MeCN/water, 0.1% NH$_4$OH modifier), to give the title compound (12 mg). MS m/z 566.0 (M+H)$^+$.

The following compounds identified in Table 6 was made using the procedure or modifications to the procedure as exemplified for Example 46.

TABLE 6

| Example | Compound | Characterization | IC$_{50}$ (μM) |
|---|---|---|---|
| 50 | N-(4-((3-amino-5-(4-amino-4-methylpiperidin-1-yl)pyrazin-2-yl)thio)-3-chlorophenyl)-4-hydroxy-2-oxo-1-phenyl-2,5-dihydro-1H-pyrrole-3-carboxamide | $^1$H NMR (400 MHz, DMSO-d$_6$) δ ppm 11.12 (br. s, 1 H) 8.04 (d, J = 2.3 Hz, 1 H) 7.97 (s, 1 H) 7.94 (br.s, 1 H) 7.69 (d, J = 8.0 Hz, 2 H) 7.61 (s, 1 H) 7.12-7.34 (m, 3 H) 6.91 (t, J = 7.3 Hz, 1 H) 6.77 (d, J = 8.5 Hz, 1 H) 6.13 (br. s, 1 H) 3.94-4.11 (m, 2H) 3.87 (s, 2 H) 3.16-3.30 (m, 2 H) 2.54-2.68 (m, 1 H) 1.62-1.82 (m, 4 H) 1.38 (s, 3 H). HRMS calcd for C$_{27}$H$_{29}$ClN$_7$O$_3$S (M + H)$^+$ 566.1741, found 566.1719. | 0.070 |

TABLE 6-continued

| Example | Compound | Characterization | IC$_{50}$ (μM) |
|---|---|---|---|
| 51 | 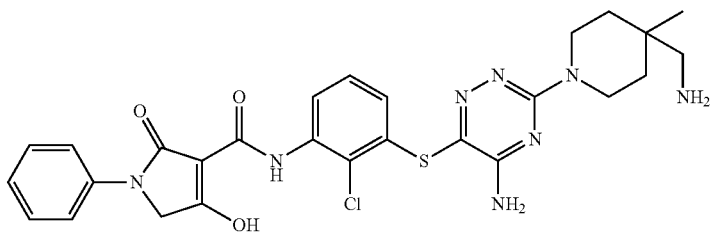 [SMILES: CC1(CN)CCN(c2nnc(Sc3cccc(NC(=O)C4=C(O)CN(c5ccccc5)C4=O)c3Cl)c(N)n2)CC1]<br>N-(3-((5-amino-3-(4-(aminomethyl)-4-methylpiperidin-1-yl)-1,2,4-triazin-6-yl)thio)-2-chlorophenyl)-4-hydroxy-2-oxo-1-phenyl-2,5-dihydro-1H-pyrrole-3-carboxamide | $^1$H NMR (600 MHz, DMSO-d6) δ ppm 11.40 (s, 1 H), 8.45 (d, J = 8.2 Hz, 1H), 7.71 (d, J = 8.1 Hz, 2 H), 7.27 (t, J = 7.8 Hz, 2 H). 7.10 (t, J = 8.1 Hz, 1 H), 6.92 (t, J = 7.3 Hz, 1 H), 6.54 (s, 1 H), 6.29 (d, J = 7.8 Hz, 1 H), 4.17-4.05 (m, 2 H), 3.87 (s, 2 H), 3.53-3.44 (m, 2 H), 2.7.3 (s, 2 H), 1.55-1.44 (m, 2 H), 1.43-1.32 (m, 2 H), 1.05 (s, 3 H). HRMS calcd for C$_{27}$H$_{30}$ClN$_8$O$_3$S (M + H)$^+$ 581.1772, found 581.1852. | 0.012 |
| 52 | 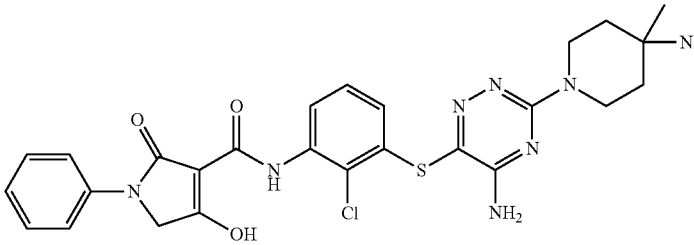<br>N-(3-((5-amino-3-(4-amino-4-methylpiperidin-1-yl)-1,2,4-triazin-6-yl)thio)-2-chlorophenyl)-4-hydroxy-2-oxo-1-phenyl-2,5-dihydro-1H-pyrrole-3-carboxamide | $^1$H NMR (400 MHz, DMSO-d6) δ ppm 11.4.3 (s, 1 H), 8.42 (d, J = 8.1 Hz, 1 H), 7.86 (s, 2 H), 7.72 (d, J = 7.9 Hz, 2 H), 7.32-7.23 (m, 2 H), 6.99 (t, J = 8.1 Hz, 1 H), 6.92 (t, J = 7.3 Hz, 1 H), 6.31 (dd. J = 7.9, 1.1 Hz, 1 H), 4.38-4.19 (m, 2 H), 3.88 (s, 2 H), 3.51-3.40 (m, 2 H), 1.85-1.68 (m, 4 H), 1.38 (s, 3 H). HRMS calcd for C$_{26}$H$_{28}$ClN$_8$O$_3$S (M + H)$^+$ 567.1720, found 567.1688. | 0.003 |
| 53 | 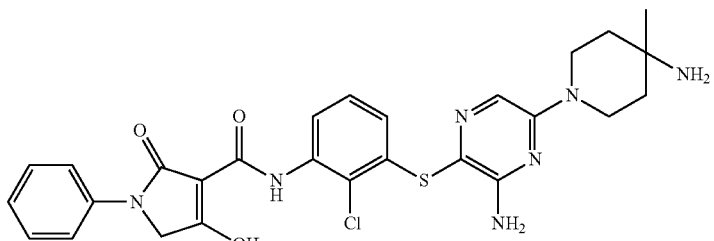<br>N-(3-((3-amino-5-(4-amino-4-methylpiperidin-1-yl)pyrazin-2-yl)thio)-2-chlorophenyl)-4-hydroxy-2-oxo-1-phenyl-2,5-dihydro-1H-pyrrole-3-carboxamide | $^1$H NMR (400 MHz, DMSO-d$_6$) δ ppm 11.39 (s, 1 H), 8.38 (dd, J = 8.28, 1.25 Hz, 1 H), 7.83 (br. s., 2 H), 7.71 (d, J = 7.78 Hz, 2 H), 7.66 (s, 1 H), 7.26 (dd, J = 8.53, 7.28 Hz, 2 H), 6.99 (t, J = 8.03 Hz, 1 H), 6.91 (t, J = 7.28 Hz, 1 H), 6.12-6.22 (m, 3 H), 4.04 (d, J = 13.80 Hz, 2 H), 3.84 (s, 2 H), 3.21-3.33 (m, 2 H), 1.62-1.84 (m, 4 H), 1.37 (s, 3 H). HRMS calcd for C$_{27}$H$_{29}$ClN$_7$O$_3$S (M + H)$^+$ 566.1741, found 566.1754. | 0.0044 |
| 54 | 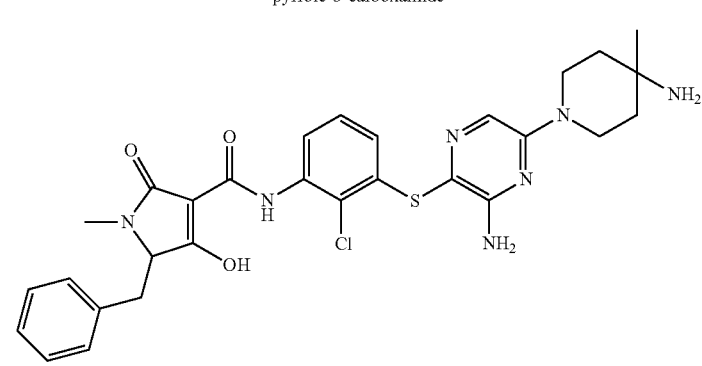<br>N-(3-((3-amino-5-(4-amino-4-methylpiperidin-1-yl)pyrazin-2-yl)thio)-2-chlorophenyl)-5-benzyl-4-hydroxy-1-methyl-2-oxo-2,5-dihydro-1H-pyrrole-3-carboxamide | $^1$H NMR (400 MHz, DMSO-d$_6$) δ ppm 11.42 (br. s, 1 H), 8.28 (d, J = 8.0.3 Hz, 1 H), 8.05 (br. s., 3 H), 7.64 (s, 1 H), 7.05-7.31 (m, 5 H), 6.70 (t, J = 8.0.3 Hz, 1 H), 6.02-6.20 (m, 3 H), 3.97-4.14 (m, 2 H), 3.64 (br. s, 1 H), 3.27-3.40 (overlapped with H$_2$O peak, m, 1 H), 3.09 (dd, J = 14.05, 4.27 Hz, 1 H), 2.91 (dd, J = 13.93, 5.14 Hz, 1 H), 2.63 (s, 3 H), 1.80-2.00 (m, 2 H), 1.68 (d, J = 13.30 Hz, 2H), 1.30-1.45 (m, 3 H). HRMS calcd for C$_{29}$H$_{33}$ClN$_7$O$_3$S (M + H)$^+$ 594.2054, found 594.2023. | 0.0073 |

TABLE 6-continued

| Example | Compound | Characterization | IC$_{50}$ (μM) |
|---|---|---|---|
| 55 | 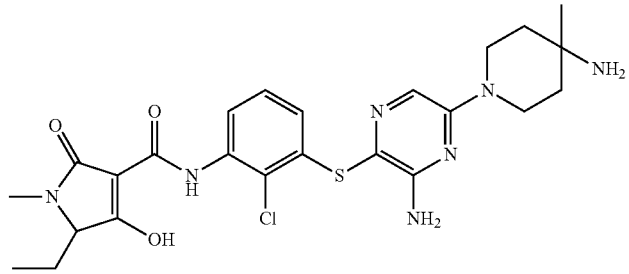 [SMILES: CCC1C(O)=C(C(=O)Nc2cccc(Sc3ncc(N4CCC(C)(N)CC4)nc3N)c2Cl)C(=O)N1C]<br>N-(3-((3-amino-5-(4-amino-4-methylpiperidin-1-yl)pyrazin-2-yl)thio)-2-chlorophenyl)-5-ethyl-4-hydroxy-1-methyl-2-oxo-2,5-dihydro-1H-pyrrole-3-carboxamide | $^1$H NMR (400 MHz, DMSO-d$_6$) δ ppm 11.49 (br. s., 1 H), 8.30 (d, J = 8.0 Hz, 1 H), 8.10 (br. s, 3 H), 7.65 (s, 1 H), 6.68 (t, J = 8.0 Hz, 1 H), 6.14 (d, J = 7.0 Hz, 3H), 3.91-4.14 (m, 2 H), 3.24-3.33 (m, 2 H), 2.75 (s, 3 H), 1.83-2.04 (m, 2 H), 1.55-1.83 (m, 4 H), 1.37 (s, 3 H), 0.66 (t, J = 7.3 Hz, 3 H). HRMS calcd for C$_{24}$H$_{31}$ClN$_7$O$_3$S (M + H)$^+$ 532.1898, found 532.1861. | 0.0028 |
| 56 | 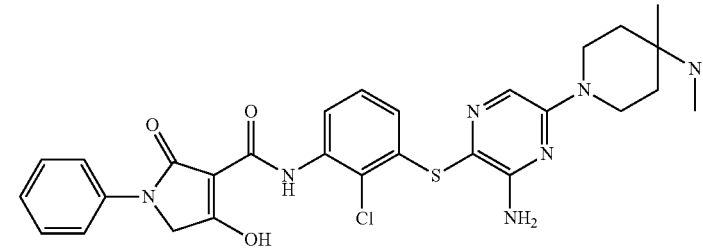<br>N-(3-((3-amino-5-(4-methyl-4-(methylamino)piperidin-1-yl)pyrazin-2-yl)thio)-2-chlorophenyl)-4-hydroxy-2-oxo-1-phenyl-2,5-dihydro-1H-pyrrole-3-carboxamide | $^1$H NMR (400 MHz, DMSO-d$_6$) δ ppm 11.38 (s, 2 H), 8.39 (d, J = 8.3 Hz, 2H), 7.61-7.76 (m, 3 H), 7.26 (t, J = 7.9 Hz, 2 H), 7.05 (t, J = 8.2 Hz, 1 H), 6.90 (t, J = 7.4 Hz, 1 H), 6.12-6.26 (m, 3 H), 3.83 (s, 2 H), 3.32 (s, overlap with water, 3 H), 3.17 (br. s., 2 H), 1.72 (br. s., 4H), 1.35 (br. s., 3 H). HRMS calcd for C$_{28}$H$_{31}$ClN$_7$O$_3$S (M + H)$^+$ 580.1898, found 580.1885. | 0.0066 |
| 57 | 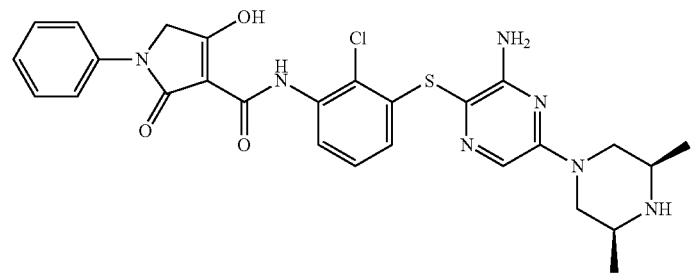 [SMILES: C[C@@H]1CN(c2cnc(Sc3cccc(NC(=O)C4=C(O)CN(c5ccccc5)C4=O)c3Cl)c(N)n2)C[C@H](C)N1]<br>N-(3-((3-amino-5-(cis-3,5-dimethylpiperazin-1-yl)pyrazin-2-yl)thio)-2-chlorophenyl)-4-hydroxy-2-oxo-1-phenyl-2,5-dihydro-1H-pyrrole-3-carboxamide | as HCl salt: $^1$H NMR (400 MHz, DMSO-d$_6$) δ ppm 10.96 (s, 1 H), 9.59-9.46 (m, 1 H), 9.16-9.0.3 (m, 1 H), 8.26 (dd, J = 8.2, 1.4 Hz, 1 H), 7.73 (s, 2 H), 7.72-7.70 (m, 1 H), 7.43-7.38 (m, 2 H), 7.22-7.17 (m, 1 H), 7.16-7.11 (m, 1 H), 6.39 (dd, J = 8.0, 1.4 Hz, 1 H), 4.62 (s, 2 H), 4.51-4.43 (m, 2 H), 3.38-3.26 (m, 2 H), 2.97-2.87 (m, 2 H), 1.31 (s, 3 H), 1.29 (s, 3H). HRMS calcd for C$_{27}$H$_{29}$ClN$_7$O$_3$S (M + H)$^+$ 566.1741, found 566.1743. | 0.011 |

Example 58

N-(3-((3-Amino-5-(4-amino-4-methylpiperidin-1-yl)pyrazin-2-yl)thio)-2-chlorophenyl)-4-hydroxy-2-oxo-1,2-dihydroquinoline-3-carboxamide

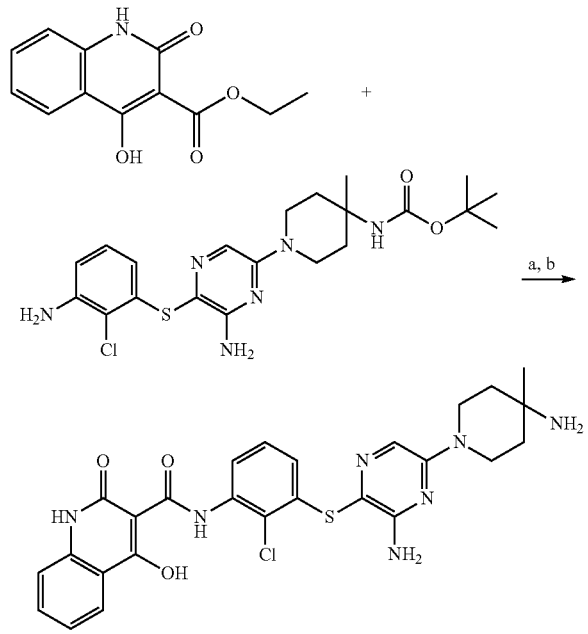

A suspension of tert-butyl (1-(6-amino-5-((3-amino-2-chlorophenyl)thio)pyrazin-2-yl)-4-methylpiperidin-4-yl)carbamate (0.140 g, 0.30 mmol) and ethyl 4-hydroxy-2-oxo-1,2-dihydroquinoline-3-carboxylate (91 mg, 0.39 mmol) in THF (1.5 mL) was radiated to 115° C. in a microwave reactor for 1.5 h. After cooling the reaction mixture to RT, the volatiles were removed under reduce pressure and the crude mixture was dissolved in DCM (2 mL). A solution of HCl (4 M in dioxane, 2 mL) was added and the resulting mixture was heated to 40° C. for 1 h. After cooling to RT the solution was concentrated under reduced pressure and the resulting residue was purified by HPLC (15-40% MeCN/water, 0.1% NH$_4$OH modifier), to give the title compound (12 mg). MS m/z 552.0 (M+H)$^+$. $^1$H NMR (400 MHz, DMSO-d$_6$) δ ppm 8.23-8.37 (m, 1H), 7.91-8.03 (m, 1H), 7.59-7.71 (m, 2H), 7.40-7.52 (m, 1H), 7.16-7.25 (m, 1H), 7.09 (br. s, 2H), 6.77-6.89 (m, 1H), 6.51-6.61 (m, 1H), 6.26-6.35 (m, 1H), 6.17 (br. s, 2H), 5.76-5.87 (m, 1H), 5.38-5.49 (m, 1H), 3.81-4.03 (m, 2H), 3.38-3.49 (m, 2H), 1.57-1.80 (m, 4H), 1.33 (s, 3H). HRMS calcd for C$_{26}$H$_{27}$ClN$_7$O$_3$S (M+H)$^+$552.1585, found 552.1602. IC$_{50}$=0.072 μM.

The following compound identified in Table 7 were made using the procedure or modifications to the procedure as exemplified for Example 50.

TABLE 7

| Example | Compound | Characterization | IC$_{50}$ (μM) |
|---|---|---|---|
| 59 | N-(3-((3-amino-5-(4-amino-4-methylpiperidin-1-yl)pyrazin-2-yl)thio)-2-chlorophenyl)-4-hydroxy-1,5,5-trimethyl-2-oxo-2,5-dihydro-1H-pyrrole-3-carboxamide | $^1$H NMR (400 MHz, DMSO-d$_6$) δ ppm 11.51 (s, 1 H), 8.38-8.09 (m, 4 H), 7.65 (s, 1 H), 6.62 (t, J = 8.0 Hz, 1 H), 6.22-5.99 (m, 3 H), 4.21-3.90 (m, 2 H), 3.35-3.24 (m, 2 H), 2.73 (s, 3 H), 2.11-1.90 (m, 2 H), 1.79-1.59 (m, 2 H), 1.38 (s, 3 H), 1.12 (s, 6 H). HRMS calcd for C$_{24}$H$_{31}$ClN$_7$O$_3$S (M + H)$^+$ 532.1898, found 532.1887. | <0.003 |
| 60 | (S)-5-benzyl-N-(2-chloro-3-((2-(piperidin-1-yl)-3H-imidazo[4,5-b]pyridin-5-yl)thio)phenyl)-4-hydroxy-2-oxo-2,5-dihydro-1H-pyrrole-3-carboxamide | $^1$H NMR (400 MHz, DMSO-d$_6$) δ ppm 11.13 (s, 1 H), 8.39 (d, J = 7.9 Hz, 1H), 7.46 (d, J = 7.9 Hz, 1 H), 7.20 (ddt, J = 24.0, 15.4, 7.7 Hz, 6 H), 7.02 (d, J = 7.9 Hz, 1 H), 6.76 (dd, J = 7.9, 1.2 Hz, 1 H), 4.03 (s, 1 H), 3.56 (m, 4 H), 3.03 (dd, J = 13.8, 4.2 Hz, 1 H), 2.79 (dd, J = 13.8, 6.4 Hz, 1 H), 1.60 (m, 6 H). HRMS calcd for C$_{29}$H$_{28}$ClN$_6$O$_3$S (M + H)$^+$ 575.1632, found 575.1652. | 0.011 |

TABLE 7-continued

| Example | Compound | Characterization | IC$_{50}$ (μM) |
|---|---|---|---|
| 61 | 5-benzyl-N-(2-chloro-3-((2-(piperidin-1-yl)-3H-imidazo[4,5-b]pyridin-5-yl)thio)phenyl)-4-hydroxy-1-methyl-2-oxo-2,5-dihydro-1H-pyrrole-3-carboxamide | $^1$H NMR (400 MHz, DMSO-d$_6$) δ ppm 11.05 (s, 1 H), 8.43-8.34 (m, 1 H), 7.51 (d, J = 8.0 Hz, 1 H), 7.23 (q, J = 7.7, 7.3 Hz, 3 H), 7.17 (tt, J = 6.8, 2.8 Hz, 3 H), 7.06 (d, J = 8.0 Hz, 1 H), 6.85 (dd, J = 7.8, 1.4 Hz, 1 H), 4.19 (s, 1 H), 3.57 (m, 4 H), 3.20 (dd, J = 14.3, 4.7 Hz, 1H), 3.03 (dd, J = 14.3, 4.5 Hz, 1H), 2.79 (s, 3H), 1.61 (m, 6 H). HRMS calcd for C$_{30}$H$_{30}$ClN$_6$O$_3$S (M + H)$^+$ 589.1789, found 589.1776. | 0.022 |
| 62 | N-(2-chloro-3-((2-(piperidin-1-yl)-3H-imidazo[4,5-b]pyridin-5-yl)thio)phenyl)-5-ethyl-4-hydroxy-1-methyl-2-oxo-2,5-dihydro-1H-pyrrole-3-carboxamide | $^1$H NMR (400 MHz, DMSO-d$_6$) δ ppm 11.15 (s, 1 H), 8.41 (d, J = 8.2 Hz, 1 H), 7.51 (d, J = 7.9 Hz, 1 H), 7.23 (t, J = 8.1 Hz, 1 H), 7.08 (d, J = 8.0 Hz, 1 H), 6.86 (d, J = 7.7 Hz, 1 H), 4.01 (s, 1 H), 3.57 (m, 4 H), 2.82 (s, 3 H), 1.90-1.79 (m, 2 H), 1.61 (m, 6 H), 0.64 (t, J = 7.3 Hz, 3 H). HRMS calcd for C$_{25}$H$_{28}$ClN$_6$O$_3$S (M + H)$^+$ 527.1632, found 527.1624. | 0.025 |
| 63 | N-(2-chloro-3-((2-(piperidin-1-yl)-3H-imidazo[4,5-b]pyridin-5-yl)thio)phenyl)-5-ethyl-4-hydroxy-2-oxo-1-phenyl-2,5-dihydro-1H-pyrrole-3-carboxamide | $^1$H NMR (400 MHz, DMSO-d$_6$) δ ppm 11.32 (s, 1 H), 8.57 (d, J = 8.0 Hz, 1 H), 7.61 (d, J = 8.1 Hz, 1 H), 7.52 (d, J = 7.9 Hz, 2 H), 7.34 (t, J = 7.8 Hz, 2 H), 7.26 (t, J = 7.9 Hz, 1 H), 7.12 (d, J = 8.1 Hz, 1 H), 7.06 (t, J = 7.3 Hz, 1 H), 7.00 (d, J = 7.7 Hz, 1 H), 4.59 (s, 1 H), 3.59 (m, 4 H), 1.80 (d, J = 6.8 Hz, 1 H), 1.69 (dd, J = 13.3, 6.9 Hz, 1 H), 1.62 (m, 6 H), 0.56 (t, J = 7.2 Hz, 3 H). HRMS calcd for C$_{30}$H$_{30}$ClN$_6$O$_3$S (M + H)$^+$ 589.1789, found 589.1780. | 0.052 |
| 64 | (S)-N-(2-chloro-3-((2-(piperidin-1-yl)-3H-imidazo[4,5-b]pyridin-5-yl)thio)phenyl)-4-hydroxy-2-oxo-5-phenyl-2,5-dihydro-1H-pyrrole-3-carboxamide | $^1$H NMR (400 MHz, DMSO-d$_6$) δ ppm 11.27 (s, 1 H), 8.48 (d, J = 8.0 Hz, 1 H), 7.48 (d, J = 8.0 Hz, 1 H), 7.35-7.30 (m, 2 H), 7.29-7.24 (m, 3 H), 7.16 (t, J = 8.1 Hz, 1 H), 7.03 (d, J = 8.0 Hz, 1 H), 6.79 (d, J = 7.8 Hz, 1 H), 4.65 (s, 1 H), 3.56 (m, 4 H), 1.60 (m, 6 H). HRMS calcd for C$_{28}$H$_{26}$ClN$_6$O$_3$S (M + H)$^+$ 561.1476, found 561.1458. | 0.090 |

| Example | Compound | Characterization | IC$_{50}$ (μM) |
|---|---|---|---|
| 65 | 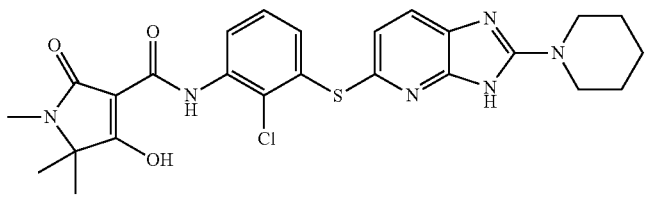 [SMILES: CN1C(=O)C(C(=O)Nc2cccc(Sc3ccc4nc(N5CCCCC5)[nH]c4n3)c2Cl)=C(O)C1(C)C]<br>N-(2-chloro-3-((2-(piperidin-1-yl)-3H-imidazo[4,5-b]pyridin-5-yl)thio)phenyl)-4-hydroxy-1,5,5-trimethyl-2-oxo-2,5-dihydro-1H-pyrrole-3-carboxamide | $^1$H NMR (400 MHz, Methanol-d$_4$) δ ppm 8.48 (d, J = 8.2 Hz, 1 H), 7.43 (d, J = 7.9 Hz, 1 H), 7.07 (t, J = 8.0 Hz, 1 H), 7.00 (d, J = 7.9 Hz, 1 H), 6.81 (d, J = 7.7 Hz, 1 H), 3.59 (m, 4 H), 2.86 (s, 3 H), 1.70 (m, 6 H), 1.26 (s, 6 H). HRMS calcd for C$_{25}$H$_{28}$ClN$_6$O$_3$S (M + H)$^+$ 527.1632, found 527.1631. | 0.042 |

Example 66

N-(3-((3-Amino-5-(4-amino-4-methylpiperidin-1-yl)pyrazin-2-yl)thio)phenyl)-4-hydroxy-2-oxo-1-phenyl-2,5-dihydro-1H-pyrrole-3-carboxamide

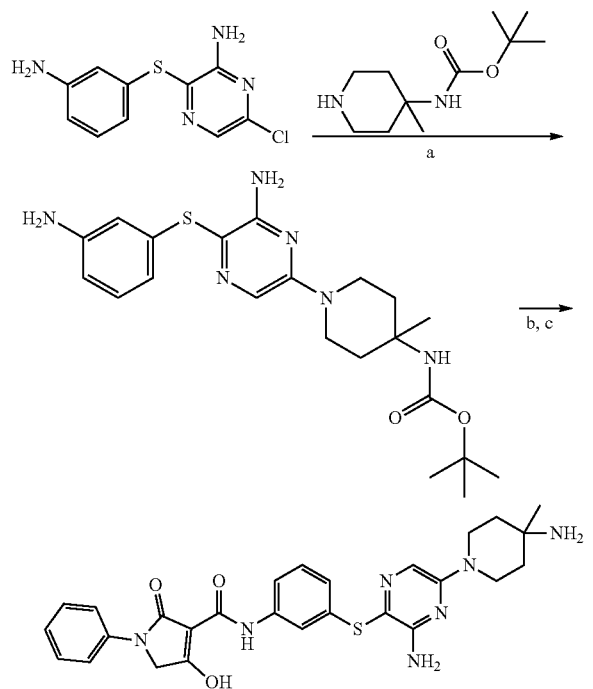

As described for Intermediate 1, a similar procedure was performed using 3-((3-aminophenyl)thio)-6-chloropyrazin-2-amine (0.150 g, 0.594 mmol) and tert-butyl (4-methylpiperidin-4-yl)carbamate (0.191 g, 0.890 mmol) to give tert-butyl (1-(6-amino-5-((3-aminophenyl)thio)pyrazin-2-yl)-4-methylpiperidin-4-yl)carbamate (0.162 g, 0.376 mmol). MS m/z 431.4 (M+H)$^+$. N-(3-((3-amino-5-(4-amino-4-methylpiperidin-1-yl)pyrazin-2-yl)thio)phenyl)-4-hydroxy-2-oxo-1-phenyl-2,5-dihydro-1H-pyrrole-3-carboxamide was prepared using the procedure or modifications to the procedure as exemplified for Example 50. $^1$H NMR (400 MHz, DMSO-d$_6$) δ ppm 11.05 (s, 1H), 7.69 (d, J=7.8 Hz, 2H), 7.63 (s, 1H), 7.55 (s, 2H), 7.33 (s, 1H), 7.26 (dd, J=8.6, 7.4 Hz, 2H), 7.15 (d, J=8.3 Hz, 1H), 7.10 (t, J=7.8 Hz, 1H), 6.91 (t, J=7.3 Hz, 1H), 6.70 (d, J=7.6 Hz, 1H), 6.08 (s, 2H), 4.05 (d, J=13.9 Hz, 2H), 3.85 (s, 2H), 3.26 (d, J=10.4 Hz, 2H), 1.79-1.62 (m, 4H), 1.37 (s, 3H). HRMS calcd for C$_{27}$H$_{30}$N$_7$O$_3$S (M+H)$^+$532.2131, found 532.2122. IC$_{50}$=0.017 μM.

Example 67

N-(3-((3-Amino-5-(4-amino-4-methylpiperidin-1-yl)pyrazin-2-yl)thio)-2-(trifluoromethyl)phenyl)-4-hydroxy-2-oxo-1-phenyl-2,5-dihydro-1H-pyrrole-3-carboxamide

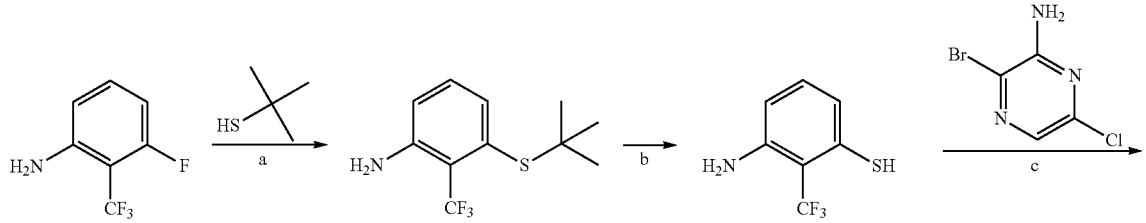

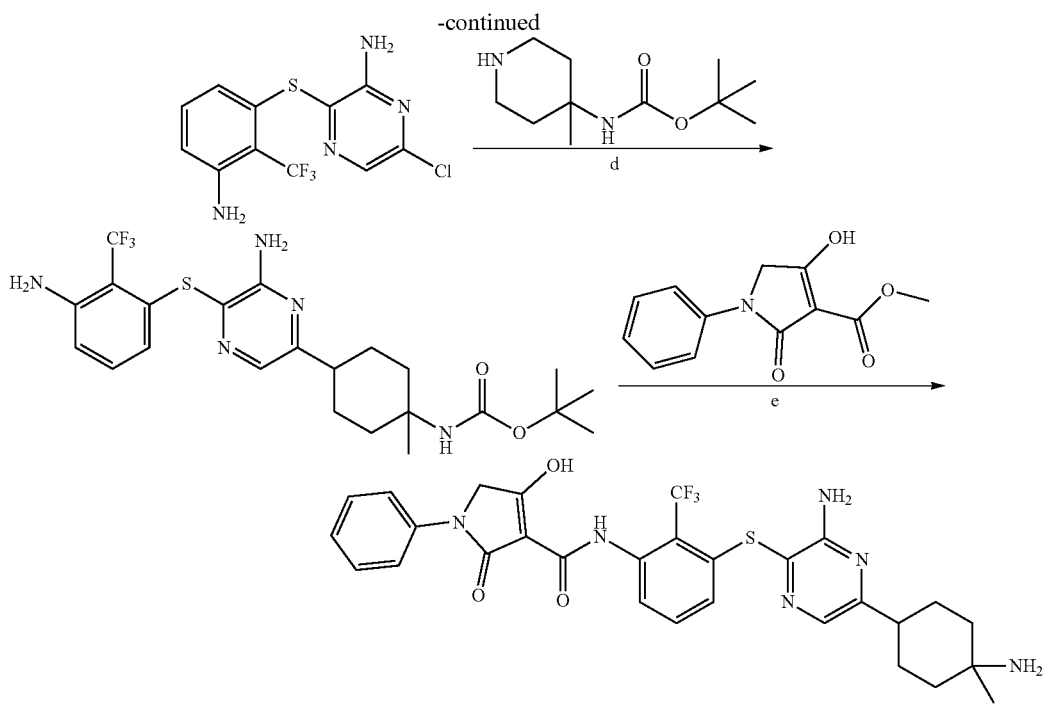

Step a: A suspension of 3-fluoro-2-(trifluoromethyl)aniline (9.7 g, 54.1 mmol), 2-methylpropane-2-thiol (18.31 mL, 162 mmol) and Cs$_2$CO$_3$ (52.9 g, 162 mmol) in DMF (100 mL) was heated to 130° C. for 14 h. After cooling, the reaction mixture was diluted with water (500 mL) and extracted with EtOAc (500 mL). Organic layer was then washed with water (3×400 mL), brine (3×300 mL), dried over Na$_2$SO$_4$, filtered and concentrated under reduced pressure to give 12.52 g 3-(tert-butylthio)-2-(trifluoromethyl) aniline. MS m/z 250.2 (M+H)$^+$.

Step b: A suspension of 3-(tert-butylthio)-2-(trifluoromethyl)aniline (2.2 g, 8.82 mmol) in conc. HCl (80 mL) was heated to 85° C. for 3 h. After cooling, the reaction mixture was concentrated under reduced pressure to near dryness and the solid was filtered. The solid was washed with EtOAc and heptane, and further dried under reduced pressure at 40° C. to give 3-amino-2-(trifluoromethyl)benzenethiol as the HCl salt 1.02 g (4.44 mmol). MS m/z 194.1 (M+H)$^+$.

Step c: As described for Intermediate 1, a similar procedure was performed using 3-amino-2-(trifluoromethyl)benzenethiol (0.45 g, 1.94 mmol) and 3-bromo-6-chloropyrazin-2-amine (0.27 g, 1.30 mmol) to give 3-((3-amino-2-(trifluoromethyl)phenyl)thio)-6-chloropyrazin-2-amine (0.211 g, 0.66 mmol). MS m/z 321.1 (M+H)$^+$.

Step d: As described for Intermediate 1, a similar procedure was performed using 3-((3-amino-2-(trifluoromethyl)phenyl)thio)-6-chloropyrazin-2-amine (100 mg, 0.31 mmol), tert-butyl (4-methylpiperidin-4-yl)carbamate (66.7 mg, 0.31 mmol) to give tert-butyl (1-(6-amino-5-((3-amino-2-(trifluoromethyl)phenyl)thio)pyrazin-2-yl)-4-methylpiperidin-4-yl)carbamate (100 mg, 0.201 mmol). MS m/z 499.3 (M+H)$^+$.

Step e: N-(3-((3-amino-5-(4-amino-4-methylpiperidin-1-yl)pyrazin-2-yl)thio)-2-(trifluoromethyl)phenyl)-4-hydroxy-2-oxo-1-phenyl-2,5-dihydro-1H-pyrrole-3-carboxamide was prepared using the procedure or modifications to the procedure for Example 50. $^1$H NMR (400 MHz, DMSO-d$_6$) δ ppm 11.11 (s, 1H), 7.91-7.80 (m, 3H), 7.72-7.68 (m, 2H), 7.66 (s, 1H), 7.29-7.19 (m, 3H), 6.92 (t, J=7.3 Hz, 1H), 6.44 (d, J=8.0 Hz, 1H), 6.14 (s, 2H), 4.10-3.95 (m, 2H), 3.86 (s, 2H), 3.35-3.25 (m, 2H), 1.82-1.66 (m, 4H), 1.37 (s, 3H). HRMS calcd for C$_{28}$H$_{29}$F$_3$N$_7$O$_3$S (M+H)$^+$600.2032, found 600.2004. IC$_{50}$=0.004 μM.

Assays

Compounds of the invention were assessed for their ability to selectively inhibit SHP2 activity. The inhibitory properties of the compounds of the invention described herein can be evidenced by testing in any one of the following assays.

SHP2 Allosteric Inhibition Assay

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat #3575) using a final reaction volume of 25 μL and the following assay buffer conditions: 60 mM HEPES, pH 7.2, 75 mM NaCl, 75 mM KCl, 1 mM EDTA, 0.05% P-20, 5 mM DTT.

The inhibition of SHP2 by compounds of the invention (concentrations varying from 0.003-100 μM) was monitored using an assay in which 0.5 nM of SHP2 was incubated with of 0.5 μM of peptide IRS 1_pY1172(dPEG8)pY1222 (sequence: H2N-LN(pY)IDLDLV(dPEG8)LST(pY)AS-INFQK-amide) (SEQ ID NO:1 and SEQ ID NO: 2, respectively, in order of appearance). After 30-60 minutes incubation at 25° C., the surrogate substrate DiFMUP (Invitrogen, cat #D6567) was added to the reaction and incubated at 25° C. for 30 minutes. The reaction was then quenched by the addition of 5 μl of a 160 μM solution of bpV(Phen) (Enzo Life Sciences cat #ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized $IC_{50}$ regression curve fitting with control based normalization. $IC_{50}$ results for compounds of the invention are shown in examples and tables 1-7, above.

p-ERK Cellular Assay p-ERK cellular assay using the AlphaScreen® SureFire™ Phospho-ERK 1/2 Kit (PerkinElmer): KYSE-520 cells (30,000 cells/well) were grown in 96-well plate culture overnight and treated with Shp2 inhibitors at concentrations of 20, 6.6, 2.2, 0.74, 0.24, 0.08, 0.027 μM for 2 hrs at 37° C. Incubations were terminated by addition of 30 μL of lysis buffer (PerkinElmer) supplied with the SureFire phospho-extracellular signal-regulated kinase (pERK) assay kit (PerkinElmer). Samples were processed according to the manufacturer's directions. The fluorescence signal from pERK was measured in duplicate using a 2101 multilabel reader (Perkin Elmer Envision). The percentage of inhibition was normalized by the total ERK signal and compared with the DMSO vehicle control.

Colony Formation Assay and Cell Proliferation Assay

KYSE-520 Cells (1500 cells/well) were plated onto 24-well plates in 300 μL medium (RPMI-1640 containing 10% FBS, Lonza). For drug treatment, compounds of the invention at various concentrations (20, 10, 5, 2.5, 1.25 μM) were added 24 hours and 5 days after cell plating. At day 11, colonies were stained with 0.2% crystal violet (MP Biomedicals) and subsequently dissolved in 20% acetic acid for quantitation using a Spectramax reader (Thermo Scientific). In cell proliferation assay, cells (1500-cells/well) were plated onto 96-well plates in 100 μL medium (RPMI-1640 containing 10% FBS, Lonza). At day 6, 50 μL Celltiter-Glo reagent (Promega) was added, and the luminescent signal was determined according to the supplier's instruction (Promega).

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound selected from formula I and II:

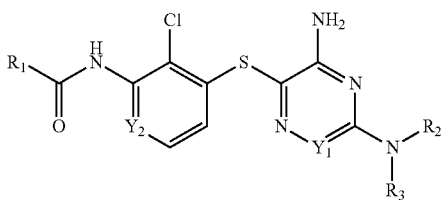

in which:

R₁ is selected from:

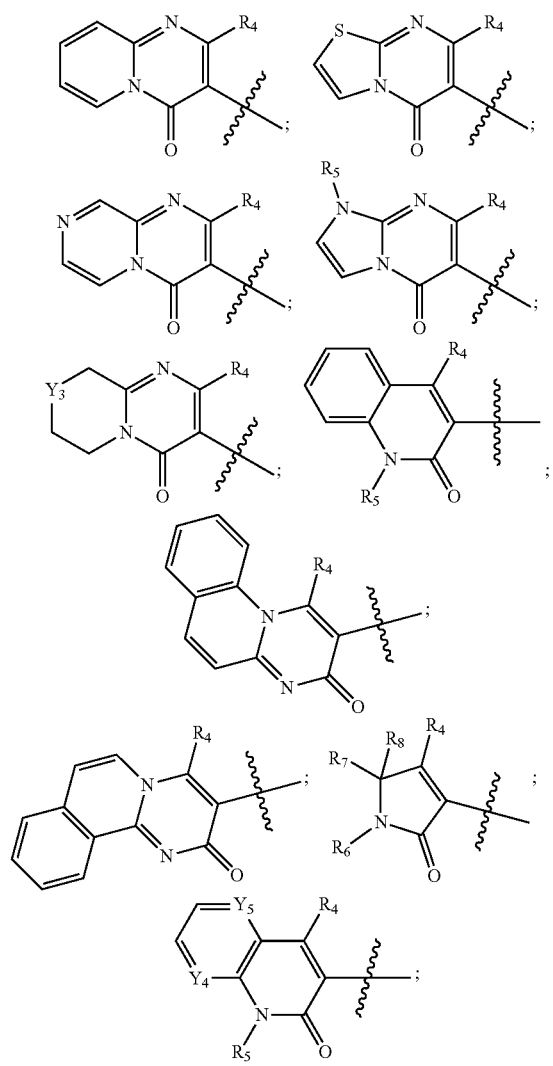

R₂ and R₃ together with the nitrogen to which both R₂ and R₃ are attached form a ring selected from piperidinyl, piperazinyl, 2-oxa-8-azaspiro[4.5]decan-8-yl, 8-azaspiro[4.5]decan-8-yl and pyrrolidinyl; wherein said pyrrolidinyl, piperazinyl, 2-oxa-8-azaspiro[4.5]decan-8-yl, 8-azaspiro[4.5]decan-8-yl or piperidinyl is unsubstituted or substituted with 1 to 3 groups independently selected from amino, methyl, ethyl, amino-methyl, methyl-amino, hydroxyl, cyano, fluoro-methyl, fluoro and (((((5-methyl-2-oxo-1,3-dioxol-4-yl)methoxy)carbonyl)amino)methyl;

R₄ is selected from hydroxyl, $C_{1-3}$alkoxy and $OC(O)C_{1-3}$alkyl;

R₅ is selected from H and methyl;

R₆ is selected from hydrogen, methyl and phenyl;

R₇ is selected from hydrogen, methyl, ethyl, phenyl and benzyl;

R₈ is selected from hydrogen and methyl;

Y₁ is selected from N and CH;

Y₂ is selected from N and CH;

Y₃ is selected from NH and CH₂;

Y₄ is selected from N and CH;

Y₅ is selected from N and CH; or a pharmaceutically acceptable salt thereof.

2. The compound of claim 1 of formula I:

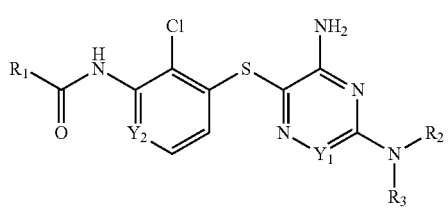

in which:

R₁ is selected from:

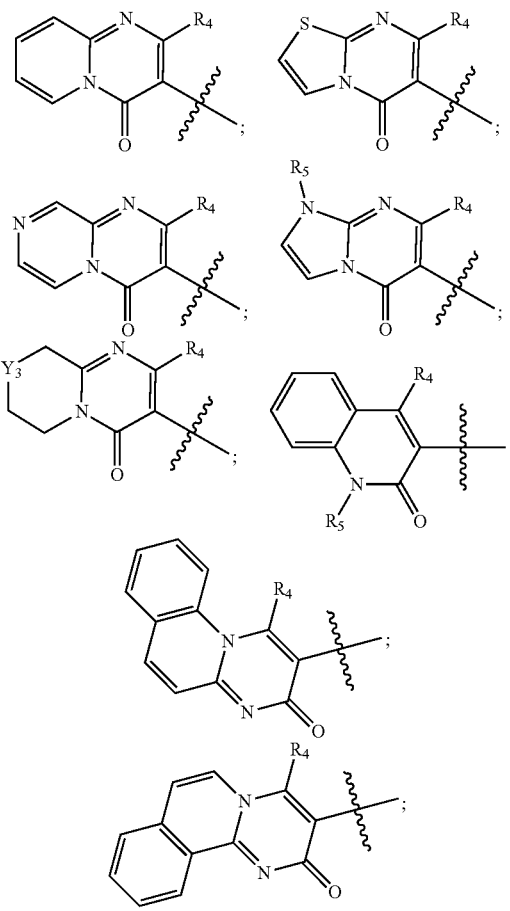

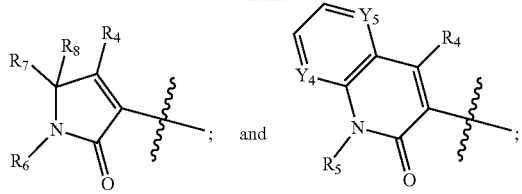

R₂ and R₃ together with the nitrogen to which both R₂ and R₃ are attached form a ring selected from piperidinyl, piperazinyl, 2-oxa-8-azaspiro[4.5]decan-8-yl, 8-azaspiro[4.5]decan-8-yl and pyrrolidinyl; wherein said pyrrolidinyl, piperazinyl, 2-oxa-8-azaspiro[4.5]decan-8-yl, 8-azaspiro[4.5]decan-8-yl or piperidinyl is unsubstituted or substituted with 1 to 3 groups independently selected from amino, methyl, ethyl, amino-methyl, methyl-amino, hydroxyl, cyano, fluoro-methyl, fluoro and (((((5-methyl-2-oxo-1,3-dioxol-4-yl)methoxy)carbonyl)amino)methyl;

R₄ is selected from hydroxyl;
R₅ is selected from H and methyl;
R₆ is selected from hydrogen, methyl and phenyl;
R₇ is selected from hydrogen, methyl, ethyl, phenyl and benzyl;
R₈ is selected from hydrogen and methyl;
Y₁ is selected from N and CH;
Y₂ is selected from N and CH;
Y₃ is selected from NH and CH₂;
Y₄ is selected from N and CH;
Y₅ is selected from N and CH; or a pharmaceutically acceptable salt thereof.

3. The compound of claim 2, or the pharmaceutically acceptable salt thereof, selected from:

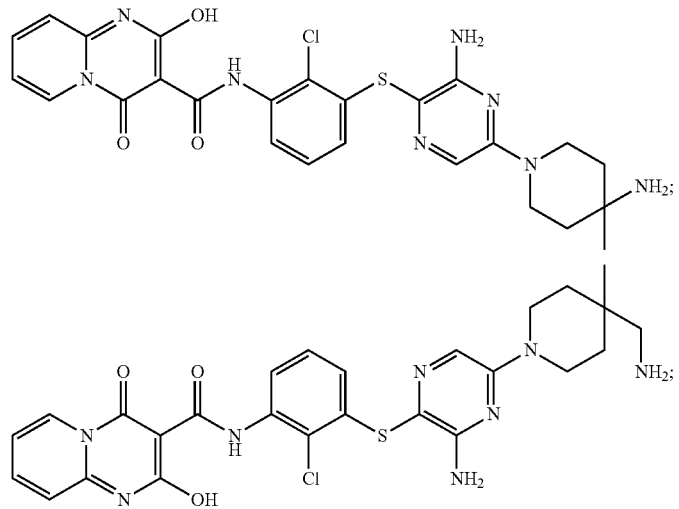

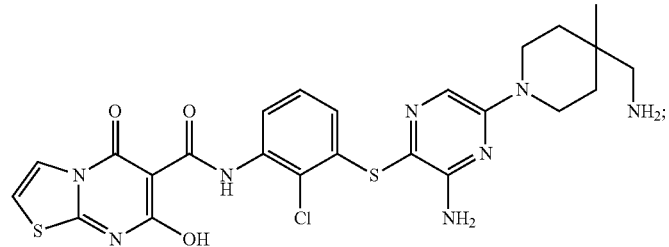

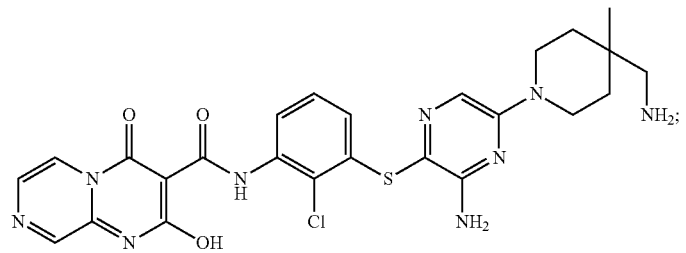

-continued
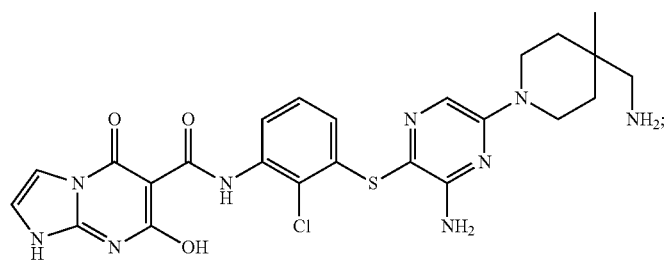
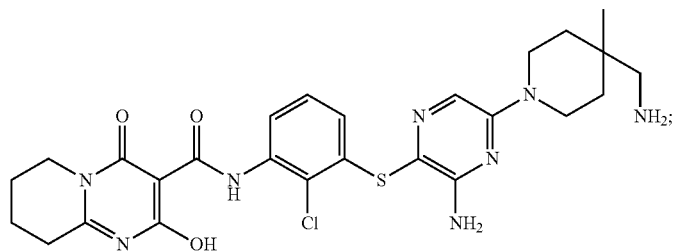
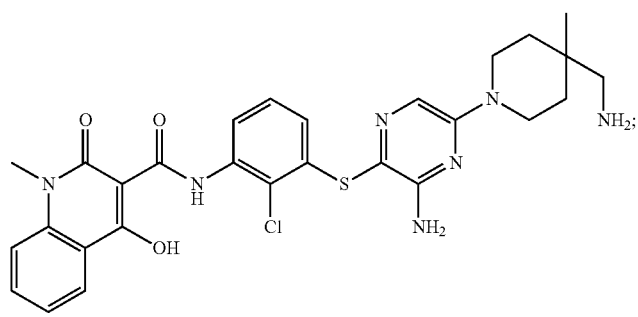
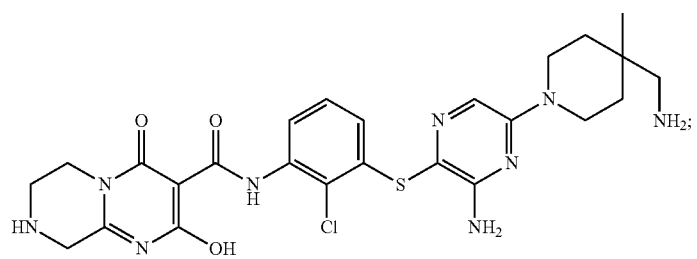
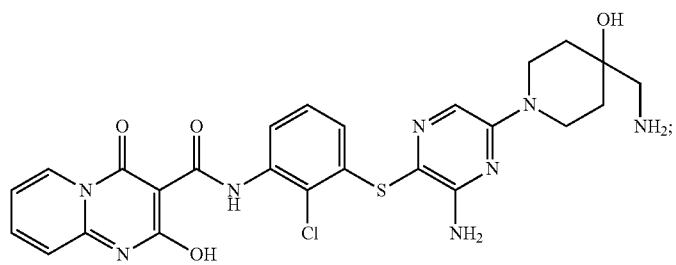
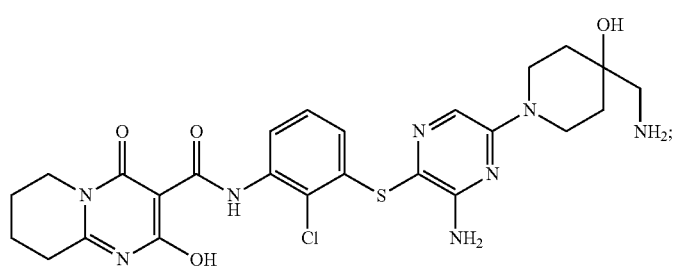

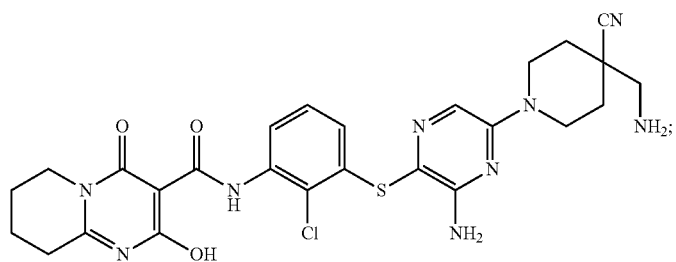
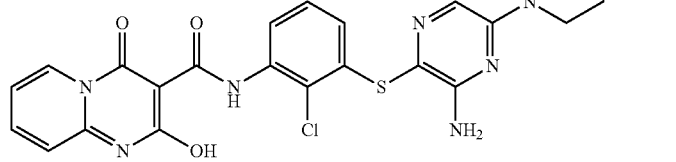
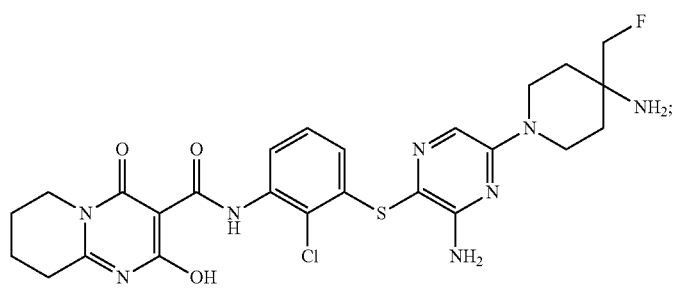
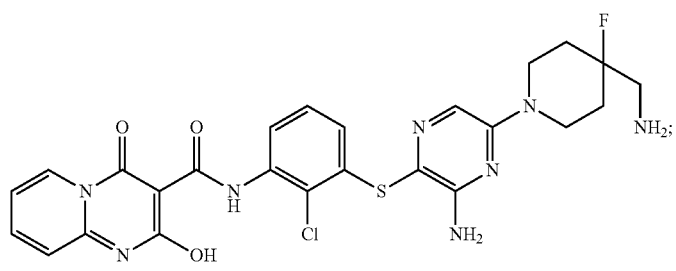
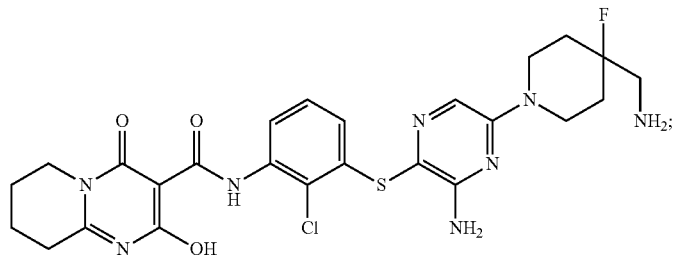
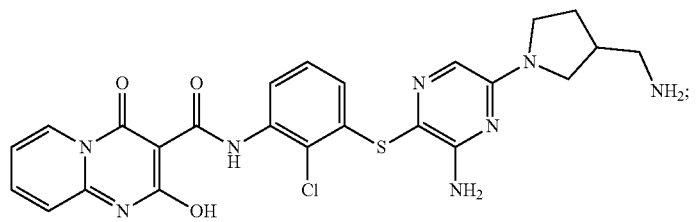

-continued
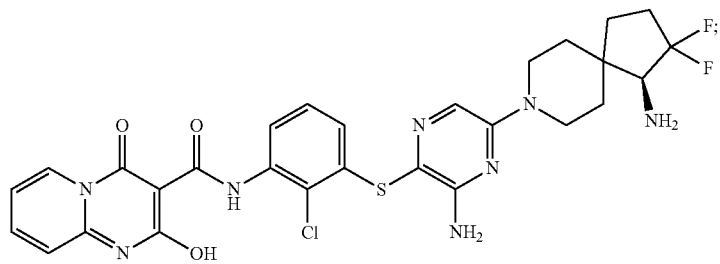
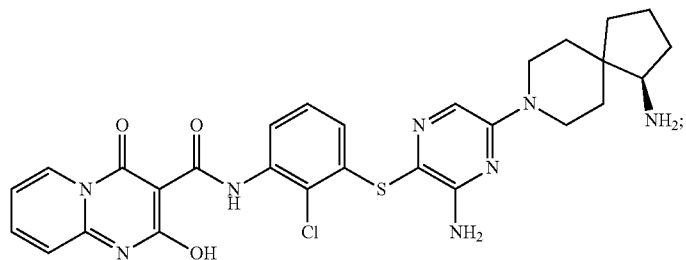
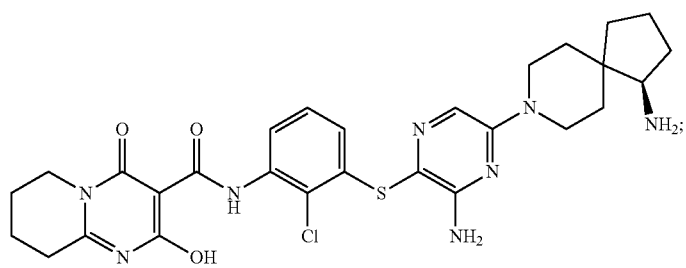
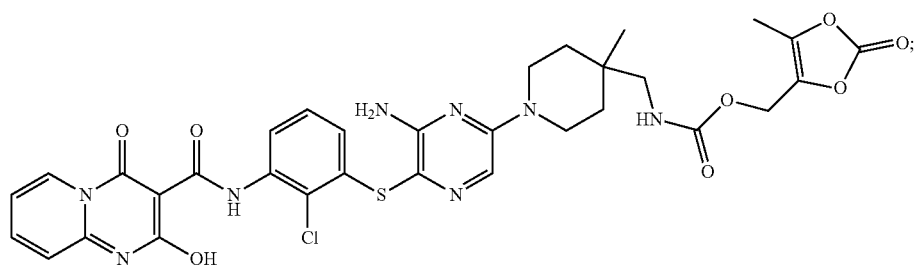
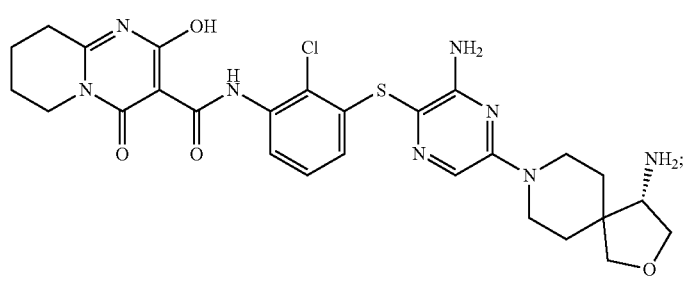
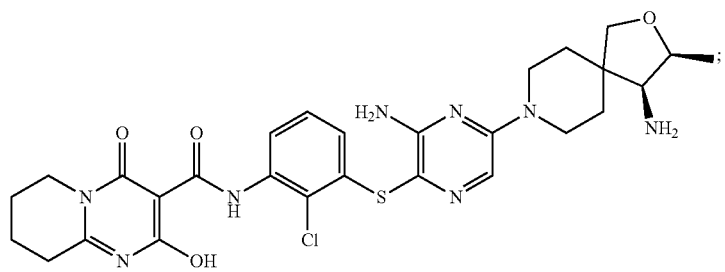

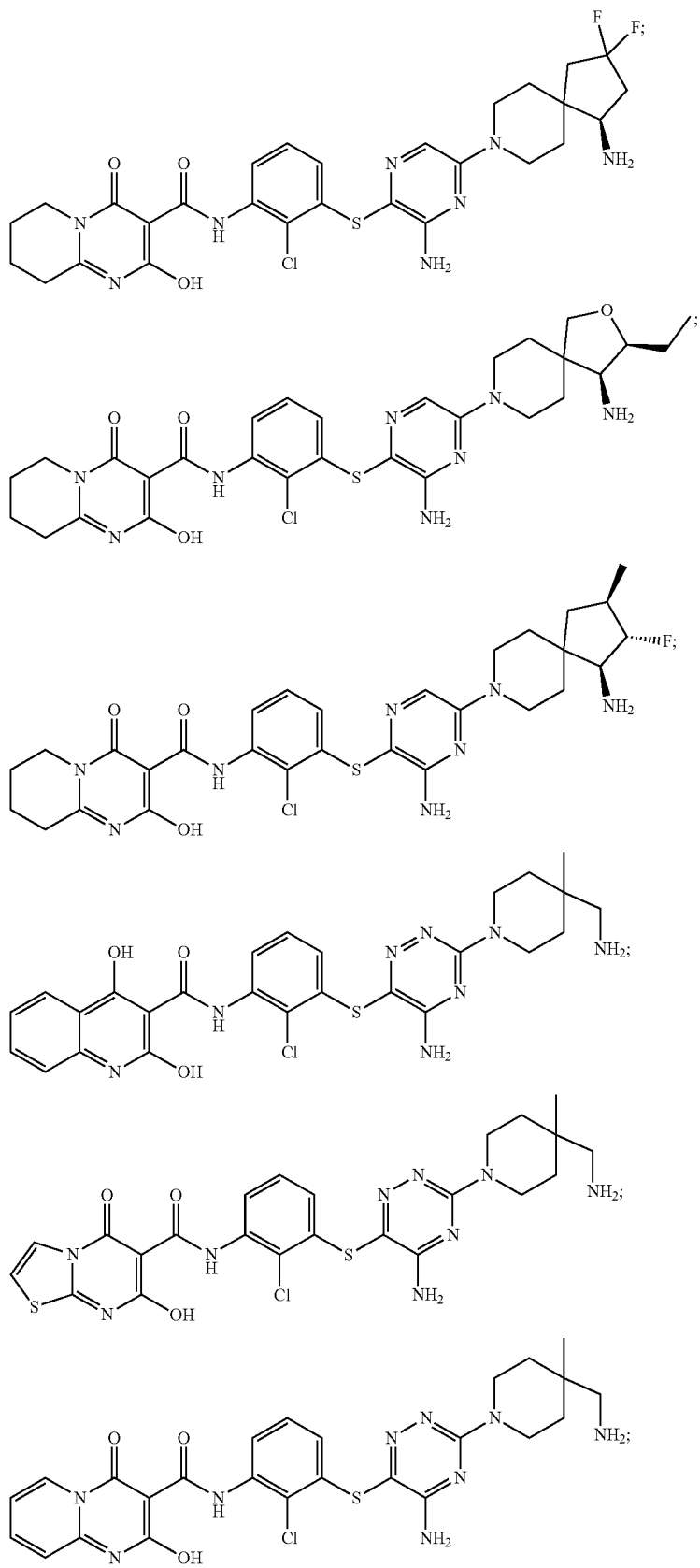

-continued
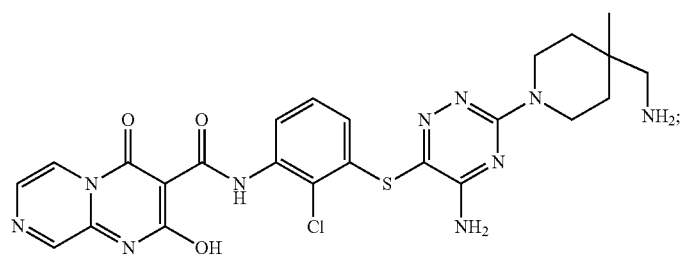
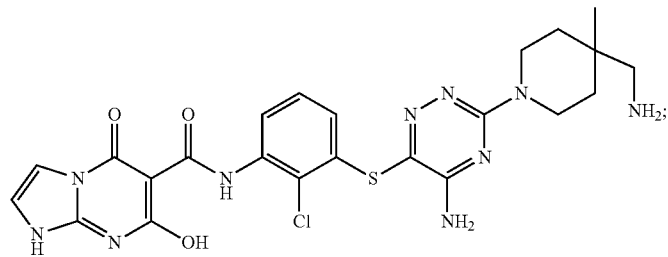
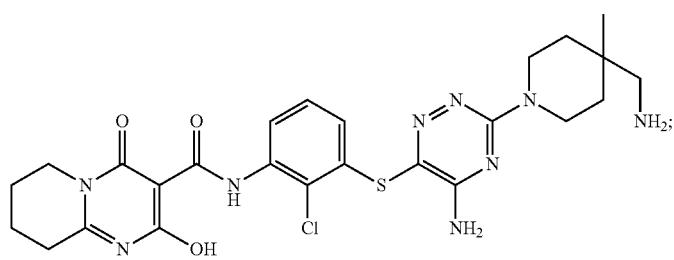
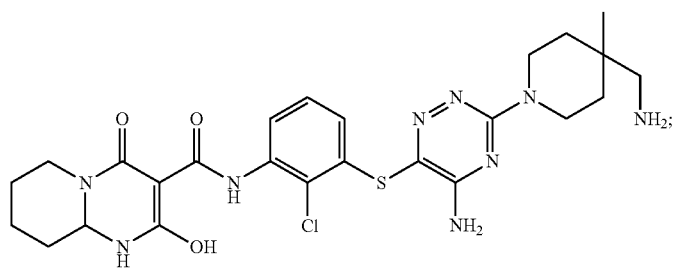
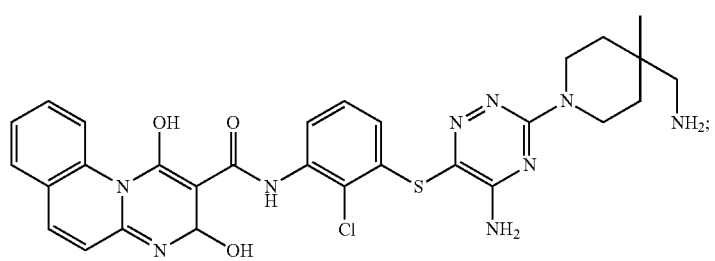
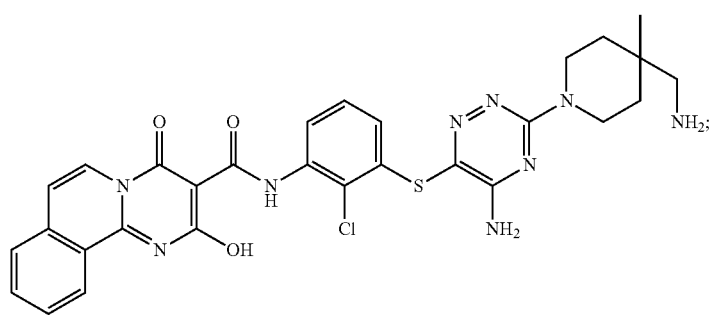

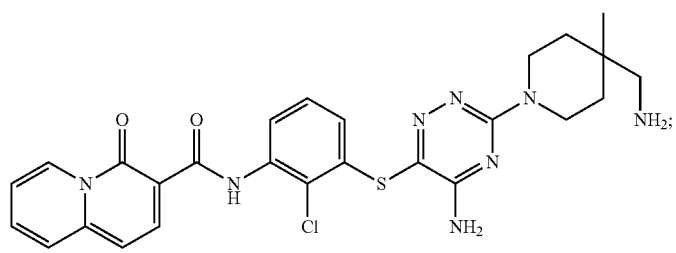
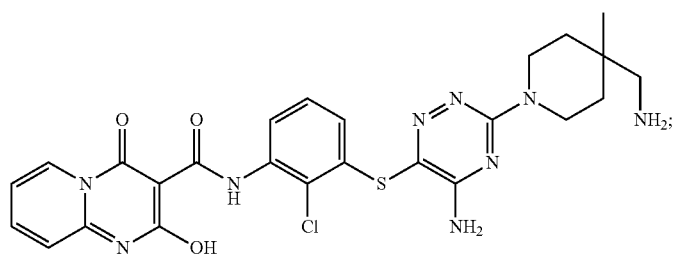
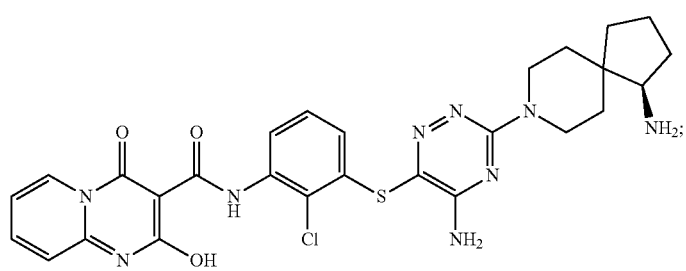
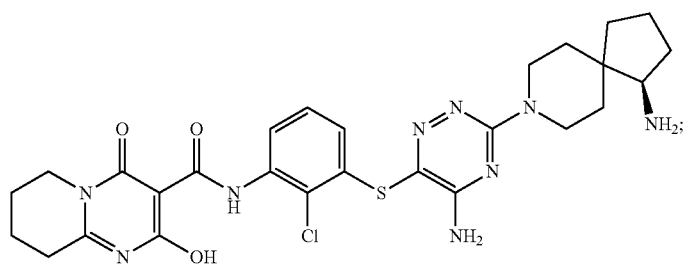
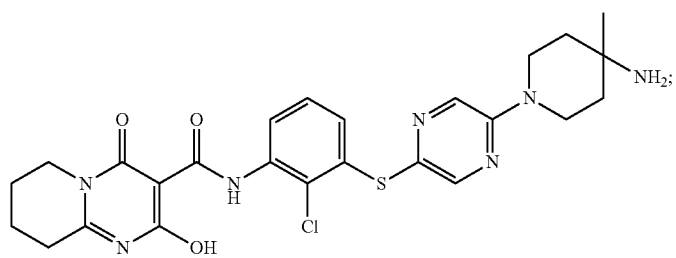
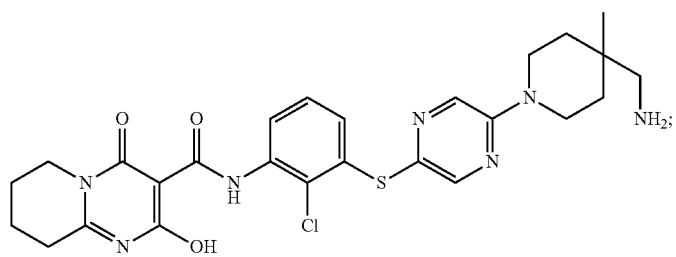

-continued
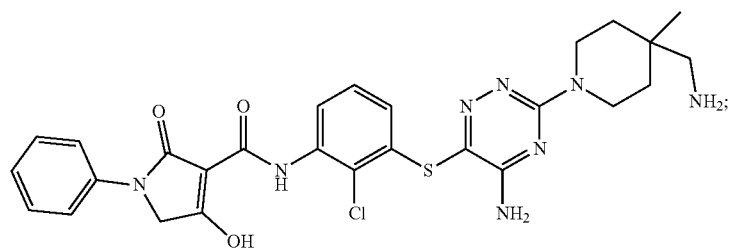
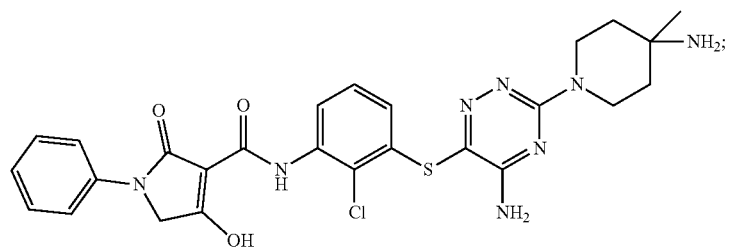
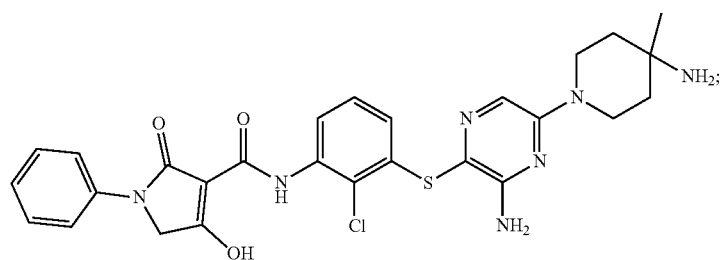
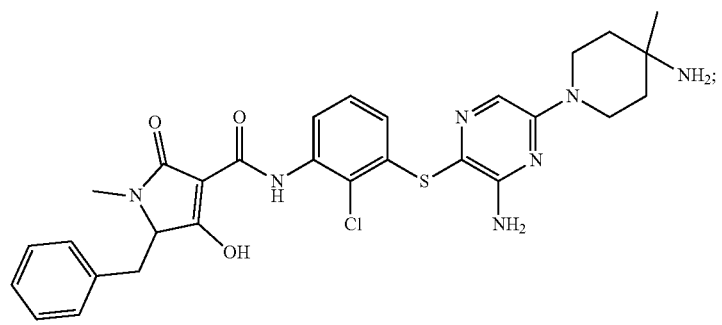
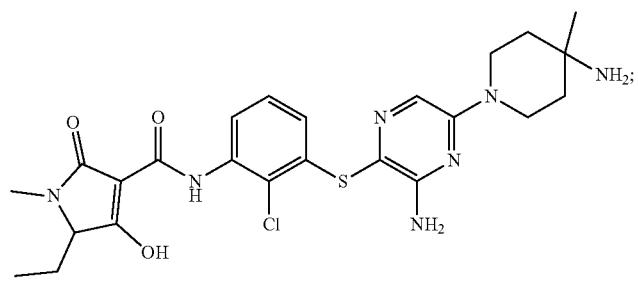
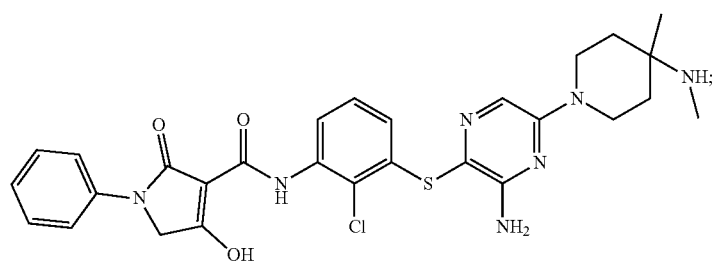

-continued
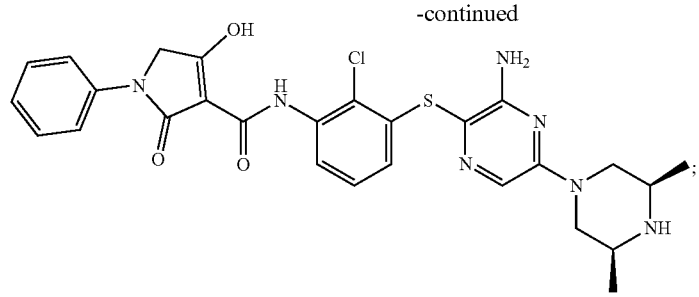
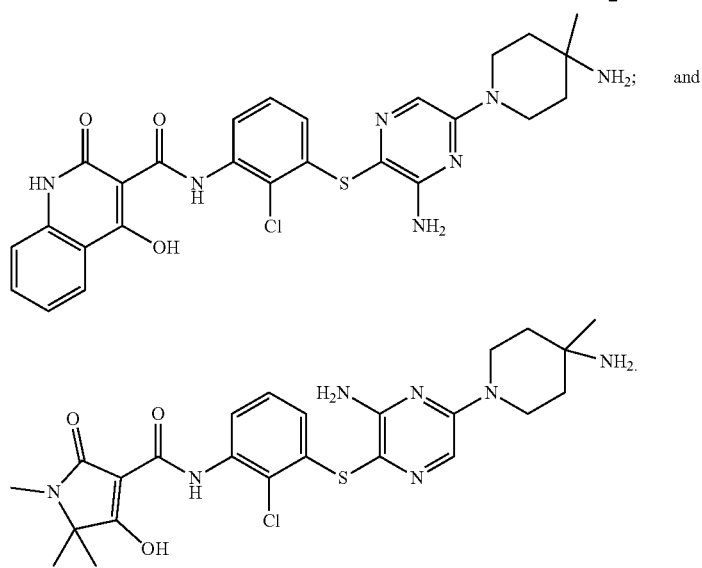
4. N-(3-((3-Amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide, or a pharmaceutically acceptable salt thereof.
5. A pharmaceutical composition comprising a compound of claim 1 or a pharmaceutically acceptable salt thereof, and at least one pharmaceutically acceptable carrier.
* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      biphosphorylated peptide derived from insulin
      receptor substrate-1 (IRS-1)
<220> FEATURE:
<221> NAME/KEY: MOD_RES
<222> LOCATION: (3)..(3)
<223> OTHER INFORMATION: Phosphorylated tyrosine

<400> SEQUENCE: 1

Leu Asn Tyr Ile Asp Leu Asp Leu Val
1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      biphosphorylated peptide derived from insulin
      receptor substrate-1 (IRS-1)
<220> FEATURE:
<221> NAME/KEY: MOD_RES
<222> LOCATION: (4)..(4)
<223> OTHER INFORMATION: Phosphorylated tyrosine
<220> FEATURE:
<223> OTHER INFORMATION: C-term amide

<400> SEQUENCE: 2

Leu Ser Thr Tyr Ala Ser Ile Asn Phe Gln Lys
1               5                   10
```